(12) United States Patent
Lim et al.

(10) Patent No.: US 7,662,583 B2
(45) Date of Patent: Feb. 16, 2010

(54) **BIOREACTOR CONTAINING CELLS EXPRESSING GLYCOSYLTRANSFERASE NUCLEIC ACIDS ISOLATABLE FROM *ARABIDOPSIS***

(75) Inventors: Eng-Kiat Lim, Heslington (GB); Dianna Bowles, Heslington (GB)

(73) Assignee: The University of York, Heslington, York (GB)

( * ) Notice: Subject to any disclaimer, the term of this patent is extended or adjusted under 35 U.S.C. 154(b) by 255 days.

(21) Appl. No.: 10/558,220

(22) PCT Filed: May 24, 2004

(86) PCT No.: PCT/GB2004/002237

§ 371 (c)(1),
(2), (4) Date: Dec. 11, 2006

(87) PCT Pub. No.: WO2004/106508

PCT Pub. Date: Dec. 9, 2004

(65) Prior Publication Data

US 2007/0124832 A1 May 31, 2007

(30) Foreign Application Priority Data

May 27, 2003 (GB) .................. 0312042.5
Jun. 28, 2003 (GB) .................. 0315183.4

(51) Int. Cl.
*C12P 1/00* (2006.01)
*C12N 1/00* (2006.01)
*C12N 5/14* (2006.01)
*C12N 5/16* (2006.01)
*C12N 5/10* (2006.01)

(52) U.S. Cl. .................. 435/41; 435/325; 435/348; 435/419; 435/252.3; 800/278; 800/298

(58) Field of Classification Search ........... None
See application file for complete search history.

(56) References Cited

FOREIGN PATENT DOCUMENTS

| WO | WO 01/59140 A1 | | 8/2001 |
|---|---|---|---|
| WO | WO 02/10210 | * | 2/2002 |
| WO | WO 02/103022 A2 | | 12/2002 |
| WO | WO 03/023035 | * | 3/2003 |
| WO | WO 03/023035 A2 | | 3/2003 |

OTHER PUBLICATIONS

Mok et al. Genes encoding zeatin O-glycosyltransferases. (2000) Plant Growth Regulators, vol. 32, pp. 285-287.*
Hefner et al. Arbutin synthase, a novel member of the NRD1beta glycosyltransferase family, is a unique multifunctional enzyme converting various natural products and xenobiotics. (2002) Bioorganic and Medicinal Chemistry; vol. 10, pp. 1731-1741.*
Lacombe B. et al. The identity of plant glutamate receptors. (2001) Science; vol. 292, pp. 1486-1487.*
Lazar et al. Transforming growth factor alpha: mutation of aspartic acid 47 and leucine 48 results in different biological activities. (1988) Mol. Cell. Biol.; vol. 8; pp. 1247-1252.*
Hill et al. Functional analysis of conserved histidines in ADP-glucose pyrophosphorylase from *Escherichia coli*. (1998) Biochem. Biophys. Res. Comm. vol. 244; pp. 573-577.*
Guo et al. Protein tolerance to random amino acid change. (2004) Proc. Natl. Acad. Sci. USA; vol. 101; pp. 9205-9210.*
EMBL Accession No. AB025634 (Apr. 9, 1999).
Accession No. AX372955 (Mar. 1, 2002).
EMBL Accession No. Q9LSY4 (Oct. 1, 2000).
Mok et al., "Genes Encoding Zeatin O-Glycosyltransferases," *Plant Growth Reg.* 32:285-287 (2000).

* cited by examiner

*Primary Examiner*—Cathy Kingdon Worley
(74) *Attorney, Agent, or Firm*—Janet Sleath; Speckman Law Group PLLC

(57) ABSTRACT

We describe glycosyltransferase nucleic acids and proteins isolatable from *Arabidopsis thaliana*, transgenic cells expressing said glycosyltransferases, and bioreactors comprising said transgenic cells together with nutrient medium for supporting the growth of said cell that includes at least one exogenous substrate which is a substrate for said glycosyltransferase, and wherein said nutrient medium does not include an exogenous supply of UDP-glucose.

11 Claims, 40 Drawing Sheets

Figure 1a

ATGAACAAATTTGCGCTTGTCTTCGTACCATTTCCTATACTTGGTCATCTC
AAATCAACCGCCGAGATGGCTAAGCTACTAGTGGAGCAAGAAACTCGCCT
CTCTATCTCCATTATCATCCTTCCTCTTCTTTCCGGAGACGACGTCAGTGCT
TCCGCTTATATCTCAGCTCTTTCCGCCGCATCCAACGACCGCCTTCACTAT
GAAGTGATCTCGGACGGAGATCAACCAACCGTCGGGTTACATGTCGATAA
CCACATCCCGATGGTGAAACGTACCGTTGCAAAACTCGTTGATGACTACT
CAAGGCGGCCGGACTCGCCGAGGCTCGCTGGTTTAGTTGTTGACATGTTTT
GTATCTCGGTGATAGACGTGGCTAATGAGGTTAGTGTTCCGTGTTACTTGT
TTTACACGTCAAACGTTGGGATTCTTGCTCTTGGGTTACATATTCAGATGT
TGTTTGATAAGAAGGAGTACAGTGTCAGTGAAACTGATTTTGAAGACTCG
GAAGTTGTGTTGGATGTTCCGAGTTTGACTTGTCCTTATCCGGTGAAGTGT
CTTCCTTATGGTTTGGCAACGAAAGAGTGGCTTCCTATGTATCTAAATCAA
GGTAGAAGATTCAGAGAGATGAAAGGTATTTTGGTAAATACTTTTGCTGA
GCTTGAACCTTATGCGTTGGAGTCTCTTCACTCTAGTGGTGATACTCCTCG
TGCTTATCCAGTGGGACCATTGTTGCATCTCGAGAACCATGTTGACGGTTC
TAAAGACGAGAAGGGTTCGGACATTTTACGGTGGTTAGATGAACAACCAC
CTAAATCGGTAGTGTTCCTCTGCTTTGGAAGCATAGGAGGCTTTAACGAG
GAACAAGCAAGAGAAATGGCCATTGCACTTGAGAGAAGTGGTCACCGCTT
CTTGTGGTCTCTTCGCCGTGCATCTCGAGATATAGATAAGGAACTTCCCGG
AGAATTCAAGAATCTTGAAGAAATTCTCCCGGAAGGATTCTTTGATCGGA
CAAAGGATAAAGGAAAGGTGATCGGATGGGCTCCACAAGTAGCCGTGCT
GGCTAAGCCAGCAATCGGAGGTTTTGTTACTCATTGCGGGTGGAACTCGA
TACTCGAGAGTCTTTGGTTCGGTGTTCCTATAGCGCCATGGCCGTTATACG
CTGAGCAGAAGTTTAATGCTTTCGTGATGGTGGAGGAGCTTGGTTTGGCA
GTGAAGATAAGAAAGTATTGGCGAGGCGATCAGTTGGTGGGAACGGCGA
CGGTCATAGTGACGGCAGAGGAGATAGAGAGAGGAATCAGATGTTTGAT
GGAGCAAGATAGTGACGTGAGGAATAGAGTGAAGGAGATGAGTAAGAAA
TGTCACATGGCTTTAAAGGATGGTGGCTCGTCTCAATCTGCTTTGAAATTA
TTTATTCAAGACGTTACGAAGTATATTGCTTGA

Figure 1b

MNKFALVFVPFPILGHLKSTAEMAKLLVEQETRLSISIIILPLLSGDDVSASAYI
SALSAASNDRLHYEVISDGDQPTVGLHVDNHIPMVKRTVAKLVDDYSRRPDS
PRLAGLVVDMFCISVIDVANEVSVPCYLFYTSNVGILALGLHIQMLFDKKEYS
VSETDFEDSEVVLDVPSLTCPYPVKCLPYGLATKEWLPMYLNQGRRFREMK
GILVNTFAELEPYALESLHSSGDTPRAYPVGPLLHLENHVDGSKDEKGSDILR
WLDEQPPKSVVFLCFGSIGGFNEEQAREMAIALERSGHRFLWSLRRASRDIDK
ELPGEFKNLEEILPEGFFDRTKDKGKVIGWAPQVAVLAKPAIGGFVTHCGWN
SILESLWFGVPIAPWPLYAEQKFNAFVMVEELGLAVKIRKYWRGDQLVGTAT
VIVTAEEIERGIRCLMEQDSDVRNRVKEMSKKCHMALKDGGSSQSALKLFIQ
DVTKYIA

Figure 2a

ATGAAAGCAGAAGCAGAGATCATCTTCGTTACATATCCATCCCCTGGTCA
TCTTCTTGTCTCCATTGAATTCGCTAAATCTCTCATCAAACGTGATGATCG
CATCCACACCATCACCATCCTCTACTGGGCTTTACCTCTCGCTCCTCAAGC
CCACCTTTTCGCTAAGTCCCTCGTTGCTTCACAGCCTCGAATCCGTCTCCTT
GCGTTGCCTGATGTTCAAAACCCTCCACCATTGGAACTCTTCTTTAAAGCT
CCCGAAGCTTATATTCTTGAGTCCACCAAGAAAACAGTTCCTTTAGTCAGA
GACGCTCTCTCCACTCTAGTTTCTTCACGTAAAGAATCCGGTTCGGTTCGT
GTAGTCGGTTTGGTTATCGATTTTTTTGTGTTCCAATGATCGAAGTGGCA
AACGAGCTTAACCTTCCTTCTTACATCTTCCTAACGTGTAACGCTGGGTTT
TTAAGTATGATGAAGTATCTCCCTGAGAGACATCGCATAACCACTTCTGA
GCTAGATTTAAGCTCCGGCAACGTAGAACATCCAATTCCTGGCTACGTCT
GCTCCGTGCCGACGAAGGTTTTGCCTCCAGGTCTATTCGTGAGAGTCCT
ACGAGGCTTGGGTCGAGATTGCAGAGAAGTTCCCTGGAGCCAAGGGCATT
TTGGTAAACTCAGTCACATGTCTTGAGCAGAATGCATTTGATTACTTCGCT
CGTCTTGATGAGAACTATCCTCCGGTTTACCCGGTCGGACCGGTTCTTAGT
TTGAAGGATCGTCCGTCTCCAAATCTGGACGCATCGGACCGGGATCGGAT
CATGAGATGGCTCGAGGACCAGCCGGAGTCGTCAATTGTGTATATCTGCT
TCGGAAGCCTCGGAATCATTGGCAAGCTGCAGATTGAAGAGATAGCTGAA
GCCTTGGAACTCACCGGCCACAGGTTTCTTTGGTCAATACGTACAAATCCG
ACGGAGAAAGCGAGCCCGTACGATCTGTTGCCGGAGGGATTTCTCGATCG
GACGGCCAGTAAGGGATTGGTGTGTGATTGGGCCCCGCAAGTAGAAGTTC
TGGCCCATAAAGCGCTCGGAGGATTCGTGTCTCACTGCGGTTGGAACTCT
GTACTGGAGAGCTTATGGTTCGGTGTTCCGATCGCCACGTGGCCAATGTA
CGCTGAGCAACAGTTAAACGCATTCTCGATGGTGAAGGAGTTAGGGTTAG
CCGTGGAGCTGCGTTTAGACTACGTTTCGGCGTACGGAGAGATAGTAAAA
GCTGAGGAGATCGCGGGAGCCATACGATCATTGATGGACGGTGAGGATA
CGCCGAGGAAGAGAGTGAAGGAGATGGCGGAAGCGGCGAGGAATGCTTT
GATGGACGGAGGATCTTCGTTTGTTGCGGTTAAACGATTTCTCGACGAGTT
GATCGGCGGAGATGTTTAG

Figure 2b

MKAEAEIFVTYPSPGHLLVSIEFAKSLIKRDDRIHTITILYWALPLAPQAHLFA
KSLVASQPRIRLLALPDVQNPPPLELFFKAPEAYILESTKKTVPLVRDALSTLV
SSRKESGSVRVVGLVIDFFCVPMIEVANELNLPSYIFLTCNAGFLSMMKYLPE
RHRITTSELDLSSGNVEHPIPGYVCSVPTKVLPPGLFVRESYEAWVEIAEKFPG
AKGILVNSVTCLEQNAFDYFARLDENYPPVYPVGPVLSLKDRPSPNLDASDR
DRIMRWLEDQPESSIVYICFGSLGIIGKLQIEEIAEALELTGHRFLWSIRTNPTEK
ASPYDLLPEGFLDRTASKGLVCDWAPQVEVLAHKALGGFVSHCGWNSVLES
LWFGVPIATWPMYAEQQLNAFSMVKELGLAVELRLDYVSAYGEIVKAEEIA
GAIRSLMDGEDTPRKRVKEMAEAARNALMDGGSSFVAVKRFLDELIGGDV

Figure 3a

ATGGTGAAGGAAACAGAGCTAATCTTCATTCCAGTTCCATCCACAGGTCA
TATTCTCGTCCATATTGAATTCGCCAAGCGTCTCATCAATCTCGACCATCG
GATCCACACCATCACTATTCTCAACTTATCCTCACCCTCTTCTCCTCACGCC
TCCGTCTTCGCCAGATCTCTCATCGCTTCCCAGCCCAAAATCCGTCTCCAC
GACCTTCCCCCTATCCAAGATCCTCCTCCATTCGATCTTTACCAAAGAGCT
CCCGAAGCTTACATAGTAAAACTCATCAAGAAAAATACTCCTCTGATAAA
AGACGCCGTCTCCAGCATCGTCGCGTCGCGTCGTGGAGGCTCAGATTCGG
TTCAAGTCGCCGGTTTGGTTCTCGATTTATTCTGCAATTCATTGGTAAAAG
ATGTTGGCAACGAGCTTAATCTTCCTTCTTACATATACCTTACGTGTAACG
CTAGATACTTGGGGATGATGAAATATATTCCGGATCGGCATCGGAAAATC
GCATCTGAGTTCGATTTGAGCTCCGGCGATGAAGAATTGCCGGTTCCGGG
ATTCATAAACGCTATTCCGACGAAATTTATGCCGCCTGGATTGTTCAATAA
GGAAGCTTACGAGGCTTACGTAGAGCTAGCGCCGAGATTCGCAGATGCGA
AGGGTATTTTGGTTAATTCCTTCACGGAGCTTGAGCCGCACCCGTTTGACT
ATTTCTCTCACCTGGAGAAATTCCCTCCGGTTTACCCGGTCGGACCGATTC
TCAGCTTGAAAGATCGAGCGAGTCCGAACGAAGAAGCAGTCGATCGGGA
TCAGATCGTTGGGTGGCTCGATGATCAGCCGGAGTCATCGGTGGTGTTCCT
CTGTTTCGGGAGCAGAGGAAGCGTTGATGAGCCGCAAGTGAAGGAGATA
GCTCGAGCTTTGGAACTCGTCGGCTGCAGATTTCTTTGGTCAATTAGAACA
AGCGGCGACGTCGAGACGAATCCTAACGATGTGTTGCCGGAGGGGTTCAT
GGGCCGAGTAGCAGGCCGAGGTTTGGTATGTGGTTGGGCTCCACAAGTGG
AAGTGTTGGCCCATAAAGCAATAGGAGGATTTGTGTCTCACTGTGGTTGG
AACTCCACGCTTGAAAGCTTATGGTTCGGGGTTCCTGTCGCAACGTGGCC
GATGTACGCAGAGCAACAGCTTAACGCCTTCACGCTGGTGAAAGAGCTTG
GGCTTGCGGTGGACCTGCGGATGGATTACGTGTCGAGTCGTGGGGGTTTG
GTGACTTGTGATGAGATAGCCAGAGCCGTACGATCTTTGATGGACGGTGG
AGATGAGAAGAGAAAAAGGTTAAGGAGATGGCTGATGCGGCAAGGAAG
GCTTTGATGGATGGAGGATCGTCTTCTTTGGCAACTGCTCGATTCATCGCA
GAATTGTTTGAAGATGGTTCGTCGTGCTAA

Figure 3b

MVKETELIFIPVPSTGHILVHIEFAKRLINLDHRIHTITILNLSSPSSPHASVFARS
LIASQPKIRLHDLPPIQDPPPFDLYQRAPEAYIVKLIKKNTPLIKDAVSSIVASRR
GGSDSVQVAGLVLDLFCNSLVKDVGNELNLPSYIYLTCNARYLGMMKYIPD
RHRKIASEFDLSSGDEELPVPGFINAIPTKFMPPGLFNKEAYEAYVELAPRFAD
AKGILVNSFTELEPHPFDYFSHLEKFPPVYPVGPILSLKDRASPNEEAVDRDQI
VGWLDDQPESSVVFLCFGSRGSVDEPQVKEIARALELVGCRFLWSIRTSGDVE
TNPNDVLPEGFMGRVAGRGLVCGWAPQVEVLAHKAIGGFVSHCGWNSTLES
LWFGVPVATWPMYAEQQLNAFTLVKELGLAVDLRMDYVSSRGGLVTCDEI
ARAVRSLMDGGDEKRKKVKEMADAARKALMDGGSSSLATARFIAELFEDGS
SC

Figure 4a

```
ATGGGTGAAGAAGCTATAGTTCTGTATCCTGCACCACCAATAGGTCACTT
AGTGTCCATGGTTGAGTTAGGTAAAACCATCCTCTCCAAAAACCCATCTCT
CTCCATCCACATTATCTTAGTTCCACCGCCTTATCAGCCGGAATCAACCGC
CACTTACATCTCCTCCGTCTCCTCCTCCTTCCCTTCAATAACCTTCCACCAT
CTTCCCGCCGTCACACCGTACTCCTCCTCCTCCACCTCTCGCCACCACCAC
GAATCTCTCCTCCTAGAGATCCTCTGTTTTAGCAACCCAAGTGTCCACCGA
ACTCTTTTCTCACTCTCTCGGAATTTCAATGTCCGAGCAATGATCATCGAT
TTCTTCTGCACCGCCGTTTTAGACATCACCGCTGACTTCACGTTCCCGGTTT
ACTTCTTCTACACCTCTGGAGCCGCATGTCTCGCCTTTTCCTTCTATCTCCC
GACCATCGACGAAACAACCCCCGGAAAAACCTCAAAGACATTCCTACA
GTTCATATCCCCGGCGTTCCTCCGATGAAGGGCTCCGATATGCCTAAGGC
GGTGCTCGAACGAGACGATGAGGTCTACGATGTTTTTATAATGTTCGGTA
AACAGCTCTCGAAGTCGTCAGGGATTATTATCAATACGTTTGATGCTTTAG
AAAACAGAGCCATCAAGGCCATAACAGAGGAGCTCTGTTTTCGCAATATT
TATCCAATTGGACCGCTCATTGTAAACGGAAGAATCGAAGATAGAAACGA
CAACAAGGCAGTTTCTTGTCTCAATTGGCTGGATTCGCAGCCGGAAAAGA
GTGTTGTGTTTCTCTGTTTTGGAAGCTTAGGTTTGTTCTCAAAAGAACAGG
TGATAGAGATTGCTGTTGGTTTAGAGAAAAGTGGGCAGAGATTCTTGTGG
GTGGTCCGTAATCCACCCGAGTTAGAAAAGACAGAACTGGATTTGAAATC
ACTCTTACCAGAAGGATTCTTAAGCCGAACCGAAGACAAAGGGATGGTCG
TGAAATCATGGGCTCCGCAAGTTCCGGTTCTGAATCATAAAGCAGTCGGG
GGATTCGTCACTCATTGCGGTTGGAATTCAATTCTTGAAGCTGTTTGTGCT
GGTAAATAATGTATATATATACACATTTTTCGATTATATATATGCTTAAAA
TGTTCATTGTGGTTAATTGAATTGGTTTACTATATAATAGGTGTGCCGATG
GTGGCTTGGCCGTTGTACGCTGAGCAGAGGTTTAATAGAGTGATGATTGT
GGATGAGATCAAGATTGCGATTTCGATGAATGAATCAGAGACGGGTTTCG
TGAGCTCTACAGAGGTGGAGAAACGAGTCCAAGAGATAATTGGGGAGTG
TCCGGTTAGGGAGCGAACCATGGCTATGAAGAACGCAGCCGAATTAGCCT
TGACAGAAACTGGTTCGTCTCATACCGCATTAACTACTTTACTCCAGTCGT
GGAGCCCAAAGTGA
```

Figure 4b

ATGGGTGAAGAAGCTATAGTTCTGTATCCTGCACCACCAATAGGTCACTT
AGTGTCCATGGTTGAGTTAGGTAAAACCATCCTCTCCAAAAACCCATCTCT
CTCCATCCACATTATCTTAGTTCCACCGCCTTATCAGCCGGAATCAACCGC
CACTTACATCTCCTCCGTCTCCTCCTCCTTCCCTTCAATAACCTTCCACCAT
CTTCCCGCCGTCACACCGTACTCCTCCTCCTCCACCTCTCGCCACCACCAC
GAATCTCTCCTCCTAGAGATCCTCTGTTTTAGCAACCCAAGTGTCCACCGA
ACTCTTTCTCACTCTCTCGGAATTTCAATGTCCGAGCAATGATCATCGAT
TTCTTCTGCACCGCCGTTTTAGACATCACCGCTGACTTCACGTTCCGGTTT
ACTTCTTCTACACCTCTGGAGCCGCATGTCTCGCCTTTTCCTTCTATCTCCC
GACCATCGACGAAACAACCCCCGGAAAAAACCTCAAAGACATTCCTACA
GTTCATATCCCCGGCGTTCCTCCGATGAAGGGCTCCGATATGCCTAAGGC
GGTGCTCGAACGAGACGATGAGGTCTACGATGTTTTATAATGTTCGGTA
AACAGCTCTCGAAGTCGTCAGGGATTATTATCAATACGTTTGATGCTTTAG
AAAACAGAGCCATCAAGGCCATAACAGAGGAGCTCTGTTTTCGCAATATT
TATCCAATTGGACCGCTCATTGTAAACGGAAGAATCGAAGATAGAAACGA
CAACAAGGCAGTTTCTTGTCTCAATTGGCTGGATTCGCAGCCGGAAAAGA
GTGTTGTGTTTCTCTGTTTTGGAAGCTTAGGTTTGTTCTCAAAAGAACAGG
TGATAGAGATTGCTGTTGGTTTAGAGAAAAGTGGGCAGAGATTCTTGTGG
GTGGTCCGTAATCCACCCGAGTTAGAAAAGACAGAACTGGATTTGAAATC
ACTCTTACCAGAAGGATTCTTAAGCCGAACCGAAGACAAAGGGATGGTCG
TGAAATCATGGCTCCGCAAGTTCCGGTTCTGAATCATAAAGCAGTCGGG
GGATTCGTCACTCATTGCGGTTGGAATTCAATTCTTGAAGCTGTTTGTGCT
GGTGTGCCGATGGTGGCTTGGCCGTTGTACGCTGAGCAGAGGTTTAATAG
AGTGATGATTGTGGATGAGATCAAGATTGCGATTTCGATGAATGAATCAG
AGACGGGTTTCGTGAGCTCTACAGAGGTGGAGAAACGAGTCCAAGAGAT
AATTGGGGAGTGTCCGGTTAGGGAGCGAACCATGGCTATGAAGAACGCA
GCCGAATTAGCCTTGACAGAAACTGGTTCGTCTCATACCGCATTAACTACT
TTACTCCAGTCGTGGAGCCCAAAGTGA

Figure 4c

MGEEAIVLYPAPPIGHLVSMVELGKTILSKNPSLSIHHLVPPPYQPESTATYISS
VSSSFPSITFHHLPAVTPYSSSSTSRHHHESLLLEILCFSNPSVHRTLFSLSRNFN
VRAMIIDFFCTAVLDITADFTFPVYFFYTSGAACLAFSFYLPTIDETTPGKNLK
DIPTVHIPGVPPMKGSDMPKAVLERDDEVYDVFIMFGKQLSKSSGIIINTFDAL
ENRAIKAITEELCFRNIYPIGPLIVNGRIEDRNDNKAVSCLNWLDSQPEKSVVF
LCFGSLGLFSKEQVIEIAVGLEKSGQRFLWVVRNPPELEKTELDLKSLLPEGFL
SRTEDKGMVVKSWAPQVPVLNHKAVGGFVTHCGWNSILEAVCAGVPMVA
WPLYAEQRFNRVMIVDEIKIAISMNESETGFVSSTEVEKRVQEIIGECPVRERT
MAMKNAAELALTETGSSHTALTTLLQSWSPK

Figure 5a

ATGACCAAACCCTCCGACCCAACCAGAGACTCCCACGTGGCAGTTCTCGC
TTTTCCTTTCGGCACTCATGCAGCTCCTCTCCTCACCGTCACGCGCCGCCTC
GCCTCCGCCTCTCCTTCCACCGTCTTCTCTTTCTTCAACACCGCACAATCCA
ACTCTTCGTTATTTTCCTCCGGTGACGAAGCAGATCGTCCGGCGAACATCA
GAGTATACGATATTGCCGACGGTGTTCCGGAGGGATACGTGTTTAGCGGG
AGACCACAGGAGGCGATCGAGCTGTTTCTTCAAGCTGCGCCGGAGAATTT
CCGGAGAGAAATCGCGAAGGCGGAGACGGAGGTTGGTACGGAAGTGAAA
TGTTTGATGACTGATGCGTTCTTCTGGTTCGCGGCTGATATGGCGACGGAG
ATAAATGCGTCGTGGATTGCGTTTGGACCGCCGGAGCAAACTCACTCTCT
GCTCATCTCTACACAGATCTCATCAGAGAACCATCGGTGTCAAAGGTAA
TATATACAAATTTTTGAATGCTTCCCAATTCCGACTTGTGATTTTGTCTTTT
ATCTCATAAATAAATATGCAACTAGAGGAAAATTTAGCTAAAAGAAGAAA
CAGAGGTTAAGATACTATTGATTTGAAGATTTATATGTATTTGTGGTAATG
TTTATGATTCCATTCTAATTTACAGAAGTAGGTGAGCGTATGGAGGAGAC
AATAGGGGTTATCTCAGGAATGGAGAAGATCAGAGTCAAAGATACACCA
GAAGGAGTTGTGTTTGGGAATTTAGACTCTGTTTTCTCAAAGATGCTTCAT
CAAATGGGTCTTGCTTTGCCTCGTGCCACTGCTGTTTTCATCAATTCTTTTG
AAGATTTGGATCCTACATTGACGAATAACCTCAGATCGAGATTTAAACGA
TATCTGAACATCGGTCCTCTCGGGTTATTATCTTCTACATTGCAACAACTA
GTGCAAGATCCTCACGGTTGTTTGGCTTGGATGGAGAAGAGATCTTCTGGT
TCTGTGGCGTACATTAGCTTTGGTACGGTCATGACACCGCCTCCTGGAGAG
CTTGCGGCGATAGCAGAAGGGTTGGAATCGAGTAAAGTGCCGTTTGTTTG
GTCGCTTAAGGAGAAGAGCTTGGTTCAGTTACCAAAAGGGTTTTTGGATA
GGACAAGAGAGCAAGGGATAGTGGTTCCATGGGCACCGCAAGTGGAACT
GCTGAAACACGAAGCAACGGGTGTGTTTGTGACGCATTGTGGATGGAACT
CGGTGTTGGAGAGTGTATCGGGTGGTGTACCGATGATTTGCAGGCCATTTT
TTGGGGATCAGAGATTGAACGGAAGAGCGGTGGAGGTTGTGTGGGAGATT
GGAATGACGATTATCAATGGAGTCTTCACGAAAGATGGGTTTGAGAAGTG
TTTGGATAAAGTTTTAGTTCAAGATGATGGTAAGAAGATGAAATGTAATG
CTAAGAAACTTAAAGAACTAGCTTACGAAGCTGTCTCTTCTAAAGGAAGG
TCCTCTGAGAATTTCAGAGGATTGTTGGATGCAGTTGTAAACATTATTTGA

Figure 5b

ATGACCAAACCCTCCGACCCAACCAGAGACTCCCACGTGGCAGTTCTCGC
TTTTCCTTTCGGCACTCATGCAGCTCCTCTCCTCACCGTCACGCGCCGCCTC
GCCTCCGCCTCTCCTTCCACCGTCTTCTCTTTCTTCAACACCGCACAATCCA
ACTCTTCGTTATTTTCCTCCGGTGACGAAGCAGATCGTCCGGCGAACATCA
GAGTATACGATATTGCCGACGGTGTTCCGGAGGGATACGTGTTAGCGGG
AGACCACAGGAGGCGATCGAGCTGTTTCTTCAAGCTGCGCCGGAGAATTT
CCGGAGAGAAATCGCGAAGGCGGAGACGGAGGTTGGTACGGAAGTGAAA
TGTTTGATGACTGATGCGTTCTTCTGGTTCGCGGCTGATATGGCGACGGAG
ATAAATGCGTCGTGGATTGCGTTTTGGACCGCCGGAGCAAACTCACTCTCT
GCTCATCTCTACACAGATCTCATCAGAGAAACCATCGGTGTCAAAGAAGT
AGGTGAGCGTATGGAGGAGACAATAGGGGTTATCTCAGGAATGGAGAAG
ATCAGAGTCAAAGATACACCAGAAGGAGTTGTGTTTGGGAATTTAGACTC
TGTTTTCTCAAAGATGCTTCATCAAATGGGTCTTGCTTTGCCTCGTGCCAC
TGCTGTTTTCATCAATTCTTTTGAAGATTTGGATCCTACATTGACGAATAA
CCTCAGATCGAGATTTAAACGATATCTGAACATCGGTCCTCTCGGGTTATT
ATCTTCTACATTGCAACAACTAGTGCAAGATCCTCACGGTTGTTTGGCTTG
GATGGAGAAGAGATCTTCTGGTTCTGTGGCGTACATTAGCTTTGGTACGGT
CATGACACCGCCTCCTGGAGAGCTTGCGGCGATAGCAGAAGGGTTGGAAT
CGAGTAAAGTGCCGTTTGTTTGGTCGCTTAAGGAGAAGAGCTTGGTTCAG
TTACCAAAAGGGTTTTTGGATAGGACAAGAGAGCAAGGGATAGTGGTTCC
ATGGGCACCGCAAGTGGAACTGCTGAAACACGAAGCAACGGGTGTGTTTG
TGACGCATTGTGGATGGAACTCGGTGTTGGAGAGTGTATCGGGTGGTGTA
CCGATGATTTGCAGGCCATTTTTTGGGGATCAGAGATTGAACGGAAGAGC
GGTGGAGGTTGTGTGGGAGATTGGAATGACGATTATCAATGGAGTCTTCA
CGAAAGATGGGTTTGAGAAGTGTTTGGATAAAGTTTTAGTTCAAGATGAT
GGTAAGAAGATGAAATGTAATGCTAAGAAACTTAAAGAACTAGCTTACGA
AGCTGTCTCTTCTAAAGGAAGGTCCTCTGAGAATTTCAGAGGATTGTTGGA
TGCAGTTGTAAACATTATTTGA

Figure 5c

MTKPSDPTRDSHVAVLAFPFGTHAAPLLTVTRRLASASPSTVFSFFNTAQSNS
SLFSSGDEADRPANIRVYDIADGVPEGYVFSGRPQEAIELFLQAAPENFRREIA
KAETEVGTEVKCLMTDAFFWFAADMATEINASWIAFWTAGANSLSAHLYTD
LIRETIGVKEVGERMEETIGVISGMEKIRVKDTPEGVVFGNLDSVFSKMLHQM
GLALPRATAVFINSFEDLDPTLTNNLRSRFKRYLNIGPLGLLSSTLQQLVQDPH
GCLAWMEKRSSGSVAYISFGTVMTPPPGELAAIAEGLESSKVPFVWSLKEKSL
VQLPKGFLDRTREQGIVVPWAPQVELLKHEATGVFVTHCGWNSVLESVSGG
VPMICRPFFGDQRLNGRAVEVVWEIGMTIINGVFTKDGFEKCLDKVLVQDDG
KKMKCNAKKLKELAYEAVSSKGRSSENFRGLLDAVVNII

Figure 6a

ATGGCCAAACCCTCGCAGCCAACGCGAGACTCCCACGTGGCAGTTCTCGT
TTTCCCCTTCGGCACTCATGCAGCTCCTCTCCTCGCCGTCACGTGCCGTCTC
GCCACCGCTGCTCCCTCCACCGTCTTCTCCTTCTTCAGCACCGCACGATCC
AACTCGTCGTTACTCTCCTCCGATATCCCCACAAACATTCGTGTCCACAAC
GTCGATGACGGTGTTCCTGAGGGATTCGTGTTGACGGGGAATCCACAGCA
CGCTGTTGAGCTGTTTCTTGAAGCGGCGCCAGAGATTTTCCGAAGAGAAA
TCAAGGCGGCCGAGACCGAAGTTGGTAGGAAGTTCAAGTGCATCCTTACG
GATGCGTTCCTCTGGTTAGCAGCGGAGACGGCGGCTGCGGAGATGAAAGC
GTCGTGGGTTGCGTACTATGGAGGCGGAGCAACCTCGCTCACTGCTCATC
TCTACACAGATGCCATCAGAGAAACGTCGGTGTCAAAGGTATACACAAA
TCTTTTCTTGCTTTACGATTCCATTGAAATTTCAATATTGCAACTATAGATG
CCTTATAGGGCAAGTAAACCTGCCTGTTCCACAATAATCCCCGAGGGAT
TTTTAAAAGAAATGTCTCCATTCTAATTTTCAGAAGTAGGTGAGCGTATGG
AGGAGACAATAGGGTTTATCTCAGGAATGGAGAAGATCAGAGTCAAAGA
CACACAAGAAGGCGTTGTGTTTGGGAACTTAGACTCTGTTTTCTCTAAAAC
GTTGCACCAAATGGGTCTTGCTTTACCTCGTGCCACTGCTGTTTTCATCAA
TTCCTTTGAAGAATTGGATCCTACGTTACAAATGATTTCAGATCGGAATT
CAAACGTTACCTAAACATCGGTCCTCTCGCTTTATTATCTTCTCCATCGCA
AACATCAACGCTAGTGCACGATCCTCACGGTTGCTTGGCTTGGATCGAGA
AGCGGTCCACTGCTTCTGTAGCGTACATTGCCTTTGGTAGAGTCGCGACAC
CGCCTCCTGTAGAGCTTGTGGCGATAGCACAAGGATTGGAATCGAGTAAA
GTGCCTTTTGTTTGGTCGCTACAAGAGATGAAAATGACTCATTTACCAGAA
GGCTTTTTGGATCGGACCAGAGAGCAAGGGATGGTGGTTCCATGGGCACC
ACAAGTGGAGCTGCTAAACCATGAAGCAATGGGTGTGTTTGTTTCGCATG
GTGGGTGGAACTCAGTGTTGGAGAGTGTGTCGGCAGGTGTACCGATGATT
TGTAGACCGATTTTCGGGGATCATGCAATCAATGCAAGATCTGTGGAAGC
TGTGTGGGAGATCGGAGTGACGATTAGTAGTGGAGTCTTCACGAAGGATG
GATTTGAGGAGAGTTTGGATCGGGTTTTGGTTCAAGATGATGGCAAGAAG
ATGAAGGTTAATGCTAAAAAGCTTGAAGAACTAGCACAAGAAGCTGTCTC
TACCAAAGGAAGCTCCTTTGAGAATTTTGGAGGATTGTTGGACGAAGTTG
TGAACTTTGGATAA

Figure 6b

ATGGCCAAACCCTCGCAGCCAACGCGAGACTCCCACGTGGCAGTTCTCGT
TTTCCCCTTCGGCACTCATGCAGCTCCTCTCCTCGCCGTCACGTGCCGTCTC
GCCACCGCTGCTCCCTCCACCGTCTTCTCCTTCTTCAGCACCGCACGATCC
AACTCGTCGTTACTCTCCTCCGATATCCCCACAAACATTCGTGTCCACAAC
GTCGATGACGGTGTTCCTGAGGGATTCGTGTTGACGGGGAATCCACAGCA
CGCTGTTGAGCTGTTTCTTGAAGCGGCGCCAGAGATTTTCCGAAGAGAAA
TCAAGGCGGCCGAGACCGAAGTTGGTAGGAAGTTCAAGTGCATCCTTACG
GATGCGTTCCTCTGGTTAGCAGCGGAGACGGCGGCTGCGGAGATGAAAGC
GTCGTGGGTTGCGTACTATGGAGGCGGAGCAACCTCGCTCACTGCTCATC
TCTACACAGATGCCATCAGAGAAACGTCGGTGTCAAAAGTAGGTGAGCG
TATGGAGGAGACAATAGGGTTTATCTCAGGAATGGAGAAGATCAGAGTCA
AAGACACACAAGAAGGCGTTGTGTTTGGGAACTTAGACTCTGTTTCTCTA
AAACGTTGCACCAAATGGGTCTTGCTTTACCTCGTGCCACTGCTGTTTTCA
TCAATTCCTTTGAAGAATTGGATCCTACGTTTACAAATGATTTCAGATCGG
AATTCAAACGTTACCTAAACATCGGTCCTCTCGCTTTATTATCTTCTCCATC
GCAAACATCAACGCTAGTGCACGATCCTCACGGTTGCTTGGCTTGGATCG
AGAAGCGGTCCACTGCTTCTGTAGCGTACATTGCCTTTGGTAGAGTCGCG
ACACCGCCTCCTGTAGAGCTTGTGGCGATAGCACAAGGATTGGAATCGAG
TAAAGTGCCTTTTGTTTGGTCGCTACAAGAGATGAAAATGACTCATTTACC
AGAAGGCTTTTTGGATCGGACCAGAGAGCAAGGGATGGTGGTTCCATGGG
CACCACAAGTGGAGCTGCTAAACCATGAAGCAATGGGTGTGTTTGTTTCG
CATGGTGGGTGGAACTCAGTGTTGGAGAGTGTGTCGGCAGGTGTACCGAT
GATTTGTAGACCGATTTCGGGGATCATGCAATCAATGCAAGATCTGTGG
AAGCTGTGTGGGAGATCGGAGTGACGATTAGTAGTGGAGTCTTCACGAAG
GATGGATTTGAGGAGAGTTTGGATCGGGTTTTGGTTCAAGATGATGGCAA
GAAGATGAAGGTTAATGCTAAAAAGCTTGAAGAACTAGCACAAGAAGCT
GTCTCTACCAAAGGAAGCTCCTTTGAGAATTTTGGAGGATTGTTGGACGA
AGTTGTGAACTTTGGATAA

Figure 6c

MAKPSQPTRDSHVAVLVFPFGTHAAPLLAVTCRLATAAPSTVFSFFSTARSNS
SLLSSDIPTNIRVHNVDDGVPEGFVLTGNPQHAVELFLEAAPEIFRREIKAAET
EVGRKFKCILTDAFLWLAAETAAAEMKASWVAYYGGGATSLTAHLYTDAIR
ENVGVKEVGERMEETIGFISGMEKIRVKDTQEGVVFGNLDSVFSKTLHQMGL
ALPRATAVFINSFEELDPTFTNDFRSEFKRYLNIGPLALLSSPSQTSTLVHDPHG
CLAWIEKRSTASVAYIAFGRVATPPPVELVAIAQGLESSKVPFVWSLQEMKM
THLPEGFLDRTREQGMVVPWAPQVELLNHEAMGVFVSHGGWNSVLESVSA
GVPMICRPIFGDHAINARSVEAVWEIGVTISSGVFTKDGFEESLDRVLVQDDG
KKMKVNAKKLEELAQEAVSTKGSSFENFGGLLDEVVNFG

Figure 7a

ATGGCAGAGATTCGCCAGAGAAGAGTGTTGATGGTCCCAGCACCGTTCCA
AGGCCATTTACCTTCGATGATGAATCTAGCGTCCTACCTTTCTTCCCAAGG
CTTTTCAATCACAATCGTTAGAAACGAATTCAATTTCAAAGATATCTCCCA
TAATTTCCCTGGTATAAAATTCTTCACCATCAAGGACGGCTTGTCAGAATC
TGACGTGAAGTCTCTGGGTCTCCTTGAATTTGTCCTGGAGCTTAACTCTGT
CTGTGAACCCCTATTGAAAGAGTTTCTAACCAACCATGATGATGTTGTTGA
CTTTATCATTTATGATGAATTTGTTTACTTCCCTCGACGTGTTGCGGAAGAT
ATGAATCTGCCAAAGATGGTCTTTAGCCCTTCTTCCGCCGCTACCTCGATC
AGCCGGTGTGTGCTTATGGAGAACCAATCAAATGGGTTACTTCCTCCACA
AGGTACCATGCTTACTTTTTTACTTGGGTTTTTTCAACTAGCAAATTTTG
ATGTATTTAATTTATTGTTTAACTTTTATAAACTACTATGTTAGTTTATTAA
TTTAGAATAAGGTTTTGGTTAAATATACAAGTTAAAGAAATATTATTCTTG
TAAGGATCAATTTTGTAGCATTGGCAGTAGACTCTGTTTTTTTCAACATTT
AAAACGTTTTACTGTATTTTGGTGATTTGGGTCTATTTCTATGACAGACGC
AAGATCTCAACTAGAAGAAACGGTGCCAGAGTTTCATCCCTTTCGTTTCA
AAGATCTGCCTTTTACAGCTTATGGATCTATGGAGAGATTAATGATACTTT
ACGAGAATGTAAGCAATAGAGCCTCATCTTCTGGCATAATACACAACTCT
TCGGATTGCTTAGAGAACTCATTCATAACAACTGCACAAGAGAAATGGGG
AGTTCCGGTATACCCGGTTGGTCCACTCCATATGACCAATTCCGCAATGTC
ATGTCCAAGTTTATTTGAAGAAGAAAGAAACTGTCTTGAATGGCTTGAGA
AGCAAGAAACAAGCTCAGTGATCTACATAAGCATGGGGAGCTTGGCGAT
GACACAAGATATAGAGGCTGTGGAGATGGCCATGGGATTTGTCCAGAGTA
ATCAACCCTTCTTGTGGGTGATCCGACCAGGCTCTATAAACGGACAAGAA
TCTTTAGACTTCTTACCGGAACAGTTCAACCAAACGGTGACCGATGGAAG
AGGTTTTGTTGTGAAATGGGCCCCACAAAAAGAGGTATTAAGGCATAGAG
CAGTGGGAGGGTTTTGGAACCATGGTGGATGGAACTCGTGCTTGGAGAGC
ATAAGCAGTGGTGTACCAATGATTTGTAGGCCGTATTCTGGTGATCAGAG
GGTGAATACTCGACTTATGTCACATGTTTGGCAAACCGCGTATGAGATCG
AAGGTGAATTGGAAAGAGGAGCTGTTGAGATGGCCGTGAGGAGGCTCATT
GTGGATCAAGAAGGTCAGGAGATGAGAATGAGAGCCACCATATTGAAGG
AAGAGGTTGAAGCCTCTGTCACAACCGAAGGCTCTTCTCACAATTCTTTAA
ACAATTTGGTCCATGCAATAATGATGCAAATTGACGAACAATGA

Figure 7b

ATGGCAGAGATTCGCCAGAGAAGAGTGTTGATGGTCCCAGCACCGTTCCA
AGGCCATTTACCTTCGATGATGAATCTAGCGTCCTACCTTTCTTCCCAAGG
CTTTTCAATCACAATCGTTAGAAACGAATTCAATTTCAAAGATATCTCCCA
TAATTTCCCTGGTATAAAATTCTTCACCATCAAGGACGGCTTGTCAGAATC
TGACGTGAAGTCTCTGGGTCTCCTTGAATTTGTCCTGGAGCTTAACTCTGT
CTGTGAACCCCTATTGAAAGAGTTTCTAACCAACCATGATGATGTTGTTGA
CTTTATCATTTATGATGAATTTGTTTACTTCCCTCGACGTGTTGCGGAAGAT
ATGAATCTGCCAAAGATGGTCTTTAGCCCTTCTTCCGCCGCTACCTCGATC
AGCCGGTGTGTGCTTATGGAGAACCAATCAAATGGGTTACTTCCTCCACA
AGACGCAAGATCTCAACTAGAAGAAACGGTGCCAGAGTTTCATCCCTTTC
GTTTCAAAGATCTGCCTTTTACAGCTTATGGATCTATGGAGAGATTAATGA
TACTTTACGAGAATGTAAGCAATAGAGCCTCATCTTCTGGCATAATACAC
AACTCTTCGGATTGCTTAGAGAACTCATTCATAACAACTGCACAAGAGAA
ATGGGGAGTTCCGGTATACCCGGTTGGTCCACTCCATATGACCAATTCCGC
AATGTCATGTCCAAGTTTATTTGAAGAAGAAAGAAACTGTCTTGAATGGC
TTGAGAAGCAAGAAACAAGCTCAGTGATCTACATAAGCATGGGGAGCTTG
GCGATGACACAAGATATAGAGGCTGTGGAGATGGCCATGGGATTTGTCCA
GAGTAATCAACCCTTCTTGTGGGTGATCCGACCAGGCTCTATAAACGGAC
AAGAATCTTTAGACTTCTTACCGGAACAGTTCAACCAAACGGTGACCGAT
GGAAGAGGTTTTGTTGTGAAATGGGCCCCACAAAAAGAGGTATTAAGGCA
TAGAGCAGTGGGAGGGTTTTGGAACCATGGTGGATGGAACTCGTGCTTGG
AGAGCATAAGCAGTGGTGTACCAATGATTTGTAGGCCGTATTCTGGTGAT
CAGAGGGTGAATACTCGACTTATGTCACATGTTTGGCAAACCGCGTATGA
GATCGAAGGTGAATTGGAAAGAGGAGCTGTTGAGATGGCCGTGAGGAGG
CTCATTGTGGATCAAGAAGGTCAGGAGATGAGAATGAGAGCCACCATATT
GAAGGAAGAGGTTGAAGCCTCTGTCACAACCGAAGGCTCTTCTCACAATT
CTTTAAACAATTTGGTCCATGCAATAATGATGCAAATTGACGAACAATGA

Figure 7c

MAEIRQRRVLMVPAPFQGHLPSMMNLASYLSSQGFSITIVRNEFNFKDISHNF
PGIKFFTIKDGLSESDVKSLGLLEFVLELNSVCEPLLKEFLTNHDDVVDFIIYDE
FVYFPRRVAEDMNLPKMVFSPSSAATSISRCVLMENQSNGLLPPQDARSQLEE
TVPEFHPFRFKDLPFTAYGSMERLMILYENVSNRASSSGIIHNSSDCLENSFITT
AQEKWGVPVYPVGPLHMTNSAMSCPSLFEEERNCLEWLEKQETSSVIYISMG
SLAMTQDIEAVEMAMGFVQSNQPFLWVIRPGSINGQESLDFLPEQFNQTVTD
GRGFVVKWAPQKEVLRHRAVGGFWNHGGWNSCLESISSGVPMICRPYSGDQ
RVNTRLMSHVWQTAYEIEGELERGAVEMAVRRLIVDQEGQEMRMRATILKE
EVEASVTTEGSSHNSLNNLVHAIMMQIDEQ

Figure 8a

ATGGAGGAAAAGCAAGTGAAGGAGACAAGGATAGTGTTGGTTCCAGTTC
CAGCTCAAGGTCATGTAACTCCGATGATGCAACTAGGAAAAGCTCTTCAC
TCAAAGGGTTTCTCCATCACTGTTGTTCTGACACAGTCTAATCGAGTTAGC
TCTTCCAAAGACTTCTCTGATTTCCATTTCCTCACCATCCCAGGCAGCTTA
ACTGAGTCTGATCTCCAAAACCTAGGACCACAAAAGTTTGTGCTCAAGCT
CAATCAAATTTGTGAGGCAAGCTTCAAGCAGTGTATAGGTCAACTATTGC
ATGAACAATGTAATAATGATATTGCTTGTGTCGTCTACGATGAGTACATGT
ACTTCTCTCATGCTGCAGTAAAAGAGTTTCAACTTCCTAGTGTCGTCTTTA
GCACGACAAGTGCTACTGCTTTTGTCTGTCGCTCTGTTTTGTCTAGAGTCA
ACGCAGAGTCGTTCTTGATCGACATGAAAGGTATTCAAGATTCTAGCTTGT
TTTATCTTAATTCAAAATCCTATTTATAGAAACTAATCCAAATGATCGATG
TTATCTTTTCAGATCCTGAAACACAAGACAAAGTATTTCCAGGGTTGCATC
CTCTGAGGTACAAGGATCTACCAACTTCAGTATTTGGGCCAATAGAGAGT
ACGCTCAAGGTTTACAGTGAGACTGTGAACACTCGAACAGCTTCCGCTGT
TATCATCAACTCAGCAAGCTGTTTAGAGAGCTCATCTTTGGCAAGGTTGCA
ACAACAACTGCAAGTTCCGGTGTATCCTATAGGCCCACTTCATATTACAGC
TTCAGCGCCTTCTAGTTTACTAGAAGAAGACAGGAGTTGCGTTGAGTGGTT
GAACAAGCAAAAATCAAATTCAGTTATTTACATAAGCTTGGGAAGCTTGG
CTCTAATGGACACCAAAGACATGTTGGAGATGGCTTGGGGATTAAGTAAT
AGCAACCAACCTTTCTTATGGGTGGTCAGACCGGGCTCTATTCCGGGGTC
AGAATGGACAGAGTCCTTACCAGAGGAATTCAATAGGTTGGTTTCAGAAA
GAGGTTACATTGTGAAATGGGCTCCGCAGATGGAAGTTCTCAGACATCCT
GCAGTAGGAGGGTTTTGGAGTCACTGTGGATGGAACTCAACAGTAGAGAG
CATCGGGGAAGGAGTTCCGATGATATGTAGGCCTTTCACCGGGGATCAGA
AAGTCAATGCGAGGTACTTAGAGAGTTTGGAGAATTGGGGTTCAATTG
GAGGGAGATCTGGATAAAGAAACTGTGGAGAGAGCTGTAGAGTGGTTGC
TTGTGGATGAAGAAGGAGCAGAAATGAGGAAGAGAGCCATTGACTTGAA
AGAAAAGATTGAAACCTCTGTTAGAAGTGGAGGTTCCTCATGCAGCTCAC
TAGACGACTTTGTTAATTCCATGTGA

Figure 8b

ATGGAGGAAAAGCAAGTGAAGGAGACAAGGATAGTGTTGGTTCCAGTTC
CAGCTCAAGGTCATGTAACTCCGATGATGCAACTAGGAAAAGCTCTTCAC
TCAAAGGGTTTCTCCATCACTGTTGTTCTGACACAGTCTAATCGAGTTAGC
TCTTCCAAAGACTTCTCTGATTTCCATTTCCTCACCATCCCAGGCAGCTTA
ACTGAGTCTGATCTCCAAAACCTAGGACCACAAAAGTTTGTGCTCAAGCT
CAATCAAATTTGTGAGGCAAGCTTCAAGCAGTGTATAGGTCAACTATTGC
ATGAACAATGTAATAATGATATTGCTTGTGTCGTCTACGATGAGTACATGT
ACTTCTCTCATGCTGCAGTAAAAGAGTTTCAACTTCCTAGTGTCGTCTTTA
GCACGACAAGTGCTACTGCTTTTGTCTGTCGCTCTGTTTTGTCTAGAGTCA
ACGCAGAGTCGTTCTTGATCGACATGAAAGATCCTGAAACACAAGACAAA
GTATTTCCAGGGTTGCATCCTCTGAGGTACAAGGATCTACCAACTTCAGTA
TTTGGGCCAATAGAGAGTACGCTCAAGGTTTACAGTGAGACTGTGAACAC
TCGAACAGCTTCCGCTGTTATCATCAACTCAGCAAGCTGTTTAGAGAGCTC
ATCTTTGGCAAGGTTGCAACAACAACTGCAAGTTCCGGTGTATCCTATAG
GCCCACTTCATATTACAGCTTCAGCGCCTTCTAGTTTACTAGAAGAAGACA
GGAGTTGCGTTGAGTGGTTGAACAAGCAAAAATCAAATTCAGTTATTTAC
ATAAGCTTGGGAAGCTTGGCTCTAATGGACACCAAAGACATGTTGGAGAT
GGCTTGGGGATTAAGTAATAGCAACCAACCTTTCTTATGGGTGGTCAGAC
CGGGCTCTATTCCGGGGTCAGAATGGACAGAGTCCTTACCAGAGGAATTC
AATAGGTTGGTTTCAGAAAGAGGTTACATTGTGAAATGGGCTCCGCAGAT
GGAAGTTCTCAGACATCCTGCAGTAGGAGGGTTTTGGAGTCACTGTGGAT
GGAACTCAACAGTAGAGAGCATCGGGGAAGGAGTTCCGATGATATGTAG
GCCTTTCACCGGGGATCAGAAAGTCAATGCGAGGTACTTAGAGAGTTT
GGAGAATTGGGGTTCAATTGGAGGGAGATCTGGATAAAGAAACTGTGGA
GAGAGCTGTAGAGTGGTTGCTTGTGGATGAAGAAGGAGCAGAAATGAGG
AAGAGAGCCATTGACTTGAAAGAAAGATTGAAACCTCTGTTAGAAGTGG
AGGTTCCTCATGCAGCTCACTAGACGACTTTGTTAATTCCATGTGA

Figure 8c

MEEKQVKETRIVLVPVPAQGHVTPMMQLGKALHSKGFSITVVLTQSNRVSSS
KDFSDFHFLTIPGSLTESDLQNLGPQKFVLKLNQICEASFKQCIGQLLHEQCNN
DIACVVYDEYMYFSHAAVKEFQLPSVVFSTTSATAFVCRSVLSRVNAESFLID
MKDPETQDKVFPGLHPLRYKDLPTSVFGPIESTLKVYSETVNTRTASAVIINSA
SCLESSSLARLQQQLQVPVYPIGPLHITASAPSSLLEEDRSCVEWLNKQKSNSV
IYISLGSLALMDTKDMLEMAWGLSNSNQPFLWVVRPGSIPGSEWTESLPEEFN
RLVSERGYIVKWAPQMEVLRHPAVGGFWSHCGWNSTVESIGEGVPMICRPFT
GDQKVNARYLERVWRIGVQLEGDLDKETVERAVEWLLVDEEGAEMRKRAI
DLKEKIETSVRSGGSSCSSLDDFVNSM

Figure 9a

ATGGAGAAGAGAAACGAGAGACAAGTGATTCTTTTTCCTCTACCATTACA
AGGTTGCATAAACCCTATGCTTCAGCTAGCAAAGATCCTTTACTCAAGAG
GTTTTTCGATCACCATCATCCACACGCGCTTCAACGCGCCCAAATCTTCAG
ACCATCCTCTCTTCACTTTCTTACAAATCCGCGACGGCTTGTCTGAATCTC
AGACTCAATCTCGTGATCTTTTGCTTCAACTCACGCTTCTCAACAACAATT
GTCAGATCCCATTTCGAGAGTGTTTGGCTAAACTCATTAAACCTAGTTCAG
ATTCAGGAACAGAGGATAGGAAAATTAGCTGTGTGATCGATGATTCCGGT
TGGGTTTTCACACAATCCGTGGCGGAGAGTTTTAATCTTCCTCGATTTGTC
CTCTGTGCTTATAAGTTCTCTTTCTTTCTCGGACATTTTCTTGTTCCTCAGA
TTCGTCGTGAAGGGTTTCTTCCAGTACCAGGTACGGCTTTGACTCATAGTA
GGTCATTGTTCTTATTGTTAATTGAGTCATCAAAGACACAATTGGTCCGTA
TTTCTTGAACTTTCTAGGTTTGTTTCAGATTCGGAGGCAGATGATCTAGTT
CCTGAGTTTCCACCGCTTCGAAAGAAAGATCTTTCGAGAATTATGGGAAC
CAGCGCTCAGAGTAAGCCTCTAGATGCTTACTTGCTTAAGATACTCGACG
CGACGAAGCCAGCTTCAGGGATTATAGTTATGTCCTGCAAAGAGCTTGAC
CATGATTCACTTGCTGAGTCCAACAAAGTTTTCAGCATTCCGATATTTCCC
ATTGGCCCTTTTCACATTCATGACGTCCCAGCCTCGTCTAGCAGCTTGTTA
GAACCGGACCAGAGTTGCATTCCATGGTTAGATATGCGTGAAACGAGATC
AGTAGTCTACGTGAGCTTAGGGAGCATTGCGAGTCTTAACGAGTCTGACT
TCTTGGAGATTGCTTGTGGACTAAGAAACACCAACCAATCCTTCTTGTGGG
TTGTCCGGCCTGGTTCAGTCCATGGCAGAGATTGGATCGAATCATTACCTT
CAGGGTTCATGGAAAGTCTCGATGGTAAAGGAAAGATAGTGAGATGGGC
ACCGCAGCTAGACGTTCTTGCGCATAGAGCCACGGGAGGGTTTTGACTC
ATAATGGATGGAACTCGACATTAGAGAGTATATGCGAAGGAGTACCTATG
ATCTGCTTGCCTTGTAAGTGGGACCAATTTGTAAACGCGAGATTCATAAG
CGAAGTTTGGAGGGTTGGGATTCACTTGGAAGGTCGGATAGAGCGAAGAG
AAATCGAGAGAGCTGTTATAAGACTAATGGTTGAGTCGAAAGGAGAAGA
GATTCGAGGTAGAATCAAAGTCTTGCGAGACGAAGTAAGAAGGTCAGTTA
AACAAGGAGGTTCGTCATATCGATCTTTAGATGAGTTGGTTGATCGTATAT
CAATCATCATCGAGCCACTAGTGCCTACGTGA

Figure 9b

ATGGAGAAGAGAAACGAGAGACAAGTGATTCTTTTTCCTCTACCATTACA
AGGTTGCATAAACCCTATGCTTCAGCTAGCAAAGATCCTTTACTCAAGAG
GTTTTTCGATCACCATCATCCACACGCGCTTCAACGCGCCCAAATCTTCAG
ACCATCCTCTCTTCACTTTCTTACAAATCCGCGACGGCTTGTCTGAATCTC
AGACTCAATCTCGTGATCTTTGCTTCAACTCACGCTTCTCAACAACAATT
GTCAGATCCCATTTCGAGAGTGTTTGGCTAAACTCATTAAACCTAGTTCAG
ATTCAGGAACAGAGGATAGGAAAATTAGCTGTGATCGATGATTCCGGT
TGGGTTTTCACACAATCCGTGGCGGAGAGTTTTAATCTTCCTCGATTTGTC
CTCTGTGCTTATAAGTTCTCTTTCTTTCTCGGACATTTTCTTGTTCCTCAGA
TTCGTCGTGAAGGGTTTCTTCCAGTACCAGATTCGGAGGCAGATGATCTA
GTTCCTGAGTTTCCACCGCTTCGAAAGAAAGATCTTTCGAGAATTATGGG
AACCAGCGCTCAGAGTAAGCCTCTAGATGCTTACTTGCTTAAGATACTCG
ACGCGACGAAGCCAGCTTCAGGGATTATAGTTATGTCCTGCAAAGAGCTT
GACCATGATTCACTTGCTGAGTCCAACAAAGTTTTCAGCATTCCGATATTT
CCCATTGGCCCTTTTCACATTCATGACGTCCCAGCCTCGTCTAGCAGCTTG
TTAGAACCGGACCAGAGTTGCATTCCATGGTTAGATATGCGTGAAACGAG
ATCAGTAGTCTACGTGAGCTTAGGGAGCATTGCGAGTCTTAACGAGTCTG
ACTTCTTGGAGATTGCTTGTGGACTAAGAAACACCAACCAATCCTTCTTGT
GGGTTGTCCGGCCTGGTTCAGTCCATGGCAGAGATTGGATCGAATCATTA
CCTTCAGGGTTCATGGAAAGTCTCGATGGTAAAGGAAAGATAGTGAGATG
GGCACCGCAGCTAGACGTTCTTGCGCATAGAGCCACGGGAGGGTTTTTGA
CTCATAATGGATGGAACTCGACATTAGAGAGTATATGCGAAGGAGTACCT
ATGATCTGCTTGCCTTGTAAGTGGGACCAATTTGTAAACGCGAGATTCATA
AGCGAAGTTTGGAGGGTTGGGATTCACTTGGAAGGTCGGATAGAGCGAAG
AGAAATCGAGAGAGCTGTTATAAGACTAATGGTTGAGTCGAAAGGAGAA
GAGATTCGAGGTAGAATCAAAGTCTTGCGAGACGAAGTAAGAAGGTCAG
TTAAACAAGGAGGTTCGTCATATCGATCTTTAGATGAGTTGGTTGATCGTA
TATCAATCATCATCGAGCCACTAGTGCCTACGTGA

Figure 9c

MEKRNERQVILFPLPLQGCINPMLQLAKILYSRGFSITIHTRFNAPKSSDHPLF
TFLQIRDGLSESQTQSRDLLLQLTLLNNNCQIPFRECLAKLIKPSSDSGTEDRKI
SCVIDDSGWVFTQSVAESFNLPRFVLCAYKFSFFLGHFLVPQIRREGFLPVPDS
EADDLVPEFPPLRKKDLSRIMGTSAQSKPLDAYLLKILDATKPASGIIVMSCKE
LDHDSLAESNKVFSIPIFPIGPFHIHDVPASSSSLLEPDQSCIPWLDMRETRSVV
YVSLGSIASLNESDFLEIACGLRNTNQSFLWVVRPGSVHGRDWIESLPSGFME
SLDGKGKIVRWAPQLDVLAHRATGGFLTHNGWNSTLESICEGVPMICLPCKW
DQFVNARFISEVWRVGIHLEGRIERREIERAVIRLMVESKGEEIRGRIKVLRDE
VRRSVKQGGSSYRSLDELVDRISIIIEPLVPT

Figure 10a

ATGGAGGAGAAGAGAAATGGTCTGCGTGTGATTCTCTTCCCTCTTCCATTACAAG
GTTGCATCAACCCTATGCTTCAGCTCGCCAACATCCTTCACGTAAGAGGCTTCTCC
ATTACCGTGATCCACACGCGCTTCAACGCGCCAAAAGCTTCAAGCCATCCTCTCT
TCACTTTCTTACAGATTCCTGATGGTTTGTCTGAAACGGAGATTCAAGATGGTGTT
ATGTCTTGCTCGCGCAAATCAACCTTAACGCTGAGTCTCCGTTTCGTGATTGCTT
GCGTAAAGTGTTGCTGGAATCAAAAGAGTCAGAGAGGGTTACTTGTTTGATCGAT
GACTGTGGATGGCTCTTCACACAATCTGTTTCAGAGAGTTTGAAGCTTCCGAGGC
TCGTTCTCTGTACTTTTAAAGCCACTTTCTTCAATGCTTATCCGAGTCTTCCACTTA
TCCGAACCAAGGGATATCTTCCAGTTTCAGGTAATTAATGCTTCATGAAATGCTT
ATTTTTAATGGTCAAATTGCTATATAGGAAAAGTTATCTAACTTGGGTAGGAAA
TTCGTATTTTTGTAAACATATTTGCATACTGTGACTACAAATGCTCTTCGCACTCT
CACCTATGATGATGTCAGTCTATTAAAAGGAAAATGTGTCATCCAATAAAAATAA
GGAAAGTAAAATTTTTGCATTTGACCAAAATGGTATATTTGTATTTATTCATAATT
GTGTTGTTTTTTAAAAAAATGGCGTCATCTCTACTAATAAAATAGCATGGCATGT
CAATGAATATTGGTCTAACAAATAAAAAGTTAAAGTTGTTCACGTAACTAAGGAA
AAGAGTAGGATATTTAGGTTATTTACTATGGACACTCTATTTTGAATTCTGGTTAT
CAAGTTTATAAGATTGTTTTGAGCCTTTGTGTCTTAGAATCGGAAGCAGAGGACT
CTGTTCCTGAGTTCCCGCCGCTTCAAAAGAGAGATCTTTCAAAGGTTTTCGGGGA
GTTCGGAGAGAAACTCGATCCGTTCTTACATGCTGTAGTCGAAACGACAATAAGA
TCTTCAGGGTTAATATACATGTCCTGCGAAGAGCTTGAGAAAGATTCGTTGACTC
TTTCTAACGAAATTTTTAAAGTTCCGGTTTTTGCAATTGGTCCGTTTCACAGCTAC
TTCTCTGCTTCGTCAAGCAGCTTGTTCACACAAGACGAGACTTGCATTCTGTGGTT
AGATGATCAAGAAGATAAATCTGTGATCTACGTTAGTCTAGGAAGCGTTGTGAAC
ATAACGGAAACAGAGTTCTTGGAGATTGCGTGTGGTTTAAGCAATAGCAAACAG
CCTTTCTTGTGGGTAGTACGACCCGGTTCAGTACTCGGCGCGAAATGGATCGAAC
CGCTCTCTGAAGGGCTGGTTAGTAGCCTTGAAGAGAAAGGAAAGATTGTGAAAT
GGGCACCACAACAGGAGGTTCTTGCGCATCGTGCCACAGGAGGGTTTTGACACA
CAATGGTTGGAACTCAACGCTAGAGAGTATATGCGAAGGGGTTCCTATGATCTGC
CTACCAGGAGGTTGGGATCAAATGCTGAATTCAAGATTTGTTAGCGATATTTGGA
AGATTGGAATTCACTTGGAAGGTCGGATTGAAAAAAAGGAGATTGAGAAAGCTG
TGAGGGTGTTAATGGAGGAAAGTGAAGGAAATAAGATTCGTGAGAGAATGAAAG
TTCTGAAAGATGAGGTCGAGAAATCGGTCAAACAAGGAGGCTCATCTTTTCAATC
TATTGAGACTCTAGCTAATCATATACTATTGTTGTAA

Figure 10b

ATGGAGGAGAAGAGAAATGGTCTGCGTGTGATTCTCTTCCCTCTTCCATTA
CAAGGTTGCATCAACCCTATGCTTCAGCTCGCCAACATCCTTCACGTAAGA
GGCTTCTCCATTACCGTGATCCACACGCGCTTCAACGCGCCAAAAGCTTCA
AGCCATCCTCTCTTCACTTTCTTACAGATTCCTGATGGTTTGTCTGAAACG
GAGATTCAAGATGGTGTTATGTCTTTGCTCGCGCAAATCAACCTTAACGCT
GAGTCTCCGTTTCGTGATTGCTTGCGTAAAGTGTTGCTGGAATCAAAAGAG
TCAGAGAGGGTTACTTGTTTGATCGATGACTGTGGATGGCTCTTCACACAA
TCTGTTTCAGAGAGTTTGAAGCTTCCGAGGCTCGTTCTCTGTACTTTTAAA
GCCACTTTCTTCAATGCTTATCCGAGTCTTCCACTTATCCGAACCAAGGGA
TATCTTCCAGTTTCAGAATCGGAAGCAGAGGACTCTGTTCCTGAGTTCCCG
CCGCTTCAAAAGAGAGATCTTTCAAAGGTTTTCGGGGAGTTCGGAGAGAA
ACTCGATCCGTTCTTACATGCTGTAGTCGAAACGACAATAAGATCTTCAG
GGTTAATATACATGTCCTGCGAAGAGCTTGAGAAAGATTCGTTGACTCTTT
CTAACGAAATTTTTAAAGTTCCGGTTTTTGCAATTGGTCCGTTTCACAGCT
ACTTCTCTGCTTCGTCAAGCAGCTTGTTCACACAAGACGAGACTTGCATTC
TGTGGTTAGATGATCAAGAAGATAAATCTGTGATCTACGTTAGTCTAGGA
AGCGTTGTGAACATAACGGAAACAGAGTTCTTGGAGATTGCGTGTGGTTT
AAGCAATAGCAAACAGCCTTTCTTGTGGGTAGTACGACCCGGTTCAGTAC
TCGGCGCGAAATGGATCGAACCGCTCTCTGAAGGGCTGGTTAGTAGCCTT
GAAGAGAAAGGAAAGATTGTGAAATGGGCACCACAACAGGAGGTTCTTG
CGCATCGTGCCACAGGAGGGTTTTTGACACACAATGGTTGGAACTCAACG
CTAGAGAGTATATGCGAAGGGGTTCCTATGATCTGCCTACCAGGAGGTTG
GGATCAAATGCTGAATTCAAGATTTGTTAGCGATATTTGGAAGATTGGAA
TTCAGTTGGAAGGTCGGATTGAAAAAAAGGAGATTGAGAAAGCTGTGAG
GGTGTTAATGGAGGAAAGTGAAGGAAATAAGATTCGTGAGAGAATGAAA
GTTCTGAAAGATGAGGTCGAGAAATCGGTCAAACAAGGAGGCTCATCTTT
TCAATCTATTGAGACTCTAGCTAATCATATACTATTGTTGTAA

Figure 10c

MEEKRNGLRVILFPLPLQGCINPMLQLANILHVRGFSITVIHTRFNAPKASSHP
LFTFLQIPDGLSETEIQDGVMSLLAQINLNAESPFRDCLRKVLLESKESERVTC
LDDCGWLFTQSVSESLKLPRLVLCTFKATFFNAYPSLPLIRTKGYLPVSESEA
EDSVPEFPPLQKRDLSKVFGEFGEKLDPFLHAVVETTIRSSGLIYMSCEELEKD
SLTLSNEIFKVPVFAIGPFHSYFSASSSSLFTQDETCILWLDDQEDKSVIYVSLG
SVVNITETEFLEIACGLSNSKQPFLWVVRPGSVLGAKWIEPLSEGLVSSLEEKG
KIVKWAPQQEVLAHRATGGFLTHNGWNSTLESICEGVPMICLPGGWDQMLN
SRFVSDIWKIGIHLEGRIEKKEIEKAVRVLMEESEGNKIRERMKVLKDEVEKS
VKQGGSSFQSIETLANHILLL

Figure 11a

ATGGTTTCCGAAACAACCAAATCTTCTCCACTTCACTTTGTTCTCTTCCCTT
TCATGGCTCAAGGCCACATGATTCCATGGTTGATATTGCAAGGCTCTTGG
CTCAGCGTGGTGTGATCATAACAATTGTCACGACGCCTCACAATGCAGCG
AGGTTCAAGAATGTCCTAAACCGTGCCATTGAGTCTGGCTTGCCCATCAA
CTTAGTGCAAGTCAAGTTTCCATATCTAGAAGCTGGTTTGCAAGAAGGAC
AAGAGAATATCGATTCTCTTGACACAATGGAGCGGATGATACCTTTCTTTA
AAGCGGTTAACTTTCTCGAAGAACCAGTCCAGAAGCTCATTGAAGAGATG
AACCCTCGACCAAGCTGTCTAATTTCTGATTTTTGTTTGCCTTATACAAGC
AAAATCGCCAAGAAGTTCAATATCCCAAAGATCCTCTTCCATGGCATGGG
TTGCTTTTGTCTTCTGTGTATGCATGTTTTACGCAAGAACCGTGAGATCTTG
GACAATTTAAAGTCAGATAAGGAGCTTTTCACTGTTCCTGATTTTCCTGAT
AGAGTTGAATTCACAAGAACGCAAGTTCCGGTAGAAACATATGTTCCAGC
TGGAGACTGGAAAGATATCTTTGATGGTATGGTAGAAGCGAATGAGACAT
CTTATGGTGTGATCGTCAACTCATTTCAAGAGCTCGAGCCTGCTTATGCCA
AAGACTACAAGGAGGTAAGGTCCGGTAAAGCATGGACCATTGGACCCGTT
TCCTTGTGCAACAAGGTAGGAGCCGACAAAGCAGAGAGGGGAAACAAAT
CAGACATTGATCAAGATGAGTGCCTTAAATGGCTCGATTCTAAGAAACAT
GGCTCGGTGCTTTACGTTTGTCTTGGAAGTATCTGTAATCTTCCTTTGTCTC
AACTCAAGGAGCTGGGACTAGGCCTAGAGGAATCCCAAAGACCTTTCATT
TGGGTCATAAGAGGTTGGGAGAAGTACAAAGAGTTAGTTGAGTGGTTCTC
GGAAAGCGGCTTTGAAGATAGAATCCAAGATAGAGGACTTCTCATCAAAG
GATGGTCCCCTCAAATGCTTATCCTTTCACATCCATCAGTTGGAGGGTTCC
TAACACACTGTGGTTGGAACTCGACTCTTGAGGGGATAACTGCTGGTCTA
CCGCTACTTACATGGCCGCTATTCGCAGACCAATTCTGCAATGAGAAATT
GGTCGTTGAGGTACTAAAAGCCGGTGTAAGATCCGGGGTTGAACAGCCTA
TGAAATGGGGAGAAGAGGAGAAAATAGGAGTGTTGGTGGATAAAGAAGG
AGTGAAGAAGGCAGTGGAAGAATTAATGGGTGAGAGTGATGATGCAAAA
GAGAGAAGAAGAAGAGCCAAGAGCTTGGAGATTCAGCTCACAAGGCTG
TGGAAGAAGGAGGCTCTTCTCATTCTAACATCTCTTTCTTGCTACAAGACA
TAATGGAACTGGCAGAACCCAATAATTGA

Figure 11b

MVSETTKSSPLHFVLFPFMAQGHMIPMVDIARLLAQRGVIITIVTTPHNAARF
KNVLNRAIESGLPINLVQVKFPYLEAGLQEGQENIDSLDTMERMIPFFKAVNF
LEEPVQKLIEEMNPRPSCLISDFCLPYTSKIAKKFNIPKILFHGMGCFCLLCMH
VLRKNREILDNLKSDKELFTVPDFPDRVEFTRTQVPVETYVPAGDWKDIFDG
MVEANETSYGVIVNSFQELEPAYAKDYKEVRSGKAWTIGPVSLCNKVGADK
AERGNKSDIDQDECLKWLDSKKHGSVLYVCLGSICNLPLSQLKELGLGLEES
QRPFIWVIRGWEKYKELVEWFSESGFEDRIQDRGLLIKGWSPQMLILSHPSVG
GFLTHCGWNSTLEGITAGLPLLTWPLFADQFCNEKLVVEVLKAGVRSGVEQP
MKWGEEEKIGVLVDKEGVKKAVEELMGESDDAKERRRRAKELGDSAHKAV
EEGGSSHSNISFLLQDIMELAEPNN

Figure 12a

ATGGGATCTCAGATCATTCATAACTCACAAAAACCACATGTAGTTTGTGTTCCAT
ATCCGGCTCAAGGCCACATCAACCCTATGATGAGAGTGGCTAAACTCCTCCACGC
CAGAGGCTTCTACGTCACCTTCGTCAACACCGTCTACAACCACAATCGTTTCCTTC
GTTCTCGTGGGTCCAATGCCCTAGATGGACTTCCTTCGTTCCGATTTGAGTCCATT
GCTGACGGTCTACCAGAGACAGACATGGATGCCACGCAGGACATCACAGCTCTTT
GCGAGTCCACCATGAAGAACTGTCTCGCTCCGTTCAGAGAGCTTCTCCAGCGGAT
CAACGCTGGAGATAATGTTCCTCCGGTAAGCTGTATTGTATCTGACGGTTGTATG
AGCTTTACTCTTGATGTTGCGGAGGAGCTTGGAGTCCCGGAGGTTCTTTTTTGGAC
AACCAGTGGCTGTGCGTTCCTGGCTTATCTACACTTTTATCTCTTCATCGAGAAGG
GCTTATGTCCGCTAAAAGGTACGTATTCTTACATTGATTATTGATTTAAATGACGT
TATGATATTAAATTTAACGTAAGAACCCTTAAGACACCTCGAGCAGGGTGAGTTT
TTAATCTGAGATATATCGTTTGTATATTGGATAAAAAATATCCATTTAGCTACCAT
ATTTAGCGAAGCCATAGACTATCCTAATCGATCCACCCGCACGACGAGACCGGTC
AAGACTCAAGATGGTCATGTTGTAATATATACTCAATTTTATACAATTGTTACATT
GTAGCCTAGGTTTTGAGCATTACTAAATATATAGTATCAAGAGAAATGTCCATA
TTTTAATATATACATAACGTAATGAATGTTTGATATGTTTTTTATTTCGATGCGTT
TGCAGTTTTCTTGTAATATATATATTACAGTTTTCTTAGCCAAAAAAAAAATAAAT
AATTAGAGAAGATACATTGTTGATTTATTTTAAAGCATTGATATCTTTTTAACCTT
CCGCTTCCCCTATCCGCTGGTGAATTTTGAGTGACATTAAAGATTGAACAGAAAT
CCCATATTTTATTTTGTTAAGAGATGCGTAGATTCTTAACTTTGATTACAGTTTAA
AATCATGTTAAAGGAAATGATGATGTTCAAAATTCCATTTCGTATTTTACATAAA
TTTTGTTGTTAACTTATCTTAAAGTTATATGATATTTGCAAACGTCGTCTTTCTATG
ATTTTTATTATTAGTTTGAACGTAAACAAAATATATTTAATATTTGTGAAAAGGCT
TGAAAATTGTAAAGAGGGATTTTTAAATAGTAACAAATTTTAGGTGAACTATAG
CGTATATAAAGATAGGTTATTTATTTGTGTAAAGATTATCTGTTTGTATTGGTTC
CAATTTTTTTCGGTGACCTTTAATAACATAGATGCATCACACATGAACATTTGGTA
TGAAAACAAAAGATAACCAATATTGCCAAAAAAAAAGAAGGAGAGAGACGG
CGGGAAAGTTTGTTGAGGAAAAAAATAAAATTGGGTAATATCCAAACATGAAAG
TGAAATAAACCGTAAAAAATCAATGCAATTTGGCATATCATTGTCCAGGGACCAG
GCCACTCTGTCTTTCGGTCATATTCATAACTCTTTCTGGCTCTGAAATTACACAAT
GAATGCCGTGTCCTAGAGAATCATATAGACGTGGATGCTTACGTAAATGCATAAT
TTTTTCTAAAATGCGGTGCTTGTATTTTATTAACTAATATCATGAGACTTATCTT
GATTAATAAATGGTGATTGATTTGGCAGATGAGAGTTACTTGACGAAGGAGTACT

Figure 12a continued

TAGAAGACACGGTTATAGATTTTATACCAACCATGAAGAATGTGAAACTAAAGG
ATATTCCTAGCTTCATACGTACCACTAATCCTGATGATGTTATGATTAGTTTCGCC
CTCCGCGAGACCGAGCGAGCCAAACGTGCTTCTGCTATCATTCTAAACACATTTG
ATGACCTTGAGCATGATGTTGTTCATGCTATGCAATCTATCTTACCTCCGGTTTAT
TCAGTTGGACCGCTTCATCTCTTAGCAAACCGGGAGATTGAAGAAGGTAGTGAGA
TTGGAATGATGAGTTCGAATTTATGGAAAGAGGAGATGGAGTGTTTGGATTGGCT
TGATACTAAGACTCAAAATAGTGTCATTTATATCAACTTTGGGACCATAACGGTT
TTGAGTGTGAAGCAGCTTGTGGAGTTTGCTTGGGGTTTGGCGGGAAGTGGGAAAG
AGTTTTTATGGGTGATCCGGCCAGATTTAGTAGCGGGAGAGGAGGCTATGGTTCC
GCCGGACTTTTTAATGGAGACTAAAGACCGCAGTATGCTAGCGAGTTGGTGTCCT
CAAGAGAAAGTACTTTCTCATCCTGCTATTGGAGGGTTTTTGACGCATTGCGGGT
GGAACTCGATATTGGAAAGTCTTTCGTGTGGAGTTCCGATGGTGTGTTGGCCATT
TTTTGCTGACCAGCAAATGAATTGTAAGTTTTGTTGTGACGAGTGGGATGTTGGG
ATTGAGATAGGTGGAGATGTGAAGAGAGAGGAAGTTGAGGCGGTGGTTAGAGAG
CTCATGGATGGAGAGAAGGGAAAGAAAATGAGAGAAAAGGCGGTAGAGTGGCA
GCGCTTAGCCGAGAAAGCGACGGAACATAAACTTGGTTCTTCCGTTATGAATTTT
GAGACGGTTGTTAGCAAGTTTCTTTTGGGACAAAAATCACAGGATTAA

Figure 12b

ATGGGATCTCAGATCATTCATAACTCACAAAAACCACATGTAGTTTGTGTT
CCATATCCGGCTCAAGGCCACATCAACCCTATGATGAGAGTGGCTAAACT
CCTCCACGCCAGAGGCTTCTACGTCACCTTCGTCAACACCGTCTACAACCA
CAATCGTTTCCTTCGTTCTCGTGGGTCCAATGCCCTAGATGGACTTCCTTC
GTTCCGATTTGAGTCCATTGCTGACGGTCTACCAGAGACAGACATGGATG
CCACGCAGGACATCACAGCTCTTTGCGAGTCCACCATGAAGAACTGTCTC
GCTCCGTTCAGAGAGCTTCTCCAGCGGATCAACGCTGGAGATAATGTTCC
TCCGGTAAGCTGTATTGTATCTGACGGTTGTATGAGCTTTACTCTTGATGT
TGCGGAGGAGCTTGGAGTCCCGGAGGTTCTTTTTGGACAACCAGTGGCT
GTGCGTTCCTGGCTTATCTACACTTTTATCTCTTCATCGAGAAGGGCTTAT
GTCCGCTAAAAGATGAGAGTTACTTGACGAAGGAGTACTTAGAAGACACG
GTTATAGATTTTATACCAACCATGAAGAATGTGAAACTAAAGGATATTCC
TAGCTTCATACGTACCACTAATCCTGATGATGTTATGATTAGTTTCGCCCT
CCGCGAGACCGAGCGAGCCAAACGTGCTTCTGCTATCATTCTAAACACAT
TTGATGACCTTGAGCATGATGTTGTTCATGCTATGCAATCTATCTTACCTC
CGGTTTATTCAGTTGGACCGCTTCATCTCTTAGCAAACCGGGAGATTGAAG
AAGGTAGTGAGATTGGAATGATGAGTTCGAATTTATGGAAAGAGGAGATG
GAGTGTTTGGATTGGCTTGATACTAAGACTCAAAATAGTGTCATTTATATC
AACTTTGGGAGCATAACGGTTTTGAGTGTGAAGCAGCTTGTGGAGTTTGCT
TGGGGTTTGGCGGGAAGTGGGAAAGAGTTTTTATGGGTGATCCGGCCAGA
TTAGTAGCGGGAGAGGAGGCTATGGTTCCGCCGGACTTTTTAATGGAGA
CTAAAGACCGCAGTATGCTAGCGAGTTGGTGTCCTCAAGAGAAAGTACTT
TCTCATCCTGCTATTGGAGGGTTTTGACGCATTGCGGGTGGAACTCGATA
TTGGAAAGTCTTTCGTGTGGAGTTCCGATGGTGTGTTGGCCATTTTTTGCT
GACCAGCAAATGAATTGTAAGTTTTGTTGTGACGAGTGGGATGTTGGGAT
TGAGATAGGTGGAGATGTGAAGAGAGAGGAAGTTGAGGCGGTGGTTAGA
GAGCTCATGGATGGAGAGAAGGGAAAGAAAATGAGAGAAAGGCGGTA
GAGTGGCAGCGCTTAGCCGAGAAAGCGACGGAACATAAACTTGGTTCTTC
CGTTATGAATTTTGAGACGGTTGTTAGCAAGTTTCTTTTGGGACAAAAATC
ACAGGATTAA

Figure 12c

MGSQIHHNSQKPHVVCVPYPAQGHINPMMRVAKLLHARGFYVTFVNTVYNH
NRFLRSRGSNALDGLPSFRFESIADGLPETDMDATQDITALCESTMKNCLAPF
RELLQRINAGDNVPPVSCIVSDGCMSFTLDVAEELGVPEVLFWTTSGCAFLAY
LHFYLFIEKGLCPLKDESYLTKEYLEDTVIDFIPTMKNVKLKDIPSFIRTTNPDD
VMISFALRETERAKRASAIILNTFDDLEHDVVHAMQSILPPVYSVGPLHLLAN
REIEEGSEIGMMSSNLWKEEMECLDWLDTKTQNSVIYINFGSITVLSVKQLVE·
FAWGLAGSGKEFLWVIRPDLVAGEEAMVPPDFLMETKDRSMLASWCPQEKV
LSHPAIGGFLTHCGWNSILESLSCGVPMVCWPFFADQQMNCKFCCDEWDVGI
EIGGDVKREEVEAVVRELMDGEKGKKMREKAVEWQRLAEKATEHKLGSSV
MNFETVVSKFLLGQKSQD

SEQUENCE LISTING

<160> NUMBER OF SEQ ID NOS: 32

<210> SEQ ID NO 1
<211> LENGTH: 1443
<212> TYPE: DNA
<213> ORGANISM: Arabidopsis thaliana

<400> SEQUENCE: 1

```
atgaacaaat tgcgcttgt cttcgtacca tttcctatac ttggtcatct caaatcaacc      60
gccgagatgg ctaagctact agtggagcaa gaaactcgcc tctctatctc cattatcatc     120
cttcctcttc tttccggaga cgacgtcagt gcttccgctt atatctcagc tctttccgcc     180
gcatccaacg accgccttca ctatgaagtg atctcggacg gagatcaacc aaccgtcggg     240
ttacatgtcg ataaccacat cccgatggtg aaacgtaccg ttgcaaaact cgttgatgac     300
tactcaaggc ggccgactc gccgaggctc gctggtttag ttgttgacat gttttgtatc     360
tcggtgatag acgtggctaa tgaggttagt gttccgtgtt acttgtttta cacgtcaaac     420
```

-continued

```
gttgggattc ttgctcttgg gttacatatt cagatgttgt ttgataagaa ggagtacagt    480
gtcagtgaaa ctgattttga agactcggaa gttgtgttgg atgttccgag tttgacttgt    540
ccttatccgg tgaagtgtct tccttatggt ttggcaacga aagagtggct tcctatgtat    600
ctaaatcaag gtagaagatt cagagagatg aaaggtattt tggtaaatac ttttgctgag    660
cttgaacctt atgcgttgga gtctcttcac tctagtggtg atactcctcg tgcttatcca    720
gtgggaccat tgttgcatct cgagaaccat gttgacggtt ctaaagacga aagggttcg    780
gacattttac ggtggttaga tgaacaacca cctaaatcgg tagtgttcct ctgctttgga    840
agcataggag gctttaacga ggaacaagca agagaaatgg ccattgcact tgagagaagt    900
ggtcaccgct tcttgtggtc tcttcgccgt gcatctcgag atatagataa ggaacttccc    960
ggagaattca gaatcttga agaaattctc ccggaaggat tctttgatcg gacaaaggat    1020
aaaggaaagg tgatcggatg ggctccacaa gtagccgtgc tggctaagcc agcaatcgga    1080
ggttttgtta ctcattgcgg gtggaactcg atactcgaga gtctttggtt cggtgttcct    1140
atagcgccat ggccgttata cgctgagcag aagtttaatg ctttcgtgat ggtggaggag    1200
cttggtttgg cagtgaagat aagaaagtat tggcgaggcg atcagttggt gggaacggcg    1260
acggtcatag tgacggcaga ggagatagag agaggaatca gatgtttgat ggagcaagat    1320
agtgacgtga ggaatagagt gaaggagatg agtaagaaat gtcacatggc tttaaaggat    1380
ggtggctcgt ctcaatctgc tttgaaatta tttattcaag acgttacgaa gtatattgct    1440
tga                                                                   1443
```

<210> SEQ ID NO 2
<211> LENGTH: 480
<212> TYPE: PRT
<213> ORGANISM: Arabidopsis thaliana

<400> SEQUENCE: 2

```
Met Asn Lys Phe Ala Leu Val Phe Val Pro Phe Pro Ile Leu Gly His
1               5                   10                  15

Leu Lys Ser Thr Ala Glu Met Ala Lys Leu Leu Val Glu Gln Glu Thr
            20                  25                  30

Arg Leu Ser Ile Ser Ile Ile Leu Pro Leu Leu Ser Gly Asp Asp
        35                  40                  45

Val Ser Ala Ser Ala Tyr Ile Ser Ala Leu Ser Ala Ala Ser Asn Asp
    50                  55                  60

Arg Leu His Tyr Glu Val Ile Ser Asp Gly Asp Gln Pro Thr Val Gly
65                  70                  75                  80

Leu His Val Asp Asn His Ile Pro Met Val Lys Arg Thr Val Ala Lys
                85                  90                  95

Leu Val Asp Asp Tyr Ser Arg Arg Pro Asp Ser Pro Arg Leu Ala Gly
            100                 105                 110

Leu Val Val Asp Met Phe Cys Ile Ser Val Ile Asp Val Ala Asn Glu
        115                 120                 125

Val Ser Val Pro Cys Tyr Leu Phe Tyr Thr Ser Asn Val Gly Ile Leu
    130                 135                 140

Ala Leu Gly Leu His Ile Gln Met Leu Phe Asp Lys Lys Glu Tyr Ser
145                 150                 155                 160

Val Ser Glu Thr Asp Phe Glu Asp Ser Glu Val Val Leu Asp Val Pro
                165                 170                 175

Ser Leu Thr Cys Pro Tyr Pro Val Lys Cys Leu Pro Tyr Gly Leu Ala
            180                 185                 190
```

Thr Lys Glu Trp Leu Pro Met Tyr Leu Asn Gln Gly Arg Arg Phe Arg
          195                 200                 205

Glu Met Lys Gly Ile Leu Val Asn Thr Phe Ala Glu Leu Glu Pro Tyr
          210                 215                 220

Ala Leu Glu Ser Leu His Ser Ser Gly Asp Thr Pro Arg Ala Tyr Pro
225                 230                 235                 240

Val Gly Pro Leu Leu His Leu Glu Asn His Val Asp Gly Ser Lys Asp
                245                 250                 255

Glu Lys Gly Ser Asp Ile Leu Arg Trp Leu Asp Glu Gln Pro Pro Lys
            260                 265                 270

Ser Val Val Phe Leu Cys Phe Gly Ser Ile Gly Gly Phe Asn Glu Glu
        275                 280                 285

Gln Ala Arg Glu Met Ala Ile Ala Leu Glu Arg Ser Gly His Arg Phe
    290                 295                 300

Leu Trp Ser Leu Arg Arg Ala Ser Arg Asp Ile Asp Lys Glu Leu Pro
305                 310                 315                 320

Gly Glu Phe Lys Asn Leu Glu Glu Ile Leu Pro Glu Gly Phe Phe Asp
                325                 330                 335

Arg Thr Lys Asp Lys Gly Lys Val Ile Gly Trp Ala Pro Gln Val Ala
            340                 345                 350

Val Leu Ala Lys Pro Ala Ile Gly Gly Phe Val Thr His Cys Gly Trp
        355                 360                 365

Asn Ser Ile Leu Glu Ser Leu Trp Phe Gly Val Pro Ile Ala Pro Trp
    370                 375                 380

Pro Leu Tyr Ala Glu Gln Lys Phe Asn Ala Phe Val Met Val Glu Glu
385                 390                 395                 400

Leu Gly Leu Ala Val Lys Ile Arg Lys Tyr Trp Arg Gly Asp Gln Leu
                405                 410                 415

Val Gly Thr Ala Thr Val Ile Val Thr Ala Glu Glu Ile Glu Arg Gly
            420                 425                 430

Ile Arg Cys Leu Met Glu Gln Asp Ser Asp Val Arg Asn Arg Val Lys
        435                 440                 445

Glu Met Ser Lys Lys Cys His Met Ala Leu Lys Asp Gly Gly Ser Ser
    450                 455                 460

Gln Ser Ala Leu Lys Leu Phe Ile Gln Asp Val Thr Lys Tyr Ile Ala
465                 470                 475                 480

<210> SEQ ID NO 3
<211> LENGTH: 1431
<212> TYPE: DNA
<213> ORGANISM: Arabidopsis thaliana

<400> SEQUENCE: 3
atgaaagcag aagcagagat catcttcgtt acatatccat ccctggtca tcttcttgtc      60 tccattgaat tcgctaaatc tctcatcaaa cgtgatgatc gcatccacac catcaccatc     120
ctctactggg ctttacctct cgctcctcaa gcccaccttt tcgctaagtc cctcgttgct     180
tcacagcctc gaatccgtct ccttgcgttg cctgatgttc aaaaccctcc accattggaa     240
ctcttcttta aagctcccga agcttatatt cttgagtcca ccaagaaaac agttccttta     300
gtcagagacg ctctctccac tctagtttct tcacgtaaag aatccggttc ggttcgtgta     360
gtcggtttgg ttatcgattt tttttgtgtt ccaatgatcg aagtggcaaa cgagcttaac     420
cttccttctt acatcttcct aacgtgtaac gctgggtttt aagtatgat gaagtatctc     480

-continued

```
cctgagagac atcgcataac cacttctgag ctagatttaa gctccggcaa cgtagaacat    540
ccaattcctg gctacgtctg ctccgtgccg acgaaggttt tgcctccagg tctattcgtg    600
agagagtcct acgaggcttg ggtcgagatt gcagagaagt tccctggagc caagggcatt    660
ttggtaaact cagtcacatg tcttgagcag aatgcatttg attacttcgc tcgtcttgat    720
gagaactatc ctccggttta cccggtcgga ccggttctta gtttgaagga tcgtccgtct    780
ccaaatctgg acgcatcgga ccgggatcgg atcatgagat ggctcgagga ccagccggag    840
tcgtcaattg tgtatatctg cttcggaagc ctcggaatca ttggcaagct gcagattgaa    900
gagatagctg aagccttgga actcaccggc cacaggtttc tttggtcaat acgtacaaat    960
ccgacggaga aagcgagccc gtacgatctg ttgccggagg gatttctcga tcggacggcc   1020
agtaagggat tggtgtgtga ttgggccccg caagtagaag ttctggccca taaagcgctc   1080
ggaggattcg tgtctcactg cggttggaac tctgtactgg agagcttatg gttcggtgtt   1140
ccgatcgcca cgtggccaat gtacgctgag caacagttaa acgcattctc gatggtgaag   1200
gagttagggt tagccgtgga gctgcgttta gactacgttt cggcgtacgg agagatagta   1260
aaagctgagg agatcgcggg agccatacga tcattgatgg acggtgagga tacgccgagg   1320
aagagagtga aggagatggc ggaagcggcg aggaatgctt tgatggacgg aggatcttcg   1380
tttgttgcgg ttaaacgatt tctcgacgag ttgatcggcg agatgtttag              1431
```

<210> SEQ ID NO 4
<211> LENGTH: 476
<212> TYPE: PRT
<213> ORGANISM: Arabidopsis thaliana

<400> SEQUENCE: 4

```
Met Lys Ala Glu Ala Glu Ile Ile Phe Val Thr Tyr Pro Ser Pro Gly
1               5                   10                  15

His Leu Leu Val Ser Ile Glu Phe Ala Lys Ser Leu Ile Lys Arg Asp
            20                  25                  30

Asp Arg Ile His Thr Ile Thr Ile Leu Tyr Trp Ala Leu Pro Leu Ala
        35                  40                  45

Pro Gln Ala His Leu Phe Ala Lys Ser Leu Val Ala Ser Gln Pro Arg
    50                  55                  60

Ile Arg Leu Leu Ala Leu Pro Asp Val Gln Asn Pro Pro Leu Glu
65                  70                  75                  80

Leu Phe Phe Lys Ala Pro Glu Ala Tyr Ile Leu Glu Ser Thr Lys Lys
                85                  90                  95

Thr Val Pro Leu Val Arg Asp Ala Leu Ser Thr Leu Val Ser Ser Arg
            100                 105                 110

Lys Glu Ser Gly Ser Val Arg Val Gly Leu Val Ile Asp Phe Phe
        115                 120                 125

Cys Val Pro Met Ile Glu Val Ala Asn Glu Leu Asn Leu Pro Ser Tyr
    130                 135                 140

Ile Phe Leu Thr Cys Asn Ala Gly Phe Leu Ser Met Met Lys Tyr Leu
145                 150                 155                 160

Pro Glu Arg His Arg Ile Thr Thr Ser Glu Leu Asp Leu Ser Ser Gly
                165                 170                 175

Asn Val Glu His Pro Ile Pro Gly Tyr Val Cys Ser Val Pro Thr Lys
            180                 185                 190

Val Leu Pro Pro Gly Leu Phe Val Arg Glu Ser Tyr Glu Ala Trp Val
        195                 200                 205
```

| | | | | | | | | | | | |
|---|---|---|---|---|---|---|---|---|---|---|---|
|Glu|Ile|Ala|Glu|Lys|Phe|Pro|Gly|Ala|Lys|Gly|Ile|Leu|Val|Asn|Ser|
| |210| | | |215| | | |220| | | | | | |
|Val|Thr|Cys|Leu|Glu|Gln|Asn|Ala|Phe|Asp|Tyr|Phe|Ala|Arg|Leu|Asp|
|225| | | | |230| | | | |235| | | | |240|
|Glu|Asn|Tyr|Pro|Pro|Val|Tyr|Pro|Val|Gly|Pro|Val|Leu|Ser|Leu|Lys|
| | | | |245| | | | |250| | | | |255| |
|Asp|Arg|Pro|Ser|Pro|Asn|Leu|Asp|Ala|Ser|Asp|Arg|Asp|Arg|Ile|Met|
| | | |260| | | | |265| | | | |270| | |
|Arg|Trp|Leu|Glu|Asp|Gln|Pro|Glu|Ser|Ser|Ile|Val|Tyr|Ile|Cys|Phe|
| | |275| | | | |280| | | | |285| | | |
|Gly|Ser|Leu|Gly|Ile|Ile|Gly|Lys|Leu|Gln|Ile|Glu|Glu|Ile|Ala|Glu|
| |290| | | | |295| | | | |300| | | | |
|Ala|Leu|Glu|Leu|Thr|Gly|His|Arg|Phe|Leu|Trp|Ser|Ile|Arg|Thr|Asn|
|305| | | | |310| | | | |315| | | | |320|
|Pro|Thr|Glu|Lys|Ala|Ser|Pro|Tyr|Asp|Leu|Leu|Pro|Glu|Gly|Phe|Leu|
| | | | |325| | | | |330| | | | |335| |
|Asp|Arg|Thr|Ala|Ser|Lys|Gly|Leu|Val|Cys|Asp|Trp|Ala|Pro|Gln|Val|
| | | |340| | | | |345| | | | |350| | |
|Glu|Val|Leu|Ala|His|Lys|Ala|Leu|Gly|Gly|Phe|Val|Ser|His|Cys|Gly|
| | |355| | | | |360| | | | |365| | | |
|Trp|Asn|Ser|Val|Leu|Glu|Ser|Leu|Trp|Phe|Gly|Val|Pro|Ile|Ala|Thr|
| |370| | | | |375| | | | |380| | | | |
|Trp|Pro|Met|Tyr|Ala|Glu|Gln|Gln|Leu|Asn|Ala|Phe|Ser|Met|Val|Lys|
|385| | | | |390| | | | |395| | | | |400|
|Glu|Leu|Gly|Leu|Ala|Val|Gly|Leu|Arg|Leu|Asp|Tyr|Val|Ser|Ala|Tyr|
| | | | |405| | | | |410| | | | |415| |
|Gly|Glu|Ile|Val|Lys|Ala|Glu|Glu|Ile|Ala|Gly|Ala|Ile|Arg|Ser|Leu|
| | | |420| | | | |425| | | | |430| | |
|Met|Asp|Gly|Glu|Asp|Thr|Pro|Arg|Lys|Arg|Val|Lys|Glu|Met|Ala|Glu|
| | |435| | | | |440| | | | |445| | | |
|Ala|Ala|Arg|Asn|Ala|Leu|Met|Asp|Gly|Gly|Ser|Ser|Phe|Val|Ala|Val|
| |450| | | | |455| | | | |460| | | | |
|Lys|Arg|Phe|Leu|Asp|Glu|Leu|Ile|Gly|Gly|Asp|Val| | | | |
|465| | | | |470| | | | |475| | | | | |

```
<210> SEQ ID NO 5
<211> LENGTH: 1440
<212> TYPE: DNA
<213> ORGANISM: Arabidopsis thaliana

<400> SEQUENCE: 5
atggtgaagg aaacagagct aatcttcatt ccagttccat ccacaggtca tattctcgtc    60
catattgaat tcgccaagcg tctcatcaat ctcgaccatc ggatccacac catcactatt   120
ctcaacttat cctcaccctc ttctcctcac gcctccgtct tcgccagatc tctcatcgct   180
tcccagccca aaatccgtct ccacgacctt ccccctatcc aagatcctcc tccattcgat   240
ctttaccaaa gagctcccga agcttacata gtaaaactca tcaagaaaaa tactcctctg   300
ataaaagacg ccgtctccag catcgtcgcg tcgcgtcgtg gaggctcaga ttcggttcaa   360
gtcgccggtt tggttctcga tttattctgc aattcattgg taaagatgt tggcaacgag   420
cttaatcttc cttcttacat ataccttacg tgtaacgcta gatacttggg gatgatgaaa   480
tatattccgg atcggcatcg gaaaatcgca tctgagttcg atttgagctc cggcgatgaa   540
gaattgccgg ttccgggatt cataaacgct attccgacga aatttatgcc gcctggattg   600
```

-continued

```
ttcaataagg aagcttacga ggcttacgta gagctagcgc cgagattcgc agatgcgaag    660
ggtatttttgg ttaattcctt cacgagcttt gagccgcacc cgtttgacta tttctctcac   720
ctggagaaat tccctccggt ttacccggtc ggaccgattc tcagcttgaa agatcgagcg   780
agtccgaacg aagaagcagt cgatcgggat cagatcgttg gtggctcga tgatcagccg    840
gagtcatcgg tggtgttcct ctgtttcggg agcagaggaa cgttgatga ccgcaagtg     900
aaggagatag ctcgagcttt ggaactcgtc ggctgcagat ttctttggtc aattagaaca   960
agcggcgacg tcgagacgaa tcctaacgat gtgttgccgg aggggttcat gggccgagta   1020
gcaggccgag gtttggtatg tggttgggct ccacaagtgg aagtgttggc ccataaagca   1080
ataggaggat ttgtgtctca ctgtggttgg aactccacgc ttgaaagctt atggttcggg   1140
gttcctgtcg caacgtggcc gatgtacgca gagcaacagc ttaacgcctt cacgctggtg   1200
aaagagcttg gcttgcggt ggacctgcgg atggattacg tgtcgagtcg tgggggtttg    1260
gtgacttgtg atgagatagc cagagccgta cgatctttga tggacggtgg agatgagaag   1320
agaaaaaagg ttaaggagat ggctgatgcg gcaaggaagg ctttgatgga tggaggatcg   1380
tcttctttgg caactgctcg attcatcgca gaattgtttg aagatggttc gtcgtgctaa   1440
```

<210> SEQ ID NO 6
<211> LENGTH: 479
<212> TYPE: PRT
<213> ORGANISM: Arabidopsis thaliana

<400> SEQUENCE: 6

```
Met Val Lys Glu Thr Glu Leu Ile Phe Ile Pro Val Pro Ser Thr Gly
1               5                   10                  15

His Ile Leu Val His Ile Glu Phe Ala Lys Arg Leu Ile Asn Leu Asp
            20                  25                  30

His Arg Ile His Thr Ile Thr Ile Leu Asn Leu Ser Ser Pro Ser Ser
        35                  40                  45

Pro His Ala Ser Val Phe Ala Arg Ser Leu Ile Ala Ser Gln Pro Lys
    50                  55                  60

Ile Arg Leu His Asp Leu Pro Pro Ile Gln Asp Pro Pro Phe Asp
65                  70                  75                  80

Leu Tyr Gln Arg Ala Pro Glu Ala Tyr Ile Val Lys Leu Ile Lys Lys
                85                  90                  95

Asn Thr Pro Leu Ile Lys Asp Ala Val Ser Ser Ile Val Ala Ser Arg
            100                 105                 110

Arg Gly Gly Ser Asp Ser Val Gln Val Ala Gly Leu Val Leu Asp Leu
        115                 120                 125

Phe Cys Asn Ser Leu Val Lys Asp Val Gly Asn Glu Leu Asn Leu Pro
    130                 135                 140

Ser Tyr Ile Tyr Leu Thr Cys Asn Ala Arg Tyr Leu Gly Met Met Lys
145                 150                 155                 160

Tyr Ile Pro Asp Arg His Arg Lys Ile Ala Ser Glu Phe Asp Leu Ser
                165                 170                 175

Ser Gly Asp Glu Glu Leu Pro Val Pro Gly Phe Ile Asn Ala Ile Pro
            180                 185                 190

Thr Lys Phe Met Pro Pro Gly Leu Phe Asn Lys Glu Ala Tyr Glu Ala
        195                 200                 205

Tyr Val Glu Leu Ala Pro Arg Phe Ala Asp Ala Lys Gly Ile Leu Val
    210                 215                 220

Asn Ser Phe Thr Glu Leu Glu Pro His Pro Phe Asp Tyr Phe Ser His
```

```
                225                 230                 235                 240
Leu Glu Lys Phe Pro Pro Val Tyr Pro Val Gly Pro Ile Leu Ser Leu
                    245                 250                 255
Lys Asp Arg Ala Ser Pro Asn Glu Glu Ala Val Asp Arg Asp Gln Ile
                260                 265                 270
Val Gly Trp Leu Asp Asp Gln Pro Glu Ser Ser Val Val Phe Leu Cys
            275                 280                 285
Phe Gly Ser Arg Gly Ser Val Asp Glu Pro Gln Val Lys Glu Ile Ala
        290                 295                 300
Arg Ala Leu Glu Leu Val Gly Cys Arg Phe Leu Trp Ser Ile Arg Thr
305                 310                 315                 320
Ser Gly Asp Val Glu Thr Asn Pro Asn Asp Val Leu Pro Glu Gly Phe
                325                 330                 335
Met Gly Arg Val Ala Gly Arg Gly Leu Val Cys Gly Trp Ala Pro Gln
                340                 345                 350
Val Glu Val Leu Ala His Lys Ala Ile Gly Gly Phe Val Ser His Cys
            355                 360                 365
Gly Trp Asn Ser Thr Leu Glu Ser Leu Trp Phe Gly Val Pro Val Ala
        370                 375                 380
Thr Trp Pro Met Tyr Ala Glu Gln Gln Leu Asn Ala Phe Thr Leu Val
385                 390                 395                 400
Lys Glu Leu Gly Leu Ala Val Asp Leu Arg Met Asp Tyr Val Ser Ser
                405                 410                 415
Arg Gly Gly Leu Val Thr Cys Asp Glu Ile Ala Arg Ala Val Arg Ser
            420                 425                 430
Leu Met Asp Gly Gly Asp Glu Lys Arg Lys Val Lys Glu Met Ala
        435                 440                 445
Asp Ala Ala Arg Lys Ala Leu Met Asp Gly Gly Ser Ser Ser Leu Ala
    450                 455                 460
Thr Ala Arg Phe Ile Ala Glu Leu Phe Glu Asp Gly Ser Ser Cys
465                 470                 475

<210> SEQ ID NO 7
<211> LENGTH: 1479
<212> TYPE: DNA
<213> ORGANISM: Arabidopsis thaliana

<400> SEQUENCE: 7
atgggtgaag aagctatagt tctgtatcct gcaccaccaa taggtcactt agtgtccatg      60
gttgagttag gtaaaaccat cctctccaaa aacccatctc tctccatcca cattatctta     120
gttccaccgc cttatcagcc ggaatcaacc gccacttaca tctcctccgt ctcctcctcc     180
ttcccttcaa taaccttcca ccatcttccc gccgtcacac cgtactcctc ctcctccacc     240
tctcgccacc accacgaatc tctcctccta gagatcctct gttttagcaa cccaagtgtc     300
caccgaactc tttttctcac tctctcggaa ttcaatgtcc gagcaatgat catcgatttc     360
ttctgcaccg ccgttttaga catcaccgct gacttcacgt tcccggttta cttcttctac     420
acctctggag ccgcatgtct cgccttttcc ttctatctcc cgaccatcga cgaaacaacc     480
cccgaaaaaa acctcaaaga cattcctaca gttcatatcc ccggcgttcc tccgatgaag     540
ggctccgata tgcctaaggc ggtgctcgaa cgagacgatg aggtctacga tgtttttata     600
atgttcggta acagctctc gaagtcgtca gggattatta tcaatacgtt tgatgcttta     660
gaaaacagag ccatcaaggc cataacagag gagctctgtt tcgcaatat ttatccaatt     720
```

-continued

| | |
|---|---|
| ggaccgctca ttgtaaacgg aagaatcgaa gatagaaacg acaacaaggc agtttcttgt | 780 |
| ctcaattggc tggattcgca gccggaaaag agtgttgtgt ttctctgttt tggaagctta | 840 |
| ggtttgttct caaaagaaca ggtgatagag attgctgttg gtttagagaa aagtgggcag | 900 |
| agattcttgt gggtggtccg taatccaccc gagttagaaa agacagaact ggatttgaaa | 960 |
| tcactcttac cagaaggatt cttaagccga accgaagaca aagggatggt cgtgaaatca | 1020 |
| tgggctccgc aagttccggt tctgaatcat aaagcagtcg ggggattcgt cactcattgc | 1080 |
| ggttggaatt caattcttga agctgtttgt gctggtaaat aatgtatata tatacacatt | 1140 |
| tttcgattat atatatgctt aaaatgttca ttgtggttaa ttgaattggt ttactatata | 1200 |
| ataggtgtgc cgatggtggc ttggccgttg tacgctgagc agaggtttaa tagagtgatg | 1260 |
| attgtggatg agatcaagat tgcgatttcg atgaatgaat cagagacggg tttcgtgagc | 1320 |
| tctacagagg tggagaaacg agtccaagag ataattgggg agtgtccggt tagggagcga | 1380 |
| accatggcta tgaagaacgc agccgaatta gccttgacag aaactggttc gtctcatacc | 1440 |
| gcattaacta ctttactcca gtcgtggagc ccaaagtga | 1479 |

```
<210> SEQ ID NO 8
<211> LENGTH: 1389
<212> TYPE: DNA
<213> ORGANISM: Arabidopsis thaliana

<400> SEQUENCE: 8
```

| | |
|---|---|
| atgggtgaag aagctatagt tctgtatcct gcaccaccaa taggtcactt agtgtccatg | 60 |
| gttgagttag gtaaaaccat cctctccaaa aacccatctc tctccatcca cattatctta | 120 |
| gttccaccgc cttatcagcc ggaatcaacc gccacttaca tctcctccgt ctcctcctcc | 180 |
| ttcccttcaa taaccttcca ccatcttccc gccgtcacac cgtactcctc ctcctccacc | 240 |
| tctcgccacc accacgaatc tctcctccta gagatcctct gttttagcaa cccaagtgtc | 300 |
| caccgaactc tttttctcact ctctcggaat ttcaatgtcc gagcaatgat catcgatttc | 360 |
| ttctgcaccg ccgttttaga catcaccgct gacttcacgt tcccggttta cttcttctac | 420 |
| acctctggag ccgcatgtct cgccttttcc ttctatctcc cgaccatcga cgaaacaacc | 480 |
| cccgaaaaaa acctcaaaga cattcctaca gttcatatcc ccggcgttcc tccgatgaag | 540 |
| ggctccgata tgcctaaggc ggtgctcgaa cgagacgatg aggtctacga tgttttttata | 600 |
| atgttcggta acagctctc gaagtcgtca gggattatta tcaatacgtt tgatgctta | 660 |
| gaaaacagag ccatcaaggc cataacagag gagctctgtt ttcgcaatat ttatccaatt | 720 |
| ggaccgctca ttgtaaacgg aagaatcgaa gatagaaacg acaacaaggc agtttcttgt | 780 |
| ctcaattggc tggattcgca gccggaaaag agtgttgtgt ttctctgttt tggaagctta | 840 |
| ggtttgttct caaaagaaca ggtgatagag attgctgttg gtttagagaa aagtgggcag | 900 |
| agattcttgt gggtggtccg taatccaccc gagttagaaa agacagaact ggatttgaaa | 960 |
| tcactcttac cagaaggatt cttaagccga accgaagaca aagggatggt cgtgaaatca | 1020 |
| tgggctccgc aagttccggt tctgaatcat aaagcagtcg ggggattcgt cactcattgc | 1080 |
| ggttggaatt caattcttga agctgtttgt gctggtgtgc cgatggtggc ttggccgttg | 1140 |
| tacgctgagc agaggtttaa tagagtgatg attgtggatg agatcaagat tgcgatttcg | 1200 |
| atgaatgaat cagagacggg tttcgtgagc tctacagagg tggagaaacg agtccaagag | 1260 |
| ataattgggg agtgtccggt tagggagcga accatggcta tgaagaacgc agccgaatta | 1320 |
| gccttgacag aaactggttc gtctcatacc gcattaacta ctttactcca gtcgtggagc | 1380 | ccaaagtga 1389

<210> SEQ ID NO 9
<211> LENGTH: 462
<212> TYPE: PRT
<213> ORGANISM: Arabidopsis thaliana

<400> SEQUENCE: 9

Met Gly Glu Glu Ala Ile Val Leu Tyr Pro Ala Pro Ile Gly His
1               5                   10                  15

Leu Val Ser Met Val Glu Leu Gly Lys Thr Ile Leu Ser Lys Asn Pro
            20                  25                  30

Ser Leu Ser Ile His Ile Ile Leu Val Pro Pro Tyr Gln Pro Glu
        35                  40                  45

Ser Thr Ala Thr Tyr Ile Ser Ser Val Ser Ser Ser Phe Pro Ser Ile
    50                  55                  60

Thr Phe His His Leu Pro Ala Val Thr Pro Tyr Ser Ser Ser Thr
65                  70                  75                  80

Ser Arg His His Glu Ser Leu Leu Leu Glu Ile Leu Cys Phe Ser
                85                  90                  95

Asn Pro Ser Val His Arg Thr Leu Phe Ser Leu Ser Arg Asn Phe Asn
            100                 105                 110

Val Arg Ala Met Ile Ile Asp Phe Phe Cys Thr Ala Val Leu Asp Ile
        115                 120                 125

Thr Ala Asp Phe Thr Phe Pro Val Tyr Phe Phe Tyr Thr Ser Gly Ala
    130                 135                 140

Ala Cys Leu Ala Phe Ser Phe Tyr Leu Pro Thr Ile Asp Glu Thr Thr
145                 150                 155                 160

Pro Gly Lys Asn Leu Lys Asp Ile Pro Thr Val His Ile Pro Gly Val
                165                 170                 175

Pro Pro Met Lys Gly Ser Asp Met Pro Lys Ala Val Leu Glu Arg Asp
            180                 185                 190

Asp Glu Val Tyr Asp Val Phe Ile Met Phe Gly Lys Gln Leu Ser Lys
        195                 200                 205

Ser Ser Gly Ile Ile Ile Asn Thr Phe Asp Ala Leu Glu Asn Arg Ala
    210                 215                 220

Ile Lys Ala Ile Thr Glu Glu Leu Cys Phe Arg Asn Ile Tyr Pro Ile
225                 230                 235                 240

Gly Pro Leu Ile Val Asn Gly Arg Ile Glu Asp Arg Asn Asp Asn Lys
                245                 250                 255

Ala Val Ser Cys Leu Asn Trp Leu Asp Ser Gln Pro Glu Lys Ser Val
            260                 265                 270

Val Phe Leu Cys Phe Gly Ser Leu Gly Leu Phe Ser Lys Glu Gln Val
        275                 280                 285

Ile Glu Ile Ala Val Gly Leu Glu Lys Ser Gly Gln Arg Phe Leu Trp
    290                 295                 300

Val Val Arg Asn Pro Pro Glu Leu Glu Lys Thr Glu Leu Asp Leu Lys
305                 310                 315                 320

Ser Leu Leu Pro Glu Gly Phe Leu Ser Arg Thr Glu Asp Lys Gly Met
                325                 330                 335

Val Val Lys Ser Trp Ala Pro Gln Val Pro Val Leu Asn His Lys Ala
            340                 345                 350

Val Gly Gly Phe Val Thr His Cys Gly Trp Asn Ser Ile Leu Glu Ala
        355                 360                 365

```
Val Cys Ala Gly Val Pro Met Val Ala Trp Pro Leu Tyr Ala Glu Gln
        370                 375                 380

Arg Phe Asn Arg Val Met Ile Val Asp Glu Ile Lys Ile Ala Ile Ser
385                 390                 395                 400

Met Asn Glu Ser Glu Thr Gly Phe Val Ser Ser Thr Glu Val Glu Lys
                405                 410                 415

Arg Val Gln Glu Ile Ile Gly Glu Cys Pro Val Arg Gly Arg Thr Met
                420                 425                 430

Ala Met Lys Asn Ala Ala Glu Leu Ala Leu Thr Glu Thr Gly Ser Ser
                435                 440                 445

His Thr Ala Leu Thr Thr Leu Leu Gln Ser Trp Ser Pro Lys
        450                 455                 460

<210> SEQ ID NO 10
<211> LENGTH: 1565
<212> TYPE: DNA
<213> ORGANISM: Arabidopsis thaliana

<400> SEQUENCE: 10
atgaccaaac cctccgaccc aaccagagac tcccacgtgg cagttctcgc tttccctttc      60
ggcactcatg cagctcctct cctcaccgtc acgcgccgcc tcgcctccgc ctctccttcc     120
accgtcttct ctttcttcaa caccgcacaa tccaactctt cgttattttc ctccggtgac     180
gaagcagatc gtccggcgaa catcagagta tacgatattg ccgacggtgt tccggaggga     240
tacgtgttta gcgggagacc acaggaggcg atcgagctgt tcttcaagc tgcgccggag     300 aatttccgga gagaaatcgc gaaggcggag acggaggttg tacggaagt gaaatgtttg     360 atgactgatg cgttcttctg gttcgcggct gatatggcga cggagataaa tgcgtcgtgg     420
attgcgtttt ggaccgccgg agcaaactca ctctctgctc atctctacac agatctcatc     480
agagaaacca tcggtgtcaa ggtaatata caaattttt tgaatgcttc ccaattccga     540
cttgtgattt tgtctttat ctcataaata aatatgcaac tagaggaaaa tttagctaaa     600
agaagaaaca gaggttaaga tactattgat ttgaagattt atatgtattt gtggtaatgt     660
ttatgattcc attctaattt acagaagtag gtgagcgtat ggaggagaca taggggtta     720 tctcaggaat ggagaagatc agagtcaaag atacaccaga aggagttgtg tttgggaatt     780
tagactctgt tttctcaaag atgcttcatc aaatgggtct tgctttgcct cgtgccactg     840
ctgttttcat caattctttt gaagatttgg atcctacatt gacgaataac ctcagatcga     900
gatttaaacg atatctgaac atcggtcctc tcgggttatt atcttctaca ttgcaacaac     960
tagtgcaaga tcctcacggt tgtttggctt ggatggagaa gagatcttct ggttctgtgg    1020
cgtacattag ctttggtacg tcatgacac cgcctcctgg agagcttgcg gcgatagcag    1080
aagggttgga atcgagtaaa gtgccgtttg tttggtcgct taaggagaag agcttggttc    1140
agttaccaaa agggttttg gataggacaa gagagcaagg atagtggtt ccatgggcac    1200 cgcaagtgga actgctgaaa cacgaagcaa cgggtgtgtt tgtgacgcat tgtggatgga    1260
actcggtgtt ggagagtgta tcgggtggtg taccgatgat ttgcaggcca ttttttgggg    1320
atcagagatt gaacggaaga gcggtggagg ttgtgtggga gattggaatg acgattatca    1380
atggagtctt cacgaaagat gggtttgaga agtgtttgga taaagttta gttcaagatg    1440 atggtaagaa gatgaaatgt aatgctaaga aacttaaaga actagcttac gaagctgtct    1500
cttctaaagg aaggtcctct gagaatttca gaggattgtt ggatgcagtt gtaaacatta    1560
```

```
                                         -continued
tttga                                                                  1565

<210> SEQ ID NO 11
<211> LENGTH: 1383
<212> TYPE: DNA
<213> ORGANISM: Arabidopsis thaliana

<400> SEQUENCE: 11
atgaccaaac cctccgaccc aaccagagac tcccacgtgg cagttctcgc tttttccttc        60
ggcactcatg cagctcctct cctcaccgtc acgcgccgcc tcgcctccgc ctctccttcc       120
accgtcttct ctttcttcaa caccgcacaa tccaactctt cgttattttc ctccggtgac       180
gaagcagatc gtccggcgaa catcagagta tacgatattg ccgacggtgt tccggaggga       240
tacgtgttta gcgggagacc acaggaggcg atcgagctgt tcttcaagc tgcgccggag        300 aatttccgga gagaaatcgc gaaggcggag acggaggttg gtacggaagt gaaatgtttg       360
atgactgatg cgttcttctg gttcgcggct gatatggcga cggagataaa tgcgtcgtgg       420
attgcgtttt ggaccgccgg agcaaactca ctctctgctc atctctacac agatctcatc       480
agagaaacca tcggtgtcaa agaagtaggt gagcgtatgg aggagacaat aggggttatc       540
tcaggaatgg agaagatcag agtcaaagat acaccagaag gagttgtgtt tgggaattta       600
gactctgttt tctcaaagat gcttcatcaa atgggtcttg ctttgcctcg tgccactgct       660
gttttcatca attcttttga agatttggat cctacattga cgaataaccct cagatcgaga       720 tttaaacgat atctgaacat cggtcctctc gggttattat cttctacatt gcaacaacta       780
gtgcaagatc ctcacggttg tttggcttgg atggagaaga gatcttctgg ttctgtggcg       840
tacattagct ttggtacggt catgacaccg cctcctggag agcttgcggc gatagcagaa       900
gggttggaat cgagtaaagt gccgtttgtt tggtcgctta aggagaagag cttggttcag       960
ttaccaaaag ggtttttgga taggacaaga gagcaaggga tagtggttcc atgggcaccg      1020
caagtggaac tgctgaaaca cgaagcaacg ggtgtgtttg tgacgcattg tggatggaac      1080
tcggtgttgg agagtgtatc gggtggtgta ccgatgattt gcaggccatt ttttgggat       1140 cagagattga acggaagagc ggtggaggtt gtgtgggaga ttggaatgac gattatcaat      1200
ggagtcttca cgaaagatgg gtttgagaag tgtttggata agtttttagt tcaagatgat      1260
ggtaagaaga tgaaatgtaa tgctaagaaa cttaaagaac tagcttacga agctgtctct      1320
tctaaaggaa ggtcctctga gaatttcaga ggattgttgg atgcagttgt aaacattatt      1380
tga                                                                   1383

<210> SEQ ID NO 12
<211> LENGTH: 460
<212> TYPE: PRT
<213> ORGANISM: Arabidopsis thaliana

<400> SEQUENCE: 12

Met Thr Lys Pro Ser Asp Pro Thr Arg Asp Ser His Val Ala Val Leu
1               5                   10                  15

Ala Phe Pro Phe Gly Thr His Ala Ala Pro Leu Leu Thr Val Thr Arg
            20                  25                  30

Arg Leu Ala Ser Ala Ser Pro Ser Thr Val Phe Ser Phe Phe Asn Thr
        35                  40                  45

Ala Gln Ser Asn Ser Ser Leu Phe Ser Ser Gly Asp Glu Ala Asp Arg
    50                  55                  60

Pro Ala Asn Ile Arg Val Tyr Asp Ile Ala Asp Gly Val Pro Glu Gly
```

```
                65                  70                  75                  80
Tyr Val Phe Ser Gly Arg Pro Gln Glu Ala Ile Glu Leu Phe Leu Gln
                    85                  90                  95

Ala Ala Pro Glu Asn Phe Arg Arg Glu Ile Ala Lys Ala Glu Thr Glu
                100                 105                 110

Val Gly Thr Glu Val Lys Cys Leu Met Thr Asp Ala Phe Phe Trp Phe
                115                 120                 125

Ala Ala Asp Met Ala Thr Glu Ile Asn Ala Ser Trp Ile Ala Phe Trp
            130                 135                 140

Thr Ala Gly Ala Asn Ser Leu Ser Ala His Leu Tyr Thr Asp Leu Ile
145                 150                 155                 160

Arg Glu Thr Ile Gly Val Lys Glu Val Gly Glu Arg Met Glu Thr
                    165                 170                 175

Ile Gly Val Ile Ser Gly Met Glu Lys Ile Arg Val Lys Asp Thr Pro
                    180                 185                 190

Glu Gly Val Val Phe Gly Asn Leu Asp Ser Val Phe Ser Lys Met Leu
                195                 200                 205

His Gln Met Gly Leu Ala Leu Pro Arg Ala Thr Ala Val Phe Ile Asn
            210                 215                 220

Ser Phe Glu Asp Leu Asp Pro Thr Leu Thr Asn Asn Leu Arg Ser Arg
225                 230                 235                 240

Phe Lys Arg Tyr Leu Asn Ile Gly Pro Leu Gly Leu Ser Ser Thr
                    245                 250                 255

Leu Gln Gln Leu Val Gln Asp Pro His Gly Cys Leu Ala Trp Met Glu
                260                 265                 270

Lys Arg Ser Ser Gly Ser Val Ala Tyr Ile Ser Phe Gly Thr Val Met
            275                 280                 285

Thr Pro Pro Gly Glu Leu Ala Ala Ile Ala Glu Gly Leu Glu Ser
        290                 295                 300

Ser Lys Val Pro Phe Val Trp Ser Leu Lys Glu Lys Ser Leu Val Gln
305                 310                 315                 320

Leu Pro Lys Gly Phe Leu Asp Arg Thr Arg Glu Gln Gly Ile Val Val
                    325                 330                 335

Pro Trp Ala Pro Gln Val Glu Leu Leu Lys His Glu Ala Thr Gly Val
                340                 345                 350

Phe Val Thr His Cys Gly Trp Asn Ser Val Leu Glu Ser Val Ser Gly
            355                 360                 365

Gly Val Pro Met Ile Cys Arg Pro Phe Phe Gly Asp Gln Arg Leu Asn
        370                 375                 380

Gly Arg Ala Val Glu Val Val Trp Glu Ile Gly Met Thr Ile Ile Asn
385                 390                 395                 400

Gly Val Phe Thr Lys Asp Gly Phe Glu Lys Cys Leu Asp Lys Val Leu
                    405                 410                 415

Val Gln Asp Asp Gly Lys Lys Met Lys Cys Asn Ala Lys Lys Leu Lys
                420                 425                 430

Glu Leu Ala Tyr Glu Ala Val Ser Ser Lys Gly Arg Ser Ser Glu Asn
            435                 440                 445

Phe Arg Gly Leu Leu Asp Ala Val Val Asn Ile Ile
    450                 455                 460

<210> SEQ ID NO 13
<211> LENGTH: 1526
<212> TYPE: DNA
<213> ORGANISM: Arabidopsis thaliana
```

<400> SEQUENCE: 13

```
atggccaaac cctcgcagcc aacgcgagac tcccacgtgg cagttctcgt tttcccttc        60
ggcactcatg cagctcctct cctcgccgtc acgtgccgtc tcgccaccgc tgctccctcc      120
accgtcttct ccttcttcag caccgcacga tccaactcgt cgttactctc ctccgatatc      180
cccacaaaca ttcgtgtcca caacgtcgat gacggtgttc ctgagggatt cgtgttgacg      240
gggaatccac agcacgctgt tgagctgttt cttgaagcgg cgccagagat tttccgaaga      300
gaaatcaagg cggccgagac cgaagttggt aggaagttca agtgcatcct tacggatgcg      360
ttcctctggt tagcagcgga cggcggct gcggagatga aagcgtcgtg ggttgcgtac         420
tatggaggcg gagcaacctc gctcactgct catctctaca cagatgccat cagagaaaac      480
gtcggtgtca aggtataca caatctttt cttgctttac gattccattg aaatttcaat        540
attgcaacta tagatgcctt atagggcaag taaacctgcc tgttccacaa taatcccccg      600
agggattttt aaagaaatg tctccattct aattttcaga agtaggtgag cgtatggagg       660
agacaatagg gtttatctca ggaatggaga agatcagagt caaagacaca caagaaggcg      720
ttgtgtttgg gaacttagac tctgttttct ctaaaacgtt gcaccaaatg ggtcttgctt      780
tacctcgtgc cactgctgtt ttcatcaatt cctttgaaga attggatcct acgtttacaa      840
atgatttcag atcggaattc aaacgttacc taaacatcgg tcctctcgct ttattatctt      900
ctccatcgca aacatcaacg ctagtgcacg atcctcacgg ttgcttggct tggatcgaga      960
agcggtccac tgcttctgta gcgtacattg cctttggtag agtcgcgaca ccgcctcctg     1020
tagagcttgt ggcgatagca caaggattgg aatcgagtaa agtgccttt gtttggtcgc      1080
tacaagagat gaaaatgact catttaccag aaggctttt ggatcggacc agagagcaag      1140
ggatggtggt tccatgggca ccacaagtgg agctgctaaa ccatgaagca atgggtgtgt     1200
ttgtttcgca tggtgggtgg aactcagtgt tggagagtgt gtcggcaggt gtaccgatga     1260
tttgtagacc gattttcggg gatcatgcaa tcaatgcaag atctgtggaa gctgtgtggg     1320
agatcggagt gacgattagt agtggagtct tcacgaagga tggatttgag gagagtttgg     1380
atcgggtttt ggttcaagat gatggcaaga agatgaaggt taatgctaaa aagcttgaag     1440
aactagcaca agaagctgtc tctaccaaag gaagctcctt tgagaatttt ggaggattgt     1500
tggacgaagt tgtgaacttt ggataa                                         1526
```

<210> SEQ ID NO 14
<211> LENGTH: 1378
<212> TYPE: DNA
<213> ORGANISM: Arabidopsis thaliana

<400> SEQUENCE: 14

```
atggccaaac cctcgcagcc aacgcgagac tcccacgtgg cagttctcgt tttcccttc        60
ggcactcatg cagctcctct cctcgccgtc acgtgccgtc tcgccaccgc tgctccctcc      120
accgtcttct ccttcttcag caccgcacga tccaactcgt cgttactctc ctccgatatc      180
cccacaaaca ttcgtgtcca caacgtcgat gacggtgttc ctgagggatt cgtgttgacg      240
gggaatccac agcacgctgt tgagctgttt cttgaagcgg cgccagagat tttccgaaga      300
gaaatcaagg cggccgagac cgaagttggt aggaagttca agtgcatcct tacggatgcg      360
ttcctctggt tagcagcgga cggcggct gcggagatga aagcgtcgtg ggttgcgtac         420
tatggaggcg gagcaacctc gctcactgct catctctaca cagatgccat cagagaaaac      480
```

-continued

```
gtcggtgtca aaagtaggtg agcgtatgga ggagacaata gggtttatct caggaatgga    540
gaagatcaga gtcaaagaca cacaagaagg cgttgtgttt gggaacttag actctgtttt    600
ctctaaaacg ttgcaccaaa tgggtcttgc tttacctcgt gccactgctg ttttcatcaa    660
ttcctttgaa gaattggatc ctacgtttac aaatgatttc agatcggaat tcaaacgtta    720
cctaaacatc ggtcctctcg ctttattatc ttctccatcg caaacatcaa cgctagtgca    780
cgatcctcac ggttgcttgg cttggatcga gaagcggtcc actgcttctg tagcgtacat    840
tgcctttggt agagtcgcga caccgcctcc tgtagagctt gtggcgatag cacaaggatt    900
ggaatcgagt aaagtgcctt tgtttggtc gctacaagag atgaaaatga ctcatttacc    960
agaaggcttt ttggatcgga ccagagagca agggatggtg gttccatggg caccacaagt   1020
ggagctgcta aaccatgaag caatgggtgt gtttgtttcg catggtgggt ggaactcagt   1080
gttggagagt gtgtcggcag gtgtaccgat gatttgtaga ccgattttcg gggatcatgc   1140
aatcaatgca agatctgtgg aagctgtgtg ggagatcgga gtgacgatta gtagtggagt   1200
cttcacgaag gatggatttg aggagagttt ggatcgggtt ttggttcaag atgatggcaa   1260
gaagatgaag gttaatgcta aaaagcttga agaactagca caagaagctg tctctaccaa   1320
aggaagctcc tttgagaatt ttggaggatt gttggacgaa gttgtgaact tggataa     1378
```

<210> SEQ ID NO 15
<211> LENGTH: 459
<212> TYPE: PRT
<213> ORGANISM: Arabidopsis thaliana

<400> SEQUENCE: 15

```
Met Ala Lys Pro Ser Gln Pro Thr Arg Asp Ser His Val Ala Val
1               5                   10                  15

Val Phe Pro Phe Gly Thr His Ala Ala Pro Leu Leu Ala Val Thr Cys
        20                  25                  30

Arg Leu Ala Thr Ala Ala Pro Ser Thr Val Phe Ser Phe Ser Thr
        35                  40                  45

Ala Arg Ser Asn Ser Ser Leu Leu Ser Ser Asp Ile Pro Thr Asn Ile
    50                  55                  60

Arg Val His Asn Val Asp Asp Gly Val Pro Glu Gly Phe Val Leu Thr
65                  70                  75                  80

Gly Asn Pro Gln His Ala Val Glu Leu Phe Leu Glu Ala Ala Pro Glu
                85                  90                  95

Ile Phe Arg Arg Glu Ile Lys Ala Ala Glu Thr Glu Val Gly Arg Lys
            100                 105                 110

Phe Lys Cys Ile Leu Thr Asp Ala Phe Leu Trp Leu Ala Ala Glu Thr
        115                 120                 125

Ala Ala Ala Glu Met Lys Ala Ser Trp Val Ala Tyr Tyr Gly Gly Gly
    130                 135                 140

Ala Thr Ser Leu Thr Ala His Leu Tyr Thr Asp Ala Ile Arg Glu Asn
145                 150                 155                 160

Val Gly Val Lys Glu Val Gly Glu Arg Met Glu Thr Ile Gly Phe
                165                 170                 175

Ile Ser Gly Met Glu Lys Ile Arg Val Lys Asp Thr Gln Glu Gly Val
            180                 185                 190

Val Phe Gly Asn Leu Asp Ser Val Phe Ser Lys Thr Leu His Gln Met
        195                 200                 205

Gly Leu Ala Leu Pro Arg Ala Thr Ala Val Phe Ile Asn Ser Phe Glu
    210                 215                 220
```

```
Glu Leu Asp Pro Thr Phe Thr Asn Asp Phe Arg Ser Glu Phe Lys Arg
225                 230                 235                 240

Tyr Leu Asn Ile Gly Pro Leu Ala Leu Leu Ser Ser Pro Ser Gln Thr
            245                 250                 255

Ser Thr Leu Val His Asp Pro His Gly Cys Leu Ala Trp Ile Glu Lys
            260                 265                 270

Arg Ser Thr Ala Ser Val Ala Tyr Ile Ala Phe Gly Arg Val Ala Thr
            275                 280                 285

Pro Pro Pro Val Glu Leu Val Ala Ile Ala Gln Gly Leu Glu Ser Ser
        290                 295                 300

Lys Val Pro Phe Val Trp Ser Leu Gln Glu Met Lys Met Thr His Leu
305                 310                 315                 320

Pro Glu Gly Phe Leu Asp Arg Thr Arg Glu Gln Gly Met Val Val Pro
                325                 330                 335

Trp Ala Pro Gln Val Glu Leu Leu Asn His Glu Ala Met Gly Val Phe
            340                 345                 350

Val Ser His Gly Gly Trp Asn Ser Val Leu Glu Ser Val Ser Ala Gly
            355                 360                 365

Val Pro Met Ile Cys Arg Pro Ile Phe Gly Asp His Ala Ile Asn Ala
370                 375                 380

Arg Ser Val Glu Ala Val Trp Glu Ile Gly Val Thr Ile Ser Ser Gly
385                 390                 395                 400

Val Phe Thr Lys Asp Gly Phe Glu Glu Ser Leu Asp Arg Val Leu Val
                405                 410                 415

Gln Asp Asp Gly Lys Lys Met Lys Val Asn Ala Lys Lys Leu Glu Glu
            420                 425                 430

Leu Ala Gln Glu Ala Val Ser Thr Lys Gly Ser Ser Phe Glu Asn Phe
            435                 440                 445

Gly Gly Leu Leu Asp Glu Val Val Asn Phe Gly
    450                 455

<210> SEQ ID NO 16
<211> LENGTH: 1610
<212> TYPE: DNA
<213> ORGANISM: Arabidopsis thaliana

<400> SEQUENCE: 16
atggcagaga ttcgccagag aagagtgttg atggtcccag caccgttcca aggccattta      60
ccttcgatga tgaatctagc gtcctacctt tcttcccaag ctttttcaat cacaatcgtt    120
agaaacgaat tcaatttcaa agatatctcc cataatttcc ctggtataaa attcttcacc    180
atcaaggacg gcttgtcaga atctgacgtg aagtctctgg gtctccttga atttgtcctg    240
gagcttaact ctgtctgtga acccctattg aaagagtttc taaccaacca tgatgatgtt    300
gttgacttta tcatttatga tgaatttgtt tacttccctc gacgtgttgc ggaagatatg    360
aatctgccaa agatggtctt tagcccttct tccgccgcta cctcgatcag ccggtgtgtg    420
cttatggaga accaatcaaa tgggttactt cctccacaag gtaccatgct tactttttt     480 acttgggttt tttcaacta gcaaattttg atgtatttaa ttattgttt aacttttata     540 aactactatg ttagtttatt aatttagaat aaggttttgg ttaaatatac aagttaaaga    600
aatattattc ttgtaaggat caattttgta gcattggcag tagactctgt ttttttcaac    660
atttaaaacg tttactgta tttttggtgat ttgggtctat ttctatgaca gacgcaagat    720
ctcaactaga agaaacggtg ccagagtttc atcccttccg tttcaaagat ctgccttta    780
```

-continued

| | |
|---|---|
| cagcttatgg atctatggag agattaatga tactttacga gaatgtaagc aatagagcct | 840 |
| catcttctgg cataatacac aactcttcgg attgcttaga gaactcattc ataacaactg | 900 |
| cacaagagaa atggggagtt ccggtatacc cggttggtcc actccatatg accaattccg | 960 |
| caatgtcatg tccaagttta tttgaagaag aaagaaactg tcttgaatgg cttgagaagc | 1020 |
| aagaaacaag ctcagtgatc tacataagca tggggagctt ggcgatgaca caagatatag | 1080 |
| aggctgtgga gatggccatg ggatttgtcc agagtaatca acccttcttg tgggtgatcc | 1140 |
| gaccaggctc tataaacgga caagaatctt tagacttctt accggaacag ttcaaccaaa | 1200 |
| cggtgaccga tggaagaggt tttgttgtga atgggcccc acaaaaagag gtattaaggc | 1260 |
| atagagcagt ggggagggttt tggaaccatg gtggatggaa ctcgtgcttg agagcataa | 1320 |
| gcagtggtgt accaatgatt tgtaggccgt attctggtga tcagagggtg aatactcgac | 1380 |
| ttatgtcaca tgtttggcaa accgcgtatg agatcgaagg tgaattggaa agaggagctg | 1440 |
| ttgagatggc cgtgaggagg ctcattgtgg atcaagaagg tcaggagatg agaatgagag | 1500 |
| ccaccatatt gaaggaagag gttgaagcct ctgtcacaac cgaaggctct tctcacaatt | 1560 |
| cttttaaacaa tttggtccat gcaataatga tgcaaattga cgaacaatga | 1610 |

<210> SEQ ID NO 17
<211> LENGTH: 1359
<212> TYPE: DNA
<213> ORGANISM: Arabidopsis thaliana

<400> SEQUENCE: 17

| | |
|---|---|
| atggcagaga ttcgccagag aagagtgttg atggtcccag caccgttcca aggccattta | 60 |
| ccttcgatga tgaatctagc gtcctacctt tcttcccaag gcttttcaat cacaatcgtt | 120 |
| agaaacgaat tcaatttcaa agatatctcc cataatttcc ctggtataaa attcttcacc | 180 |
| atcaaggacg gcttgtcaga atctgacgtg aagtctctgg gtctccttga atttgtcctg | 240 |
| gagcttaact ctgtctgtga accccctattg aaagagtttc taaccaacca tgatgatgtt | 300 |
| gttgacttta tcatttatga tgaatttgtt tacttccctc gacgtgttgc ggaagatatg | 360 |
| aatctgccaa agatggtctt tagcccttct tccgccgcta cctcgatcag ccggtgtgtg | 420 |
| cttatggaga accaatcaaa tgggttactt cctccacaag acgcaagatc tcaactagaa | 480 |
| gaaacggtgc cagagtttca tccctttcgt ttcaaagatc tgccttttac agcttatgga | 540 |
| tctatggaga gattaatgat actttacgag aatgtaagca atagagcctc atcttctggc | 600 |
| ataatacaca actcttcgga ttgcttagag aactcattca taacaactgc acaagagaaa | 660 |
| tggggagttc cggtataccc ggttggtcca ctccatatga ccaattccgc aatgtcatgt | 720 |
| ccaagtttat ttgaagaaga aagaaactgt cttgaatggc ttgagaagca gaaacaagc | 780 |
| tcagtgatct acataagcat ggggagcttg gcgatgacac aagatataga ggctgtggag | 840 |
| atggccatgg gatttgtcca gagtaatcaa cccttcttgt gggtgatccg accaggctct | 900 |
| ataaacggac aagaatcttt agacttctta ccggaacagt tcaaccaaac ggtgaccgat | 960 |
| ggaagaggtt ttgttgtgaa atgggcccca caaaaagagg tattaaggca tagagcagtg | 1020 |
| ggagggtttt ggaaccatgg tggatggaac tcgtgcttgg agagcataag cagtggtgta | 1080 |
| ccaatgattt gtaggccgta ttctggtgat cagagggtga atactcgact tatgtcacat | 1140 |
| gtttggcaaa ccgcgtatga gatcgaaggt gaattggaaa gaggagctgt tgagatggcc | 1200 |
| gtgaggaggc tcattgtgga tcaagaaggt caggagatga gaatgagagc caccatattg | 1260 |

```
aaggaagagg ttgaagcctc tgtcacaacc gaaggctctt ctcacaattc tttaaacaat   1320
ttggtccatg caataatgat gcaaattgac gaacaatga                          1359
```

<210> SEQ ID NO 18
<211> LENGTH: 452
<212> TYPE: PRT
<213> ORGANISM: Arabidopsis thaliana

<400> SEQUENCE: 18

```
Met Ala Glu Ile Arg Gln Arg Val Leu Met Val Pro Ala Pro Phe
1               5                   10                  15

Gln Gly His Leu Pro Ser Met Met Asn Leu Ala Ser Tyr Leu Ser Ser
                20                  25                  30

Gln Gly Phe Ser Ile Thr Ile Val Arg Asn Glu Phe Asn Phe Lys Asp
            35                  40                  45

Ile Ser His Asn Phe Pro Gly Ile Lys Phe Phe Thr Ile Lys Asp Gly
        50                  55                  60

Leu Ser Glu Ser Asp Val Lys Ser Leu Gly Leu Leu Glu Phe Val Leu
65                  70                  75                  80

Glu Leu Asn Ser Val Cys Glu Pro Leu Leu Lys Glu Phe Leu Thr Asn
                85                  90                  95

His Asp Asp Val Val Asp Phe Ile Ile Tyr Asp Glu Val Tyr Phe
                100                 105                 110

Pro Arg Arg Val Ala Glu Asp Met Asn Leu Pro Lys Met Val Phe Ser
            115                 120                 125

Pro Ser Ser Ala Ala Thr Ser Ile Ser Arg Cys Val Leu Met Glu Asn
        130                 135                 140

Gln Ser Asn Gly Leu Leu Pro Pro Gln Asp Ala Arg Ser Gln Leu Glu
145                 150                 155                 160

Glu Thr Val Pro Glu Phe His Pro Phe Arg Phe Lys Asp Leu Pro Phe
                165                 170                 175

Thr Ala Tyr Gly Ser Met Glu Arg Leu Met Ile Leu Tyr Glu Asn Val
            180                 185                 190

Ser Asn Arg Ala Ser Ser Ser Gly Ile Ile His Asn Ser Ser Asp Cys
        195                 200                 205

Leu Glu Asn Ser Phe Ile Thr Thr Ala Gln Glu Lys Trp Gly Val Pro
    210                 215                 220

Val Tyr Pro Val Gly Pro Leu His Met Thr Asn Ser Ala Met Ser Cys
225                 230                 235                 240

Pro Ser Leu Phe Glu Glu Arg Asn Cys Leu Glu Trp Leu Glu Lys
                245                 250                 255

Gln Glu Thr Ser Ser Val Ile Tyr Ile Ser Met Gly Ser Leu Ala Met
            260                 265                 270

Thr Gln Asp Ile Glu Ala Val Glu Met Ala Met Gly Phe Val Gln Ser
        275                 280                 285

Asn Gln Pro Phe Leu Trp Val Ile Arg Pro Gly Ser Ile Asn Gly Gln
    290                 295                 300

Glu Ser Leu Asp Phe Leu Pro Glu Gln Phe Asn Gln Thr Val Thr Asp
305                 310                 315                 320

Gly Arg Gly Phe Val Val Lys Trp Ala Pro Gln Lys Glu Val Leu Arg
                325                 330                 335

His Arg Ala Val Gly Gly Phe Trp Asn His Gly Gly Trp Asn Ser Cys
            340                 345                 350

Leu Glu Ser Ile Ser Ser Gly Val Pro Met Ile Cys Arg Pro Tyr Ser
```

```
                355                 360                 365
Gly Asp Gln Arg Val Asn Thr Arg Leu Met Ser His Val Trp Gln Thr
    370                 375                 380

Ala Tyr Glu Ile Glu Gly Glu Leu Glu Arg Gly Ala Val Glu Met Ala
385                 390                 395                 400

Val Arg Arg Leu Ile Val Asp Gln Glu Gly Gln Glu Met Arg Met Arg
                405                 410                 415

Ala Thr Ile Leu Lys Glu Glu Val Glu Ala Ser Val Thr Thr Glu Gly
                420                 425                 430

Ser Ser His Asn Ser Leu Asn Asn Leu Val His Ala Ile Met Met Gln
                435                 440                 445

Ile Asp Glu Gln
    450

<210> SEQ ID NO 19
<211> LENGTH: 1434
<212> TYPE: DNA
<213> ORGANISM: Arabidopsis thaliana

<400> SEQUENCE: 19
atggaggaaa agcaagtgaa ggagacaagg atagtgttgg ttccagttcc agctcaaggt      60
catgtaactc cgatgatgca actaggaaaa gctcttcact caaagggttt ctccatcact     120
gttgttctga cacagtctaa tcgagttagc tcttccaaag acttctctga tttccatttc     180
ctcaccatcc caggcagctt aactgagtct gatctccaaa acctaggacc acaaaagttt     240
gtgctcaagc tcaatcaaat ttgtgaggca agcttcaagc agtgtatagg tcaactattg     300
catgaacaat gtaataatga tattgcttgt gtcgtctacg atgagtacat gtacttctct     360
catgctgcag taaaagagtt tcaacttcct agtgtcgtct ttagcacgac aagtgctact     420
gcttttgtct gtcgctctgt tttgtctaga gtcaacgcag agtcgttctt gatcgacatg     480
aaaggtattc aagattctag cttgttttat cttaattcaa atcctatttt atagaaacta     540
atccaaatga tcgatgttat cttttcagat cctgaaacac aagacaaagt atttccaggg     600
ttgcatcctc tgaggtacaa ggatctacca acttcagtat ttgggccaat agagagtacg     660
ctcaaggttt acagtgagac tgtgaacact cgaacagctt ccgctgttat catcaactca     720
gcaagctgtt tagagagctc atctttggca aggttgcaac aacaactgca agttccggtg     780
tatcctatag gcccacttca tattacagct tcagcgcctt ctagtttact agaagaagac     840
aggagttgcg ttgagtggtt gaacaagcaa aaatcaaatt cagttattta cataagcttg     900
ggaagcttgg ctctaatgga caccaaagac atgttggaga tggcttgggg attaagtaat     960
agcaaccaac ctttcttatg ggtggtcaga ccgggctcta ttccggggtc agaatggaca    1020
gagtccttac cagaggaatt caataggttg gtttcagaaa gaggttacat tgtgaaatgg    1080
gctccgcaga tggaagttct cagacatcct gcagtaggag ggttttggag tcactgtgga    1140
tggaactcaa cagtagagag catcggggaa ggagttccga tgatatgtag gccttcacc     1200
ggggatcaga aagtcaatgc gaggtactta gagagagttt ggagaattgg ggttcaattg    1260
gagggagatc tggataaaga aactgtggag agagctgtag agtggttgct gtggatgaa     1320
gaaggagcag aaatgaggaa gagagccatt gacttgaaag aaaagattga aacctctgtt    1380
agaagtggag gttcctcatg cagctcacta gacgactttg ttaattccat gtga          1434

<210> SEQ ID NO 20
<211> LENGTH: 1350
```

```
<212> TYPE: DNA
<213> ORGANISM: Arabidopsis thaliana

<400> SEQUENCE: 20
atggaggaaa agcaagtgaa ggagacaagg atagtgttgg ttccagttcc agctcaaggt      60
catgtaactc cgatgatgca actaggaaaa gctcttcact caaagggttt ctccatcact     120
gttgttctga cacagtctaa tcgagttagc tcttccaaag acttctctga tttccatttc     180
ctcaccatcc caggcagctt aactgagtct gatctccaaa acctaggacc acaaaagttt     240
gtgctcaagc tcaatcaaat ttgtgaggca agcttcaagc agtgtatagg tcaactattg     300
catgaacaat gtaataatga tattgcttgt gtcgtctacg atgagtacat gtacttctct     360
catgctgcag taaaagagtt tcaacttcct agtgtcgtct ttagcacgac aagtgctact     420
gcttttgtct gtcgctctgt tttgtctaga gtcaacgcag agtcgttctt gatcgacatg     480
aaagatcctg aaacacaaga caaagtattt ccagggttgc atcctctgag gtacaaggat     540
ctaccaactt cagtatttgg gccaatagag agtacgctca aggtttacag tgagactgtg     600
aacactcgaa cagcttccgc tgttatcatc aactcagcaa gctgtttaga gagctcatct     660
ttggcaaggt tgcaacaaca actgcaagtt ccggtgtatc ctataggccc acttcatatt     720
acagcttcag cgccttctag tttactagaa gaagacagga gttgcgttga gtggttgaac     780
aagcaaaaat caaattcagt tatttacata agcttggaaa gcttggctct aatggacacc     840
aaagacatgt tggagatggc ttggggatta agtaatagca accaacctt cttatgggtg     900
gtcagaccgg gctctattcc ggggtcagaa tggacagagt ccttaccaga ggaattcaat     960
aggttggttt cagaaagagg ttacattgtg aaatgggctc cgcagatgga agttctcaga    1020
catcctgcag taggagggtt ttggagtcac tgtggatgga actcaacagt agagagcatc    1080
ggggaaggag ttccgatgat atgtaggcct ttcaccgggg atcagaaagt caatgcgagg    1140
tacttagaga gagtttggag aattgggggtt caattggagg gagatctgga taaagaaact    1200
gtggagagag ctgtagagtg gttgcttgtg gatgaagaag gagcagaaat gaggaagaga    1260
gccattgact tgaaagaaaa gattgaaacc tctgttagaa gtggaggttc ctcatgcagc    1320
tcactagacg actttgttaa ttccatgtga                                     1350

<210> SEQ ID NO 21
<211> LENGTH: 449
<212> TYPE: PRT
<213> ORGANISM: Arabidopsis thaliana

<400> SEQUENCE: 21

Met Glu Glu Lys Gln Val Lys Glu Thr Arg Ile Val Leu Val Pro Val
1               5                   10                  15

Pro Ala Gln Gly His Val Thr Pro Met Met Gln Leu Gly Lys Ala Leu
                20                  25                  30

His Ser Lys Gly Phe Ser Ile Thr Val Val Leu Thr Gln Ser Asn Arg
            35                  40                  45

Val Ser Ser Lys Asp Phe Ser Asp Phe His Phe Leu Thr Ile Pro
        50                  55                  60

Gly Ser Leu Thr Glu Ser Asp Leu Gln Asn Leu Gly Pro Gln Lys Phe
65                  70                  75                  80

Val Leu Lys Leu Asn Gln Ile Cys Glu Ala Ser Phe Lys Gln Cys Ile
                85                  90                  95

Gly Gln Leu Leu His Glu Gln Cys Asn Asn Asp Ile Ala Cys Val Val
            100                 105                 110
```

```
Tyr Asp Glu Tyr Met Tyr Phe Ser His Ala Ala Val Lys Glu Phe Gln
            115                 120                 125

Leu Pro Ser Val Val Phe Ser Thr Thr Ser Ala Thr Ala Phe Val Cys
        130                 135                 140

Arg Ser Val Leu Ser Arg Val Asn Ala Glu Ser Phe Leu Ile Asp Met
145                 150                 155                 160

Lys Asp Pro Glu Thr Gln Asp Lys Val Phe Pro Gly Leu His Pro Leu
                165                 170                 175

Arg Tyr Lys Asp Leu Pro Thr Ser Val Phe Gly Pro Ile Glu Ser Thr
            180                 185                 190

Leu Lys Val Tyr Ser Glu Thr Val Asn Thr Arg Thr Ala Ser Ala Val
        195                 200                 205

Ile Ile Asn Ser Ala Ser Cys Leu Glu Ser Ser Ser Leu Ala Arg Leu
210                 215                 220

Gln Gln Gln Leu Gln Val Pro Val Tyr Pro Ile Gly Pro Leu His Ile
225                 230                 235                 240

Thr Ala Ser Ala Pro Ser Ser Leu Leu Glu Glu Asp Arg Ser Cys Val
                245                 250                 255

Glu Trp Leu Asn Lys Gln Lys Ser Asn Ser Val Ile Tyr Ile Ser Leu
            260                 265                 270

Gly Ser Leu Ala Leu Met Asp Thr Lys Asp Met Leu Glu Met Ala Trp
        275                 280                 285

Gly Leu Ser Asn Ser Asn Gln Pro Phe Leu Trp Val Val Arg Pro Gly
290                 295                 300

Ser Ile Pro Gly Ser Glu Trp Thr Glu Ser Leu Pro Glu Glu Phe Asn
305                 310                 315                 320

Arg Leu Val Ser Glu Arg Gly Tyr Ile Val Lys Trp Ala Pro Gln Met
                325                 330                 335

Glu Val Leu Arg His Pro Ala Val Gly Gly Phe Trp Ser His Cys Gly
            340                 345                 350

Trp Asn Ser Thr Val Glu Ser Ile Gly Glu Gly Val Pro Met Ile Cys
        355                 360                 365

Arg Pro Phe Thr Gly Asp Gln Lys Val Asn Ala Arg Tyr Leu Glu Arg
370                 375                 380

Val Trp Arg Ile Gly Val Gln Leu Glu Gly Asp Leu Asp Lys Glu Thr
385                 390                 395                 400

Val Glu Arg Ala Val Glu Trp Leu Leu Val Asp Glu Glu Gly Ala Glu
                405                 410                 415

Met Arg Lys Arg Ala Ile Asp Leu Lys Glu Lys Ile Glu Thr Ser Val
            420                 425                 430

Arg Ser Gly Gly Ser Ser Cys Ser Leu Asp Asp Phe Val Asn Ser
        435                 440                 445

Met

<210> SEQ ID NO 22
<211> LENGTH: 1495
<212> TYPE: DNA
<213> ORGANISM: Arabidopsis thaliana

<400> SEQUENCE: 22
atggagaaga gaaacgagag acaagtgatt ctttttcctc taccattaca aggttgcata      60
aaccctatgc ttcagctagc aaagatcctt tactcaagag gttttcgat  caccatcatc     120 cacacgcgct tcaacgcgcc caaatcttca gaccatcctc tcttcacttt cttacaaatc     180
```

-continued

```
cgcgacggct tgtctgaatc tcagactcaa tctcgtgatc ttttgcttca actcacgctt      240
ctcaacaaca attgtcagat cccatttcga gagtgtttgg ctaaactcat taaacctagt      300
tcagattcag gaacagagga taggaaaatt agctgtgtga tcgatgattc cggttgggtt      360
ttcacacaat ccgtggcgga gagttttaat cttcctcgat ttgtcctctg tgcttataag      420 ttctcttct ttctcggaca ttttcttgtt cctcagattc gtcgtgaagg gtttcttcca      480
gtaccaggta cggctttgac tcatagtagg tcattgttct tattgttaat tgagtcatca      540
aagacacaat tggtccgtat ttcttgaact ttctaggttt gtttcagatt cggaggcaga      600
tgatctagtt cctgagtttc caccgcttcg aaagaaagat ctttcgagaa ttatgggaac      660
cagcgctcag agtaagcctc tagatgctta cttgcttaag atactcgacg cgacgaagcc      720
agcttcaggg attatagtta tgtcctgcaa agagcttgac catgattcac ttgctgagtc      780
caacaaagtt ttcagcattc cgatatttcc cattggccct tttcacattc atgacgtccc      840
agcctcgtct agcagcttgt tagaaccgga ccagagttgc attccatggt tagatatgcg      900
tgaaacgaga tcagtagtct acgtgagctt agggagcatt gcgagtctta acgagtctga      960
cttcttggag attgcttgtg gactaagaaa caccaaccaa tccttcttgt gggttgtccg      1020
gcctggttca gtccatggca gagattggat cgaatcatta ccttcagggt tcatggaaag      1080
tctcgatggt aaaggaaaga tagtgagatg ggcaccgcag ctagacgttc ttgcgcatag      1140
agccacggga gggtttttga ctcataatgg atggaactcg acattagaga gtatatgcga      1200
aggagtacct atgatctgct tgccttgtaa gtgggaccca tttgtaaacg cgagattcat      1260
aagcgaagtt tggagggttg ggattcactt ggaaggtcgg atagagcgaa gagaaatcga      1320
gagagctgtt ataagactaa tggttgagtc gaaggagaga gagattcgag gtagaatcaa      1380
agtcttgcga gacgaagtaa gaaggtcagt taaacaagga ggttcgtcat atcgatcttt      1440
agatgagttg gttgatcgta tatcaatcat catcgagcca ctagtgccta cgtga         1495
```

<210> SEQ ID NO 23
<211> LENGTH: 1395
<212> TYPE: DNA
<213> ORGANISM: Arabidopsis thaliana

<400> SEQUENCE: 23

```
atggagaaga gaaacgagag acaagtgatt cttttcctc taccattaca aggttgcata        60
aaccctatgc ttcagctagc aaagatcctt tactcaagag gttttcgat caccatcatc       120 cacacgcgct tcaacgcgcc caaatcttca gaccatcctc tcttcacttt cttacaaatc      180
cgcgacggct tgtctgaatc tcagactcaa tctcgtgatc ttttgcttca actcacgctt      240
ctcaacaaca attgtcagat cccatttcga gagtgtttgg ctaaactcat taaacctagt      300
tcagattcag gaacagagga taggaaaatt agctgtgtga tcgatgattc cggttgggtt      360
ttcacacaat ccgtggcgga gagttttaat cttcctcgat ttgtcctctg tgcttataag      420 ttctcttct ttctcggaca ttttcttgtt cctcagattc gtcgtgaagg gtttcttcca      480
gtaccagatt cggaggcaga tgatctagtt cctgagtttc caccgcttcg aaagaaagat      540
ctttcgagaa ttatgggaac cagcgctcag agtaagcctc tagatgctta cttgcttaag      600
atactcgacg cgacgaagcc agcttcaggg attatagtta tgtcctgcaa agagcttgac      660
catgattcac ttgctgagtc caacaaagtt ttcagcattc cgatatttcc cattggccct      720
tttcacattc atgacgtccc agcctcgtct agcagcttgt tagaaccgga ccagagttgc      780
```

-continued

```
attccatggt tagatatgcg tgaaacgaga tcagtagtct acgtgagctt agggagcatt    840
gcgagtctta acgagtctga cttcttggag attgcttgtg gactaagaaa caccaaccaa    900
tccttcttgt gggttgtccg gcctggttca gtccatggca gagattggat cgaatcatta    960
ccttcagggt tcatggaaag tctcgatggt aaaggaaaga tagtgagatg ggcaccgcag   1020
ctagacgttc ttgcgcatag agccacggga gggttttttga ctcataatgg atggaactcg   1080
acattagaga gtatatgcga aggagtacct atgatctgct tgccttgtaa gtgggaccaa   1140
tttgtaaacg cgagattcat aagcgaagtt tggagggttg ggattcactt ggaaggtcgg   1200
atagagcgaa gagaaatcga gagagctgtt ataagactaa tggttgagtc gaaaggagaa   1260
gagattcgag gtagaatcaa agtcttgcga gacgaagtaa aaggtcagt taaacaagga    1320 ggttcgtcat atcgatcttt agatgagttg gttgatcgta tatcaatcat catcgagcca   1380
ctagtgccta cgtga                                                   1395
```

<210> SEQ ID NO 24
<211> LENGTH: 464
<212> TYPE: PRT
<213> ORGANISM: Arabidopsis thaliana

<400> SEQUENCE: 24

```
Met Glu Lys Arg Asn Glu Arg Gln Val Ile Leu Phe Pro Leu Pro Leu
1               5                   10                  15

Gln Gly Cys Ile Asn Pro Met Leu Gln Leu Ala Lys Ile Leu Tyr Ser
            20                  25                  30

Arg Gly Phe Ser Ile Thr Ile His Thr Arg Phe Asn Ala Pro Lys
        35                  40                  45

Ser Ser Asp His Pro Leu Phe Thr Phe Leu Gln Ile Arg Asp Gly Leu
    50                  55                  60

Ser Glu Ser Gln Thr Gln Ser Arg Asp Leu Leu Leu Gln Leu Thr Leu
65                  70                  75                  80

Leu Asn Asn Asn Cys Gln Ile Pro Phe Arg Glu Cys Leu Ala Lys Leu
                85                  90                  95

Ile Lys Pro Ser Ser Asp Ser Gly Thr Glu Asp Arg Lys Ile Ser Cys
            100                 105                 110

Val Ile Asp Asp Ser Gly Trp Val Phe Thr Gln Ser Val Ala Glu Ser
        115                 120                 125

Phe Asn Leu Pro Arg Phe Val Leu Cys Ala Tyr Lys Phe Ser Phe Phe
    130                 135                 140

Leu Gly His Phe Leu Val Pro Gln Ile Arg Arg Glu Gly Phe Leu Pro
145                 150                 155                 160

Val Pro Asp Ser Glu Ala Asp Asp Leu Val Pro Glu Phe Pro Pro Leu
                165                 170                 175

Arg Lys Lys Asp Leu Ser Arg Ile Met Gly Thr Ser Ala Gln Ser Lys
            180                 185                 190

Pro Leu Asp Ala Tyr Leu Leu Lys Ile Leu Asp Ala Thr Lys Pro Ala
        195                 200                 205

Ser Gly Ile Ile Val Met Ser Cys Lys Glu Leu Asp His Asp Ser Leu
    210                 215                 220

Ala Glu Ser Asn Lys Val Phe Ser Ile Pro Ile Phe Pro Ile Gly Pro
225                 230                 235                 240

Phe His Ile His Asp Val Pro Ala Ser Ser Ser Leu Leu Glu Pro
                245                 250                 255

Asp Gln Ser Cys Ile Pro Trp Leu Asp Met Arg Glu Thr Arg Ser Val
```

-continued

```
                         260                 265                 270
Val Tyr Val Ser Leu Gly Ser Ile Ala Ser Leu Asn Glu Ser Asp Phe
                     275                 280                 285
Leu Glu Ile Ala Cys Gly Leu Arg Asn Thr Asn Gln Ser Phe Leu Trp
                 290                 295                 300
Val Val Arg Pro Gly Ser Val His Gly Arg Asp Trp Ile Glu Ser Leu
305                 310                 315                 320
Pro Ser Gly Phe Met Glu Ser Leu Asp Gly Lys Gly Lys Ile Val Arg
                325                 330                 335
Trp Ala Pro Gln Leu Asp Val Leu Ala His Arg Ala Thr Gly Gly Phe
            340                 345                 350
Leu Thr His Asn Gly Trp Asn Ser Thr Leu Glu Ser Ile Cys Glu Gly
        355                 360                 365
Val Pro Met Ile Cys Leu Pro Cys Lys Trp Asp Gln Phe Val Asn Ala
    370                 375                 380
Arg Phe Ile Ser Glu Val Trp Arg Val Gly Ile His Leu Glu Gly Arg
385                 390                 395                 400
Ile Glu Arg Arg Glu Ile Glu Arg Ala Val Ile Arg Leu Met Val Glu
                405                 410                 415
Ser Lys Gly Glu Glu Ile Arg Gly Arg Ile Lys Val Leu Arg Asp Glu
            420                 425                 430
Val Arg Arg Ser Val Lys Gln Gly Gly Ser Ser Tyr Arg Ser Leu Asp
        435                 440                 445
Glu Leu Val Asp Arg Ile Ser Ile Ile Glu Pro Leu Val Pro Thr
    450                 455                 460

<210> SEQ ID NO 25
<211> LENGTH: 1804
<212> TYPE: DNA
<213> ORGANISM: Arabidopsis thaliana

<400> SEQUENCE: 25
atggaggaga agagaaatgg tctgcgtgtg attctcttcc ctcttccatt acaaggttgc      60 atcaaccota tgcttcagct cgccaacatc cttcacgtaa gaggcttctc cattaccgtg     120
atccacacgc gcttcaacgc gccaaaaagct tcaagccatc ctctcttcac tttcttacag   180
attcctgatg gtttgtctga acggagatt caagatggtg ttatgtcttt gctcgcgcaa     240 atcaaccta cgctgagtc tccgtttcgt gattgcttgc gtaaagtgtt gctggaatca      300
aaagagtcag agagggttac ttgtttgatc gatgactgtg atggctctt cacacaatct    360 gtttcagaga gtttgaagct tccgaggctc gttctctgta cttttaaagc cactttcttc   420
aatgcttatc cgagtcttcc acttatccga accaagggat atcttccagt ttcaggtaat   480
taatgcttca tgaaatgctt attttttaatg gtcaaattgc tatataggaa aaagttatct  540
aacttgggta ggaaattcgt attttttgtaa acatatttgc atactgtgac tacaaatgct  600
cttcgcactc tcacctatga tgatgtcagt ctattaaaag gaaaatgtgt catccaataa   660
aaataaggaa agtaaaattt ttgcatttga ccaaaatggt atatttgtat ttattccataa  720 ttgtgttgtt ttttttaaaaa aatggcgtca tctctactaa taaaatagca tggcatgtca  780
atgaatattg gtctaacaaa taaaaagtta agttgttca cgtaactaag gaaaagagta    840
ggatatttag gttatttact atggacactc tattttgaat tctggttatc aagtttataa   900 gattgtttg agcctttgtg tcttagaatc ggaagcagag gactctgttc ctgagttccc   960
gccgcttcaa aagagagatc tttcaaaggt tttcggggag ttcggagaga aactcgatcc  1020
```

```
gttcttacat gctgtagtcg aaacgacaat aagatcttca gggttaatat acatgtcctg   1080
cgaagagctt gagaaagatt cgttgactct ttctaacgaa attttaaag ttccggtttt    1140 tgcaattggt ccgtttcaca gctacttctc tgcttcgtca agcagcttgt tcacacaaga   1200
cgagacttgc attctgtggt tagatgatca agaagataaa tctgtgatct acgttagtct   1260
aggaagcgtt gtgaacataa cggaaacaga gttcttggag attgcgtgtg gtttaagcaa   1320
tagcaaacag cctttcttgt gggtagtacg acccggttca gtactcggcg cgaaatggat   1380
cgaaccgctc tctgaagggc tggttagtag ccttgaagag aaaggaaaga ttgtgaaatg   1440
ggcaccacaa caggaggttc ttgcgcatcg tgccacagga gggttttga cacacaatgg    1500 ttggaactca cgctagaga gtatatgcga agggggttcct atgatctgcc taccaggagg   1560
ttgggatcaa atgctgaatt caagatttgt tagcgatatt tggaagattg gaattcactt   1620
ggaaggtcgg attgaaaaaa aggagattga gaaagctgtg agggtgttaa tggaggaaag   1680
tgaaggaaat aagattcgtg agagaatgaa agttctgaaa gatgaggtcg agaaatcggt   1740
caaacaagga ggctcatctt ttcaatctat tgagactcta gctaatcata tactattgtt   1800
gtaa                                                                1804

<210> SEQ ID NO 26
<211> LENGTH: 1353
<212> TYPE: DNA
<213> ORGANISM: Arabidopsis thaliana

<400> SEQUENCE: 26
atggaggaga agagaaatgg tctgcgtgtg attctcttcc ctcttccatt acaaggttgc     60
atcaacccta tgcttcagct cgccaacatc cttcacgtaa gaggcttctc cattaccgtg   120
atccacacgc gcttcaacgc gccaaaagct tcaagccatc ctctcttcac tttcttacag   180
attcctgatg gtttgtctga aacggagatt caagatggtg ttatgtcttt gctcgcgcaa   240
atcaacctta cgctgagtc tccgtttcgt gattgcttgc gtaaagtgtt gctggaatca   300
aaagagtcag agagggttac ttgtttgatc gatgactgtg gatggctctt cacacaatct   360
gtttcagaga gtttgaagct tccgaggctc gttctctgta cttttaaagc cactttcttc   420
aatgcttatc cgagtcttcc acttatccga accaagggat atcttccagt ttcagaatcg   480
gaagcagagg actctgttcc tgagttcccg ccgcttcaaa agagagatct ttcaaaggtt   540
ttcggggagt tcggagagaa actcgatccg ttcttacatg ctgtagtcga aacgacaata   600
agatcttcag ggttaatata catgtcctgc gaagagcttg agaaagattc gttgactctt   660
tctaacgaaa tttttaaagt tccggttttt gcaattggtc cgtttcacag ctacttctct   720
gcttcgtcaa gcagcttgtt cacacaagac gagacttgca ttctgtggtt agatgatcaa   780
gaagataaat ctgtgatcta cgttagtcta ggaagcgttg tgaacataac ggaaacagag   840
ttcttggaga ttgcgtgtgg tttaagcaat agcaaacagc ctttcttgtg ggtagtacga   900
cccggttcag tactcggcgc gaaatggatc gaaccgctct ctgaagggct ggttagtagc   960
cttgaagaga aaggaaagat tgtgaaatgg gcaccacaac aggaggttct tgcgcatcgt  1020
gccacaggag ggttttgac acacaatggt tggaactcaa cgctagagag tatatgcgaa   1080 gggggttccta tgatctgcct accaggaggt tgggatcaaa tgctgaattc aagatttgtt  1140
agcgatattt ggaagattgg aattcacttg gaaggtcgga ttgaaaaaaa ggagattgag  1200
aaagctgtga gggtgttaat ggaggaaagt gaaggaaata agattcgtga gagaatgaaa  1260
```

```
gttctgaaag atgaggtcga gaaatcggtc aaacaaggag gctcatcttt tcaatctatt    1320
gagactctag ctaatcatat actattgttg taa                                 1353
```

<210> SEQ ID NO 27
<211> LENGTH: 450
<212> TYPE: PRT
<213> ORGANISM: Arabidopsis thaliana

<400> SEQUENCE: 27

```
Met Glu Glu Lys Arg Asn Gly Leu Arg Val Ile Leu Phe Pro Leu Pro
1               5                   10                  15

Leu Gln Gly Cys Ile Asn Pro Met Leu Gln Leu Ala Asn Ile Leu His
            20                  25                  30

Val Arg Gly Phe Ser Ile Thr Val Ile His Thr Arg Phe Asn Ala Pro
        35                  40                  45

Lys Ala Ser Ser His Pro Leu Phe Thr Phe Leu Gln Ile Pro Asp Gly
    50                  55                  60

Leu Ser Glu Thr Glu Ile Gln Asp Gly Val Met Ser Leu Leu Ala Gln
65                  70                  75                  80

Ile Asn Leu Asn Ala Glu Ser Pro Phe Arg Asp Cys Leu Arg Lys Val
                85                  90                  95

Leu Leu Glu Ser Lys Glu Ser Glu Arg Val Thr Cys Leu Ile Asp Asp
            100                 105                 110

Cys Gly Trp Leu Phe Thr Gln Ser Val Ser Glu Ser Leu Lys Leu Pro
        115                 120                 125

Arg Leu Val Leu Cys Thr Phe Lys Ala Thr Phe Phe Asn Ala Tyr Pro
    130                 135                 140

Ser Leu Pro Leu Ile Arg Thr Lys Gly Tyr Leu Pro Val Ser Glu Ser
145                 150                 155                 160

Glu Ala Glu Asp Ser Val Pro Glu Phe Pro Leu Gln Lys Arg Asp
                165                 170                 175

Leu Ser Lys Val Phe Gly Glu Phe Gly Glu Lys Leu Asp Pro Phe Leu
            180                 185                 190

His Ala Val Val Glu Thr Thr Ile Arg Ser Ser Gly Leu Ile Tyr Met
        195                 200                 205

Ser Cys Glu Glu Leu Glu Lys Asp Ser Leu Thr Leu Ser Asn Glu Ile
    210                 215                 220

Phe Lys Val Pro Val Phe Ala Ile Gly Pro Phe His Ser Tyr Phe Ser
225                 230                 235                 240

Ala Ser Ser Ser Leu Phe Thr Gln Asp Glu Thr Cys Ile Leu Trp
                245                 250                 255

Leu Asp Asp Gln Glu Asp Lys Ser Val Ile Tyr Val Ser Leu Gly Ser
            260                 265                 270

Val Val Asn Ile Thr Glu Thr Glu Phe Leu Glu Ile Ala Cys Gly Leu
        275                 280                 285

Ser Asn Ser Lys Gln Pro Phe Leu Trp Val Val Arg Pro Gly Ser Val
    290                 295                 300

Leu Gly Ala Lys Trp Ile Glu Pro Leu Ser Glu Gly Leu Val Ser Ser
305                 310                 315                 320

Leu Glu Glu Lys Gly Lys Ile Val Lys Trp Ala Pro Gln Gln Glu Val
                325                 330                 335

Leu Ala His Arg Ala Thr Gly Gly Phe Leu Thr His Asn Gly Trp Asn
            340                 345                 350

Ser Thr Leu Glu Ser Ile Cys Glu Gly Val Pro Met Ile Cys Leu Pro
```

|  |  |  | 355 |  |  |  | 360 |  |  |  | 365 |  |
|---|---|---|---|---|---|---|---|---|---|---|---|---|
| Gly | Gly | Trp | Asp | Gln | Met | Leu | Asn | Ser | Arg | Phe | Val | Ser | Asp | Ile | Trp |
|  | 370 |  |  |  | 375 |  |  |  |  | 380 |  |

Lys Ile Gly Ile His Leu Glu Gly Arg Ile Glu Lys Lys Glu Ile Glu
385              390              395              400

Lys Ala Val Arg Val Leu Met Glu Glu Ser Glu Gly Asn Lys Ile Arg
            405              410              415

Glu Arg Met Lys Val Leu Lys Asp Glu Val Glu Lys Ser Val Lys Gln
        420              425              430

Gly Gly Ser Ser Phe Gln Ser Ile Glu Thr Leu Ala Asn His Ile Leu
        435              440              445

Leu Leu
450

<210> SEQ ID NO 28
<211> LENGTH: 1488
<212> TYPE: DNA
<213> ORGANISM: Arabidopsis thaliana

<400> SEQUENCE: 28

```
atggtttccg aaacaaccaa atcttctcca cttcactttg ttctcttccc tttcatggct      60
caaggccaca tgattcccat ggttgatatt gcaaggctct ggctcagcg tggtgtgatc     120
ataacaattg tcacgacgcc tcacaatgca gcgaggttca gaatgtcct aaaccgtgcc     180
attgagtctg gcttgcccat caacttagtg caagtcaagt ttccatatct agaagctggt     240
ttgcaagaag gacaagagaa tatcgattct cttgacacaa tggagcggat gatacctttc     300
tttaaagcgg ttaactttct cgaagaacca gtccagaagc tcattgaaga gatgaaccct     360
cgaccaagct gtctaatttc tgattttgt ttgccttata caagcaaaat cgccaagaag     420
ttcaatatcc caaagatcct cttccatggc atgggttgct tttgtcttct gtgtatgcat     480
gttttacgca agaaccgtga gatcttggac aatttaaagt cagataagga cttttcact      540
gttcctgatt tcctgatag agttgaattc acaagaacgc aagttccggt agaaacatat     600
gttccagctg gagactggaa agatatcttt gatggtatgg tagaagcgaa tgagacatct     660
tatggtgtga tcgtcaactc atttcaagag ctcgagcctg cttatgccaa agactacaag     720
gaggtaaggt ccggtaaagc atggaccatt ggacccgttt ccttgtgcaa caaggtagga     780
gccgacaaag cagagagggg aaacaaatca gacattgatc aagatgagtg ccttaaatgg     840
ctcgattcta gaaacatgg ctcggtgctt acgtttgtc ttggaagtat ctgtaatctt      900
cctttgtctc aactcaagga gctgggacta ggcctagagg aatcccaaag acctttcatt     960
tgggtcataa gaggttggga aagtacaaa gagttagttg agtggttctc ggaaagcggc    1020
tttgaagata gaatccaaga tagaggactt ctcatcaaag gatggtcccc tcaaatgctt    1080
atcctttcac atccatcagt tggagggttc ctaacacact gtggttggaa ctcgactctt    1140
gaggggataa ctgctggtct accgctactt acatggccgc tattcgcaga ccaattctgc    1200
aatgagaaat tggtcgttga ggtactaaaa gccggtgtaa gatccggggt tgaacagcct    1260
atgaaatggg gagaagagga gaaaatagga gtgttggtgg ataaagaagg agtgaagaag    1320
gcagtggaag aattaatggg tgagagtgat gatgcaaaag agagaagaag aagagccaaa    1380
gagcttggag attcagctca caaggctgtg aagaaggag gctcttctca ttctaacatc    1440
tctttcttgc tacaagacat aatggaactg cagaaccca ataattga                  1488
```

<210> SEQ ID NO 29
<211> LENGTH: 495
<212> TYPE: PRT
<213> ORGANISM: Arabidopsis thaliana

<400> SEQUENCE: 29

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

-continued

```
Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Ala Lys Glu Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 30
<211> LENGTH: 2757
<212> TYPE: DNA
<213> ORGANISM: Arabidopsis thaliana

<400> SEQUENCE: 30
atgggatctc agatcattca taactcacaa aaaccacatg tagtttgtgt tccatatccg      60
gctcaaggcc acatcaaccc tatgatgaga gtggctaaac cctccacgc cagaggcttc     120 tacgtcacct tcgtcaacac cgtctacaac cacaatcgtt tccttcgttc tcgtgggtcc    180
aatgccctag atggacttcc ttcgttccga tttgagtcca ttgctgacgg tctaccagag    240
acagacatgg atgccacgca ggacatcaca gctctttgcg agtccaccat gaagaactgt    300
ctcgctccgt tcagagagct tctccagcgg atcaacgctg gagataatgt tcctccggta    360
agctgtattg tatctgacgg ttgtatgagc tttactcttg atgttgcgga ggagcttgga    420
gtcccggagg ttcttttttg acaaccagt ggctgtgcgt tcctggctta tctacacttt     480
tatctcttca tcgagaaggg cttatgtccg ctaaaggta cgtattctta cattgattat     540
tgatttaaat gacgttatga tattaaattt aacgtaagaa cccttaagac acctcgagca    600
gggtgagttt ttaatctgag atatatcgtt tgtatattgg ataaaaaata tccatttagc    660
taccatattt agcgaagcca tagactatcc taatcgatcc acccgcacga cgagaccggt    720
caagactcaa gatggtcatg ttgtaatata tactcaattt tatacaattg ttacattgta    780
gcctaggttt tgagcatta ctaaatatat agtatcaaga gaaatgtcca tattttaata     840
tatacataac gtaatgaatg ttttgatatg ttttttatt cgatgcgttt gcagttttct     900
tgtaatatat atattacagt tttcttagcc aaaaaaaaa taataatta gagaagatac      960 attgttgatt tattttaaag cattgatatc tttttaacct tccgcttccc ctatccgctg   1020
gtgaattttg agtgacatta aagattgaac agaaatccca tatttatttt tgttaagaga   1080
tgcgtagatt cttaactttg attacagttt aaaatcatgt taaggaaat gatgatgttc    1140 aaaattccat ttcgtatttt acataaattt tgttgttaac ttatcttaaa gttatatgat   1200
atttgcaaac gtcgtctttc tatgattttt attattagtt tgaacgtaaa caaaatatat   1260
ttaatatttg tgaaaggct tgaaaattgt aaaagaggga ttttaaata gtaacaaatt     1320 ttaggtgaac tatagcgtat ataaaagata ggttatttat ttgtgtaaag attatctgtt   1380
tgtattggtt ccaattttt tcggtgacct ttaataacat agatgcatca cacatgaaca    1440
tttggtatga aaacaaaaag ataaccaata ttgccaaaaa aaaagaagg agagagacgg    1500
```

```
cgggaaagtt tgttgaggaa aaaaataaaa ttgggtaata tccaaacatg aaagtgaaat    1560
aaaccgtaaa aaatcaatgc aatttggcat atcattgtcc agggaccagg ccactctgtc    1620
tttcggtcat attcataact ctttctggct ctgaaattac acaatgaatg ccgtgtccta    1680
gagaatcata tagacgtgga tgcttacgta aatgcataat tttttctaaa atgcggtgct    1740
tgtattttta ttaactaata tcatgagact tatcttgatt aataaatggt gattgatttg    1800
gcagatgaga gttacttgac gaaggagtac ttagaagaca cggttataga ttttatacca    1860
accatgaaga atgtgaaact aaaggatatt cctagcttca tacgtaccac taatcctgat    1920
gatgttatga ttagtttcgc cctccgcgag accgagcgag ccaaacgtgc ttctgctatc    1980
attctaaaca catttgatga ccttgagcat gatgttgttc atgctatgca atctatctta    2040
cctccggttt attcagttgg accgcttcat ctcttagcaa accgggagat tgaagaaggt    2100
agtgagattg gaatgatgag ttcgaattta tggaaagagg agatggagtg tttggattgg    2160
cttgatacta agactcaaaa tagtgtcatt tatatcaact tgggagcat  aacggttttg    2220 agtgtgaagc agcttgtgga gtttgcttgg ggtttggcgg aagtgggaa  agagttttta    2280 tgggtgatcc ggccagattt agtagcggga gaggaggcta tggttccgcc ggacttttta    2340
atggagacta aagaccgcag tatgctagcg agttggtgtc ctcaagagaa agtactttct    2400
catcctgcta ttgagggggtt tttgacgcat tgcgggtgga actcgatatt ggaaagtctt    2460
tcgtgtggag ttccgatggt gtgttggcca ttttttgctg accagcaaat gaattgtaag    2520
ttttgttgtg acgagtggga tgtttgggatt gagataggtg gagatgtgaa gagagaggaa    2580
gttgaggcgg tggttagaga gctcatggat ggagagaagg gaaagaaaat gagagaaaag    2640
gcggtagagt ggcagcgctt agccgagaaa gcgacggaac ataaacttgg ttcttccgtt    2700
atgaattttg agacggttgt tagcaagttt cttttgggac aaaaatcaca ggattaa       2757

<210> SEQ ID NO 31
<211> LENGTH: 1470
<212> TYPE: DNA
<213> ORGANISM: Arabidopsis thaliana

<400> SEQUENCE: 31
atgggatctc agatcattca taactcacaa aaaccacatg tagtttgtgt tccatatccg      60
gctcaaggcc acatcaaccc tatgatgaga gtggctaaac tcctccacgc cagaggcttc     120
tacgtcacct tcgtcaacac cgtctacaac cacaatcgtt tccttcgttc tcgtgggtcc     180
aatgccctag atggacttcc ttcgttccga tttgagtcca ttgctgacgg tctaccagag     240
acagacatgg atgccacgca ggacatcaca gctctttgcg agtccaccat gaagaactgt     300
ctcgctccgt tcagagagct tctccagcgg atcaacgctg gagataatgt tcctccggta     360
agctgtattg tatctgacgg ttgtatgagc tttactcttg atgttgcgga ggagcttgga     420
gtcccggagg ttcttttttg gacaaccagt ggctgtgcgt tcctggctta tctacacttt     480
tatctcttca tcgagaaggg cttatgtccg ctaaagatg  agagttactt gacgaaggag     540
tacttagaag acacggttat agatttata  ccaaccatga gaatgtgaa  actaaaggat     600 attcctagct tcatacgtac cactaatcct gatgatgtta tgattagttt cgccctccgc     660
gagaccgagc gagccaaacg tgcttctgct atcattctaa acacatttga tgaccttgag     720
catgatgttg ttcatgctat gcaatctatc ttacctccgg tttattcagt tggaccgctt     780
catctcttag caaaccggga gattgaagaa ggtagtgaga ttggaatgat gagttcgaat     840
ttatggaaag aggagatgga gtgtttggat tggcttgata ctaagactca aaatagtgtc     900
```

-continued

```
atttatatca actttgggag cataacggtt ttgagtgtga agcagcttgt ggagtttgct   960
tggggtttgg cgggaagtgg gaaagagttt ttatgggtga tccggccaga tttagtagcg  1020
ggagaggagg ctatggttcc gccggacttt ttaatggaga ctaaagaccg cagtatgcta  1080
gcgagttggt gtcctcaaga gaaagtactt tctcatcctg ctattggagg gttttttgacg  1140 cattgcgggg ggaactcgat attggaaagt ctttcgtgtg gagttccgat ggtgtgttgg  1200
ccattttttg ctgaccagca aatgaattgt aagttttgtt gtgacgagtg ggatgttggg  1260
attgagatag gtggagatgt gaagagagag gaagttgagg cggtggttag agagctcatg  1320
gatggagaga agggaaagaa aatgagagaa aaggcggtag agtggcagcg cttagccgag  1380
aaagcgacgg aacataaact tggttcttcc gttatgaatt ttgagacggt tgttagcaag  1440 tttctttttgg gacaaaaatc acaggattaa                                   1470
```

<210> SEQ ID NO 32
<211> LENGTH: 489
<212> TYPE: PRT
<213> ORGANISM: Arabidopsis thaliana

<400> SEQUENCE: 32

```
Met Gly Ser Gln Ile Ile His Asn Ser Gln Lys Pro His Val Val Cys
1               5                  10                  15

Val Pro Tyr Pro Ala Gln Gly His Ile Asn Pro Met Met Arg Val Ala
            20                  25                  30

Lys Leu Leu His Ala Arg Gly Phe Tyr Val Thr Phe Val Asn Thr Val
        35                  40                  45

Tyr Asn His Asn Arg Phe Leu Arg Ser Arg Gly Ser Asn Ala Leu Asp
    50                  55                  60

Gly Leu Pro Ser Phe Arg Phe Glu Ser Ile Ala Asp Gly Leu Pro Glu
65                  70                  75                  80

Thr Asp Met Asp Ala Thr Gln Asp Ile Thr Ala Leu Cys Glu Ser Thr
                85                  90                  95

Met Lys Asn Cys Leu Ala Pro Phe Arg Glu Leu Leu Gln Arg Ile Asn
            100                 105                 110

Ala Gly Asp Asn Val Pro Pro Val Ser Cys Ile Val Ser Asp Gly Cys
        115                 120                 125

Met Ser Phe Thr Leu Asp Val Ala Glu Glu Leu Gly Val Pro Glu Val
    130                 135                 140

Leu Phe Trp Thr Thr Ser Gly Cys Ala Phe Leu Ala Tyr Leu His Phe
145                 150                 155                 160

Tyr Leu Phe Ile Glu Lys Gly Leu Cys Pro Leu Lys Asp Glu Ser Tyr
                165                 170                 175

Leu Thr Lys Glu Tyr Leu Glu Asp Thr Val Ile Asp Phe Ile Pro Thr
            180                 185                 190

Met Lys Asn Val Lys Leu Lys Asp Ile Pro Ser Phe Ile Arg Thr Thr
        195                 200                 205

Asn Pro Asp Asp Val Met Ile Ser Phe Ala Leu Arg Glu Thr Glu Arg
    210                 215                 220

Ala Lys Arg Ala Ser Ala Ile Ile Leu Asn Thr Phe Asp Asp Leu Glu
225                 230                 235                 240

His Asp Val Val His Ala Met Gln Ser Ile Leu Pro Pro Val Tyr Ser
                245                 250                 255

Val Gly Pro Leu His Leu Leu Ala Asn Arg Glu Ile Glu Glu Gly Ser
            260                 265                 270
```

```
Glu Ile Gly Met Met Ser Ser Asn Leu Trp Lys Glu Glu Met Glu Cys
        275                 280                 285

Leu Asp Trp Leu Asp Thr Lys Thr Gln Asn Ser Val Ile Tyr Ile Asn
        290                 295                 300

Phe Gly Ser Ile Thr Val Leu Ser Val Lys Gln Leu Val Glu Phe Ala
305                 310                 315                 320

Trp Gly Leu Ala Gly Ser Gly Lys Glu Phe Leu Trp Val Ile Arg Pro
                325                 330                 335

Asp Leu Val Ala Gly Glu Glu Ala Met Val Pro Pro Asp Phe Leu Met
                340                 345                 350

Glu Thr Lys Asp Arg Ser Met Leu Ala Ser Trp Cys Pro Gln Glu Lys
        355                 360                 365

Val Leu Ser His Pro Ala Ile Gly Gly Phe Leu Thr His Cys Gly Trp
        370                 375                 380

Asn Ser Ile Leu Glu Ser Leu Ser Cys Gly Val Pro Met Val Cys Trp
385                 390                 395                 400

Pro Phe Phe Ala Asp Gln Gln Met Asn Cys Lys Phe Cys Cys Asp Glu
                405                 410                 415

Trp Asp Val Gly Ile Glu Ile Gly Gly Asp Val Lys Arg Glu Glu Val
                420                 425                 430

Glu Ala Val Val Arg Glu Leu Met Asp Gly Glu Lys Gly Lys Lys Met
        435                 440                 445

Arg Glu Lys Ala Val Glu Trp Gln Arg Leu Ala Glu Lys Ala Thr Glu
        450                 455                 460

His Lys Leu Gly Ser Ser Val Met Asn Phe Glu Thr Val Val Ser Lys
465                 470                 475                 480

Phe Leu Leu Gly Gln Lys Ser Gln Asp
                485
```

US 7,662,583 B2

BIOREACTOR CONTAINING CELLS EXPRESSING GLYCOSYLTRANSFERASE NUCLEIC ACIDS ISOLATABLE FROM *ARABIDOPSIS*

REFERENCE TO RELATED APPLICATIONS

This is the U.S. National Stage of International Application No. PCT/GB2004/002237, filed May 24, 2004 (published in English under PCT Article 21(2)), which in turn claims the benefit of Great Britain patent application no. 0312042.5 filed May 27, 2003 and Great Britain patent application no. 0315183.4 filed Jun. 28, 2003.

FIELD OF THE INVENTION

We describe glycosyltransferase nucleic acids and proteins, transgenic cells expressing said glycosyltransferases and bioreactors comprising said transgenic cells.

BACKGROUND

Glycosyltransferases (GTases) are enzymes that post-translationally transfer glycosyl residues from an activated nucleotide sugar to monomeric and polymeric acceptor molecules such as other sugars, proteins, lipids and other organic substrates. These glucosylated molecules take part in diverse metabolic pathways and processes. The transfer of a glucosyl moiety can alter the acceptor's bioactivity, solubility and transport properties within the cell and throughout the plant. One family of GTases in higher plants is defined by the presence of a C-terminal consensus sequence. The GTases of this family function in the cytosol of plant cells and catalyse the transfer of glucose to small molecular weight substrates, such as phenylpropanoid derivatives, coumarins, flavonoids, other secondary metabolites and molecules known to act as plant hormones. Available evidence indicates that GTases enzymes can be highly specific, such as the maize and *Arabidopsis* GTases that glucosylate indole-3-acetic acid (IAA). We have also identified a family of Gtases which modifies abscisic acid, see WO03/023035.

Further examples of glycosyltransferases are described in the present application.

Cytokinins are plant hormones that have a structure which resembles adenine and which have various functions that include the stimulation of cell division. Cytokinins are found in most higher plants and in mosses, fungi, bacteria and in the transfer RNA of many eukaryotes and prokaryotes. There are over 200 different cytokinin compounds and are found in high concentrations in meristemic regions and areas of continuous growth, for example, roots, young leaves, developing fruits and seeds. The first cytokinin to be isolated from a plant source was called zeatin. In addition to stimulating cell division, cytokinins also stimulate morphogenesis in tissue culture, growth of lateral buds and leaf expansion as a result of cell growth. In some species cytokinins are involved in enhancing stomatal opening and promotes the conversion of etioplasts into chloroplasts by stimulation of chlorophyll synthesis. It is known that cytokinins can be modified by glucosylation.

GTases also have utility with respect to the modification of antioxidants. Reactive oxygen species are produced in all aerobic organisms during respiration and normally exist in a cell in balance with biochemical anti-oxidants. Environmental challenges, such as by pollutants, oxidants; toxicants, heavy metals and so on, can lead to excess reactive oxygen species which perturb the cellular redox balance, potentially leading to wide-ranging pathological conditions. In animals and humans, cardiovascular diseases, cancers, inflammatory and degenerative disorders are linked to events arising from oxidative damage. Because of the current prevalence of these diseases, there is considerable interest in anti-oxidants, consumed in the diet or applied topically such as in UV-screens.

Anti-oxidant micronutrients obtained from vegetables and fruits, teas, herbs and medicinal plants are thought to provide significant protection against health problems arising from oxidative stress. Well known anti-oxidants from plant tissues include for example: quercetin, luteolin, and the catechin, epicatechin and cyanidin groups of compounds. Caffeic acid (3,4-dihydroxycinnamic acid) is a further example of an anti-oxidant with beneficial therapeutic properties. Certain plant species, organs and tissues are known to have relatively high levels of one or more compounds with anti-oxidant activity. Greater accumulation of these compounds in those species, their wider distribution in crop plants, and plant parts already used for food and drink production, and the increased bio-availability of anti-oxidants (absorption, metabolic conversions and excretion rate) are three features considered to be highly desirable.

Bioreactors, for example fermentors, are vessels that comprise cells or enzymes and typically are used for the production of molecules on an industrial scale. The molecules can be recombinant proteins (e.g. enzymes such as proteases, lipases, amylases, nucleases, antibodies) or compounds that are produced by the cells contained in the vessel or via enzyme reactions that are completed in the reaction vessel. Typically, cell based bioreactors comprise the cells of interest and include all the nutrients and/or co-factors necessary to carry out the reactions.

We disclose in the present application GTases that modify compounds (e.g. cytokinins, quercetin) in a stereospecific fashion (i.e. a family of GTases which can label cytokinins or quercetin with a high degree of specificity). Moreover we disclose an in vitro cell based bioreactor that utilises these glycosyltransferases to add glucosyl moieties to these compounds.

Surprisingly we find that the bioreactor does not require an exogenous supply of UDP-glucose, (a substrate for these enzymes). We show that this is a general principle for plant GTases and applicable to any cell based bioreactor comprising transgenic cells that have been transformed with plant GTases. In our co-pending applications WO01/59140, WO02/103022, WO 03/023035 we disclose GTase sequences with substrate specificity for a range of small molecules, these sequences are specifically incorporated by reference into the current application with respect to the bioreactor embodiment.

SUMMARY

According to an aspect of the invention there is provided a reaction vessel comprising a genetically modified cell wherein said cell has been modified by transfection or transformation with a nucleic acid molecule which encodes a plant glycosyltransferase wherein said vessel includes nutrient medium for supporting the growth of said cell characterised in that said nutrient media does not include an exogenous supply of UDP glucose.

According to an aspect of the invention there is provided a reaction vessel comprising, a genetically modified cell wherein said cell is modified by transfection or transformation with a nucleic acid molecule selected from the group consisting of;

i) a nucleic acid molecule comprising a nucleic acid sequence as represented in FIGS. 1a, 2a, 3a, 4a, 4b, 5a, 5b, 6a, 6b, 7a, 7b, 8a, 8b, 9a, 9b, 10a, 10b, 11a, 12a and 12b;

ii) a nucleic acid molecule that hybridises to the sequences represented in (i) above and which encode a polypeptide that has glycosyltransferase activity;

iii) a nucleic acid molecule comprising a nucleic acid sequence that is degenerate as a result of the genetic code to the sequences defined in (i) and (ii) above; nutrient medium for supporting the growth of said cell that includes at least one exogenous substrate which is a substrate for said glycosyltransferase, characterised in that said nutrient medium does not include an exogenous supply of UDP-glucose.

In a preferred embodiment of the invention said vessel is a bioreactor.

In a further preferred embodiment of the invention said nutrient media does not include an exogenous supply of UDP-glucose.

In a further preferred embodiment of the invention said nucleic acid molecules hybridise under stringent hybridisation conditions to the sequences presented in 1a, 2a, 3a, 4a, 4b, 5a, 5b, 6a, 6b, 7a, 7b, 8a, 8b, 9a, 9b, 10a, 10b, 11a, 12a and 12b.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequence of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m = 81.5° C. + 16.6 \text{ Log } [Na^+] + 0.41[\% \text{ }G+C] - 0.63 \text{ (\% formamide)}.$$

Typically, hybridisation conditions uses 4-6×SSPE (20× SSPE contains 175.3 g NaCl, 88.2 g $NaH_2PO_4H_2O$ and 7.4 g EDTA dissolved to 1 litre and the pH adjusted to 7.4); 5-10× Denhardts solution (50×Denhardts solution contains 5 g Ficoll (type 400, Pharmacia), 5 g polyvinylpyrrolidone and 5 g bovine serum albumen; 100 μg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42°-65° C.

In a further preferred embodiment of the invention said cell is transformed or transfected with a vector comprising said nucleic acid molecule.

In a further preferred method of the invention said vector is an expression vector conventionally adapted for eukaryotic or prokaryotic gene expression.

Typically said adaptation includes, by example and not by way of limitation, the provision of transcription control sequences (promoter sequences) that mediate cell specific expression. These promoter sequences may be dell specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors which have been shown to bind specifically to enhancer elements. The binding/activity of transcription factors (please see Eukaryotic Transcription Factors, by David S Latchman, Academic Press Ltd, San Diego) is responsive to a number of environmental cues that include, by example and not by way of limitation, intermediary metabolites (e.g. sugars), environmental effectors (e.g. light, heat).

Promoter elements also include so called TATA box and RNA polymerase initiation selection (RIS) sequences that function to select a site of transcription initiation. These sequences also bind polypeptides that function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors that are maintained autonomously are referred to as episomal vectors. Episomal vectors are desirable since these molecules can incorporate large DNA fragments (30-50 kb DNA). Episomal vectors of this type are described in WO98/07876.

Adaptations which facilitate the expression of vector encoded genes include the provision of transcription termination/polyadenylation sequences. This also includes the provision of internal ribosome entry sites (IRES) that function to maximise expression of vector encoded genes arranged in bicistronic or multi-cistronic expression cassettes.

Expression control sequences also include so-called Locus Control Regions (LCRs). These are regulatory elements that confer position-independent, copy number-dependent expression to linked genes when assayed as transgenic constructs in mice. LCRs include regulatory elements that insulate transgenes from the silencing effects of adjacent heterochromatin, Grosveld et al., Cell (1987), 51: 975-985.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

In a preferred embodiment of the invention said cell is transfected or transformed with a nucleic acid molecule which encodes a polypeptide as represented by the amino acid sequence represented in FIGS. 1b, 2b, 3b, 4c, 5c, 6c, 7c, 8c, 9c, 10c, 11b, or 12c, or a variant polypeptide wherein said variant is modified by addition, deletion or substitution of at least one amino acid residue.

A variant polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants which retain or enhance the same biological function and activity as the reference polypeptide from which it varies, for example a polypeptide which has improved glycosyltransferase activity. A functionally equivalent polypeptide is a variant wherein one in which one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxyl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features polypeptide sequences having at least 75% identity with the polypeptide sequences as herein disclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated herein and which retain or has enhanced glycosyltransferase activity.

According to a further aspect of the invention there is provided a transgenic cell wherein said cell is transfected or transformed with a nucleic acid molecule comprising a nucleic acid sequence selected from the group consisting of:
 i) a nucleic acid molecule consisting of a nucleic acid sequence as represented in FIGS. 1*a*, 2*a*, 3*a*, 4*a*, 4*b*, 5*a*, 5*b*, 6*a*, 6*b*, 7*a*, 7*b*, 8*a*, or 8*b*;
 ii) a nucleic acid molecule which hybridises to the nucleic acid molecules in (i) and which have glycosyltransferase activity wherein said activity is the glucosylation of an anti-oxidant;
 iii) a nucleic acid molecule consisting of a nucleic acid sequence which is degenerate as a result of the genetic code to the sequences defined in (i) and (ii) above.

In a preferred embodiment of the invention said nucleic acid molecule hybridises under stringent hybridisation conditions to the sequences presented in FIGS. 1*a*, 2*a*, 3*a*, 4*a*, 4*b*, 5*a*, 5*b*, 6*a*, 6*b*, 7*a*, 7*b*, 8*a*, or 8*b*.

In a further preferred embodiment of the invention said anti-oxidant is quercetin.

In an alternative preferred embodiment of the invention said anti-oxidant is esuletin.

According to a yet further aspect of the invention there is provided a vector comprising a nucleic acid molecule wherein said molecule is selected from the group consisting of:
 i) a nucleic acid molecule consisting of a nucleic acid sequence as represented in FIGS. 1*a*, 2*a*, 3*a*, 4*a*, 4*b*, 5*a*, 5*b*, 6*a*, 6*b*, 7*a*, 7*b*, 8*a*, or 8*b*;
 ii) a nucleic acid molecule which hybridises to the nucleic acid molecules in (i) and which have glycosyltransferase activity wherein said activity is the glucosylation of an anti-oxidant;
 iii) a nucleic acid molecule consisting of a nucleic acid sequence which is degenerate as a result of the genetic code to the sequences defined in (i) and (ii) above.

According to a further aspect of the invention there is provided a transgenic cell wherein said cell is transfected or transformed with a nucleic acid molecule comprising a nucleic acid sequence selected from the group consisting of:
 i) a nucleic acid molecule consisting of a nucleic acid sequence as represented in FIGS. 9*a*, 9*b*, 10*a*, 10*b*, 11*a*, 12*a* and 12*b*;
 iii) a nucleic acid molecule which hybridises to the nucleic acid molecules in (i) and which have glycosyltransferase activity wherein said activity is the glucosylation of a cytokinin;
 iii) a nucleic acid molecule consisting of a nucleic acid sequence which is degenerate as a result of the genetic code to the sequences defined in (i) and (ii) above.

In a preferred embodiment of the invention said nucleic acid molecule hybridises under stringent hybridisation conditions to the sequences represented in FIGS. 9*a*, 9*b*, 10*a*, 10*b*, 11*a*, 12*a* and 12*b*.

In a preferred embodiment of the invention said cytokinin is selected from the group consisting of: trans-Zeatin; dihydrozeatin; N6-isopentenyladenine; N6-benzyladenine and kinetin.

According to a yet further aspect of the invention there is provided a vector comprising a nucleic acid molecule wherein said molecule is selected from the group consisting of:
 i) a nucleic acid molecule consisting of a nucleic acid sequence as represented in FIGS. 9*a*, 9*b*, 10*a*, 10*b*, 11*a*, 12*a* and 12*b*;
 ii) a nucleic acid molecule which hybridises to the nucleic acid molecules in (i) and which have glycosyltransferase activity wherein said activity is the glucosylation of a cytokinin; and
 iii) a nucleic acid molecule consisting of a nucleic acid sequence which is degenerate as a result of the genetic code to the sequences defined in (i) and (ii) above.

In a preferred embodiment of the invention said cell is a eukaryotic cell. Preferably said cell is selected from the group consisting of: a yeast cell; an insect cell; a mammalian cell or a plant cell.

In a preferred embodiment of the invention said cell is a plant cell.

In a preferred embodiment of the invention said plant cell is selected from: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassaya (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plant cells of the present invention are crop plant cells (for example, cereals and pulses, maize, wheat, potatoes, tapioca, rice, sorghum, millet, cassaya, barley, pea, and other root, tuber or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, chrysanthemum.

Grain plants that provide seeds of interest include oil-seed plants and leguminous plants. Seeds of interest include grain seeds, such as corn, wheat, barley, rice, sorghum, rye, etc.

Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava been, lentils, chick pea.

In a preferred embodiment of the invention said cell is a prokaryotic cell.

According to a further aspect of the invention there is provided a seed comprising a cell according to the invention.

According to a further aspect of the invention there is provided a method to glucosylate an anti-oxidant comprising: providing a cell according to the invention and nutrient medium to support the growth of said cell in a reaction vessel according to the invention and growth conditions conducive to the culturing of said cell.

In a preferred method of the invention said nutrient medium does not include an exogenous supply of UDP glucose.

In a further preferred method of the invention said anti-oxidant is quercetin or esuletin.

According to a further aspect of the invention there is provided a method to glucosylate a cytokinin comprising: providing a cell according to the invention and nutrient medium to support the growth of said cell in a reaction vessel according to the invention and growth conditions conducive to the culturing of said cell.

In a preferred method of the invention said medium does not include UDP glucose.

In a further preferred method of the invention said cytokinin is selected from the group consisting of: trans-Zeatin; dihydrozeatin; N6-isopentenyladenine; N6-benzyladenine and kinetin.

BRIEF DESCRIPTION OF THE FIGURES

An embodiment of the invention will now be described by example only and with reference to the following figures:

FIG. 1a UGT71B8 nucleic acid sequence (SEQ ID NO: 1); FIG. 1b amino acid sequence (SEQ ID NO: 2);

FIG. 2a UGT71C3 nucleic acid sequence (SEQ ID NO: 3); FIG. 2b amino acid sequence (SEQ ID NO: 4);

FIG. 3a UGT71C4 nucleic acid sequence (SEQ ID NO: 5); FIG. 3b amino acid sequence (SEQ ID NO: 6);

FIG. 4a UGT88A1 genomic nucleic acid sequence (SEQ ID NO: 7); FIG. 4b cDNA sequence (SEQ ID NO: 8); FIG. 4c amino acid sequence (SEQ ID NO: 9);

FIG. 5a UGT78D2 genomic sequence (SEQ ID NO: 10); FIG. 5b cDNA sequence (SEQ ID NO: 11); FIG. 5c amino acid sequence (SEQ ID NO: 12);

FIG. 6a UGT78D3 genomic sequence (SEQ ID NO: 13); FIG. 6b cDNA sequence (SEQ ID NO: 17); FIG. 6c amino acid sequence (SEQ ID NO: 18);

FIG. 7a UGT76D1 genomic sequence (SEQ ID NO: 16); FIG. 7b cDNA sequence (SEQ ID NO: 17); FIG. 7c amino acid sequence (SEQ ID NO: 18);

FIG. 8a UGT76E2 genomic sequence (SEQ ID NO: 19); FIG. 8b cDNA sequence (SEQ ID NO: 20); FIG. 8c amino acid sequence (SEQ ID NO: 21);

FIG. 9a UGT76C1 genomic sequence (SEQ ID NO: 22); FIG. 9b cDNA sequence (SEQ ID NO: 23; FIG. 9c amino acid sequence (SEQ ID NO: 24);

FIG. 10a UGT76C2 genomic sequence (SEQ ID NO: 25); FIG. 10b cDNA sequence (SEQ ID NO: 26); FIG. 10c amino acid sequence (SEQ ID NO: 27);

FIG. 11a UGT73C5 genomic sequence (SEQ ID NO: 28); FIG. 11b amino acid sequence (SEQ ID NO: 29);

FIG. 12a UGT 85A1 genomic sequence (SEQ ID NO: 30); FIG. 12b cDNA sequence (SEQ ID NO: 31); FIG. 12c amino acid sequence (SEQ ID NO: 32);

Figure 13A:
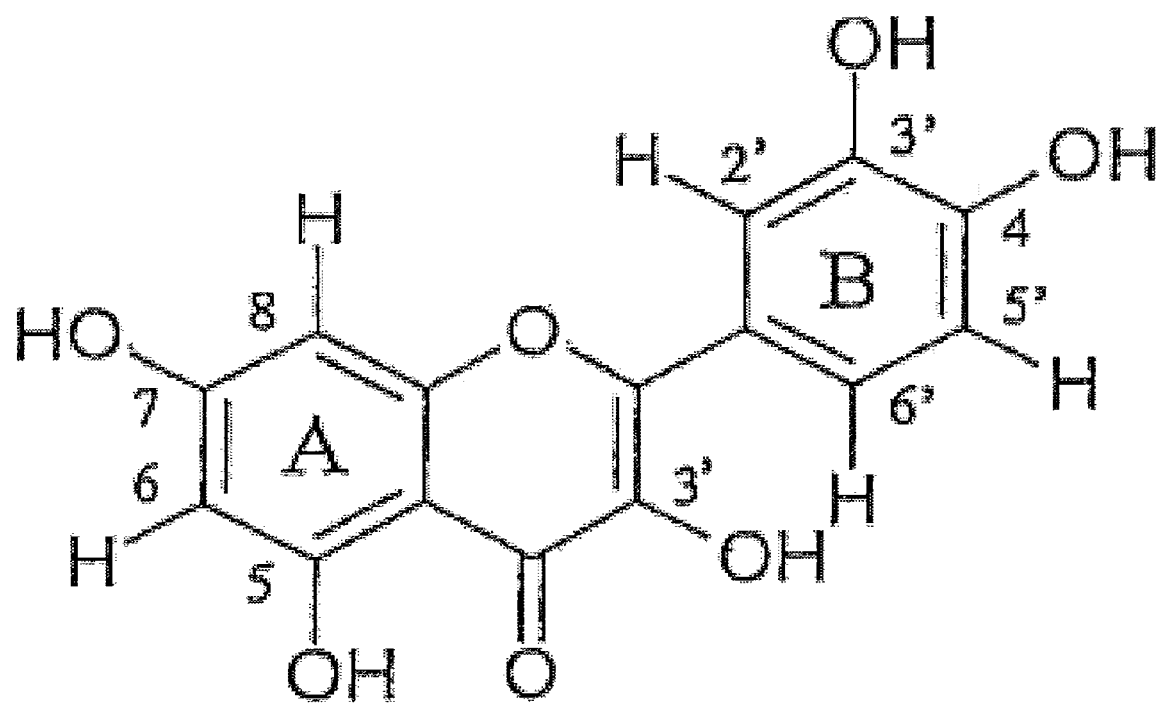
FIG. 13 Quercetin and its monoglucosides. (A) The chemical structure of quercetin. (B) Quercetin and its glucosides, separated by HPLC as described in Experimental Protocol, using an absorption wavelength of 370 nm. The identity of the monoglucosides confirmed using NMR are: (1) quercetin-7-O-glucoside, (2) quercetin-3-O-glucoside, (3) quercetin-4'-O-glucoside, (4) quercetin-3'-O-glucoside. (1-3) were prepared using recombinant enzyme UGT89B1; (4) was prepared using recombinant enzyme UGT71C1.
FIG. 13C illustrates detailed analysis of 4 UGT's able ability to glucosylate multiple hydroxyl groups of quercetin.

Table 1A describes the regioselectivity (site modification specificity) of GTases with respect to the modification of quercetin. The GTases are either described in this present application or in WO01/59140 the sequences of which are incorporated by reference. Table 1B shows NMR spectral data of quercetin and its glucosides;

Table 2A summarises the modification of quercetin by bacteria transformed with various GTase nucleic acids; Table 2B shows NMR spectral data of quercetin-7,3'-di-O-glucoside and quercetin 3',7-di-O-glucoside;

Table 3 illustrates the effect of glucose on whole cell biocatalyst of quercetin;

Materials and Methods

Whole-Cell Bioreactor Assay in Fermentor System

A 6 L glass autoclavable fermentor system (Applikon Biotechnology Ltd.) was used for large-scale analysis of UGT whole-cell biocatalysts. E. coli BL21 overnight culture (40 ml) expressing UGT was transferred into the fermentor system containing 2 L of LB medium previously equilibrated at 30° C., pH 7.4. The dissolved $O_2$ level was maintained at 95% for 1 h and was decreased to 60% throughout the remaining process. When the culture reached an optical density at 0.2, the temperature was lowered to 20° C. 0.1 mM of isopropyl-1-thio-β-D-galactopyranoside and 2 g of quercetin were added after the bacterial culture reached an optical density at 0.6. Samples were harvested at intervals and the bacterial cells were removed by centrifugation. The resulting supernatant fractions (culture medium) were analysed with HPLC.

Conditions to be Optimised for Individual UGT Whole-Cell Biocatalyst

There are various conditions that could affect the efficiency of the biocatalysts. These include the temperature of the fermentor, the dissolved oxygen levels and the pH in the culture medium, the concentration of substrates applied as well as the solvent used to prepare the substrates.

Substrates that have been Tested with the UGT Whole-Cell Biocatalysts
1. quercetin
2. esculetin
3. trans-Zeatin
4. Dihydrozeatin
5. N6-Isopentenyladenine (iP)
6. N6-benzyladenine
7. Kinetin UGT Enzyme Reaction with Quercetin The assay mix (200 µl) contained 2 µg of recombinant protein, 100 mM Tris-HCl, pH 7.0, 5 mM UDP-glucose 1.4 mM 2-mercaptoethanol, and 0.5 mM of quercetin. The reaction was carried out at 30° C. for 1 h, and was quick-frozen and stored at −20° C. prior to the reverse-phase HPLC analysis UGT Enzyme Reaction with Cytokinins The assay mix (200 µl) contained 2 µg of recombinant protein, 100 mM Tris-HCl, pH 8.0, 5 mM UDP-glucose 0.5 mM ATP, 50 mM $MgCl_2$, and 0.5 mM of cytokinin. The reaction was carried out at 30° C. for 3 h, and was quick-frozen and stored at −20° C. prior to the reverse-phase HPLC analysis HPLC Analysis of the Reaction Mix Reverse-phase HPLC (SpectraSYSTEM HPLC systems and UV6000LP Photodiode Array Detector, ThermoQuest) analysis was carried using a Columbus 5µ $C_{18}$ column (250× 4.60 mm, PHENOMENEX). Quercetin glucosides were separated from the aglycone by a linear gradient of 10-75% acetonitrile in $H_2O$ (all solution contained 0.1% trifluoroacetic acid) at 1 ml/mm over 20 mm and monitored at 370 nm. Cytokinin glucosides were separated from their aglycone by a liner gradient of 10-100% methanol in $H_2O$ (for N6-isopentenyladenine (iP), N6-benzyladenine and kinetin) or 10-60% methanol in $H_2O$ (for trans-zeatin and dihydrozeatin) at 1 ml/min over 20 mm. All solution contained 0.25% acetic acid and 0.04% triethylamine, trifluoroacetic acid. The separation was monitored at 206 nm and 252 nm. The identity of the products was confirmed by comparison with authentic gluco sides.

Cytokinin Products Formed by the UGTs
1. 7-N-glucoside (76C1, 76C2)
2. 9-N-glucoside (76C1, 76C2)
3. O-glucoside (only apply to trans-Zeatin and dihydrozeatin) (85A1 for trans-Zeatin; 85A1 and 73C5 for dihydrozeatin)

Large Scale Fermentation

Fermentation is carried out in a seven litre fermenter (applicon bioconsole ADI 1025). The process takes place over three consecutive days. The following parameters are continuously monitored and controlled: temperature, pH, percentage $O_2$ saturation. After equilibration of the system, the LB growth medium is inoculated with 15 ml of starter culture. The substrate is added when the cells are induced with IPTG. Aliquots are withdrawn at regular intervals and the production of glycoside monitored by HPLC analysis.

The vessel is drained about 20 hours after induction and the culture is spun down in a Sorval Evolution RC, SLC6000 rotor. The supernatant is frozen prior to freeze drying.

The freeze dried material is resolubilised in water and repeatedly extracted in water-saturated butanol. The organic phases are pooled and the solvent evaporated off on a BUCHI R-114 rotavapor.

The extract is dissolved in 50% methanol prior to separation by preparative HPLC Column: PHENOMENEX Luna 5λ $C_{18}$(2), reverse phase 250×10 mm; volume 19.6 ml System used: AKTA FPLC system (Amersham Pharmacia Biotech) in TF.

The dissolved extract in 50% methanol is further diluted in 10% acetonitrile @ 0.1% trifluoro acetic acid (TFA) to a final concentration of ~5% methanol. Compounds are eluted off the column in isocratic step elutions at 15%, 35% and 50% acetonitrile @ 0.1% TFA. Peak fractions are collected and assayed by HPLC, LCMS and $^1H$ NMR.

EXAMPLE 1

Synthesis of Quercetin Glucosides In Vitro by Plant UGTs

Figure 13B:
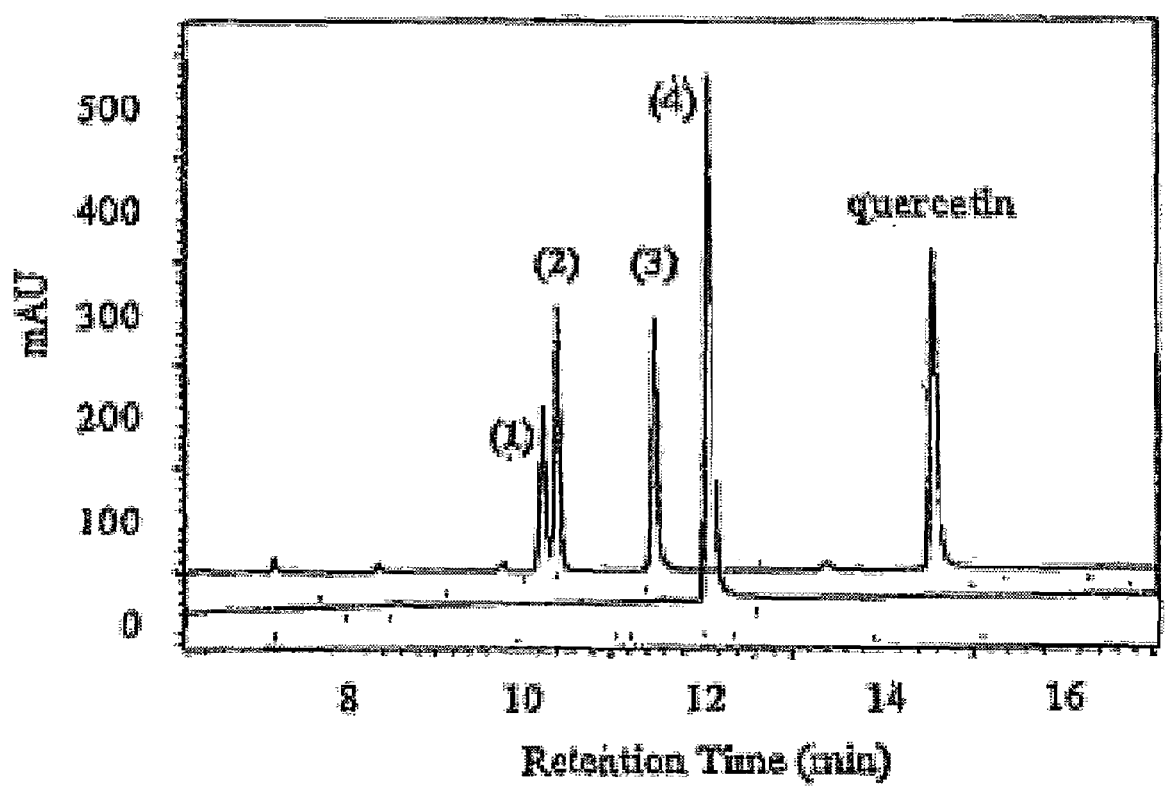

The activity of *Arabidopsis* recombinant UGTs towards quercetin was determined using the platform developed previously[15]. In total, only four major monoglucosides were observed in these data sets and their separation using reverse-phase HPLC is illustrated in FIG. 13B. The structures of these products were analysed using $^1H$ NMR and the spectra were compared with the published data[17]; the products were confirmed as the 3-O-, 7-O-, 3'-O- and 4'-O-monoglucoside of quercetin (see Table 1B). No significant activity towards the C5-OH was observed by any of the recombinant enzymes assayed. Of the 91 recombinant UGTs assayed, 29 enzymes expressed significant catalytic activity towards quercetin and the details are given in Table 1A. As summarised in the Table, there was further selectivity of glucosylation of the substrate. Fourteen enzymes recognised only a single site on quercetin, 12 of those glucosylating the C3-OH whilst 2 UGTs glucosylated the C7-OH. Fifteen enzymes were found to glucosylate two or more sites, with 11 recognising only two sites, and 3 recognising three sites. One UGT was found to be capable of glucosylating all four sites.

Figure 13C:
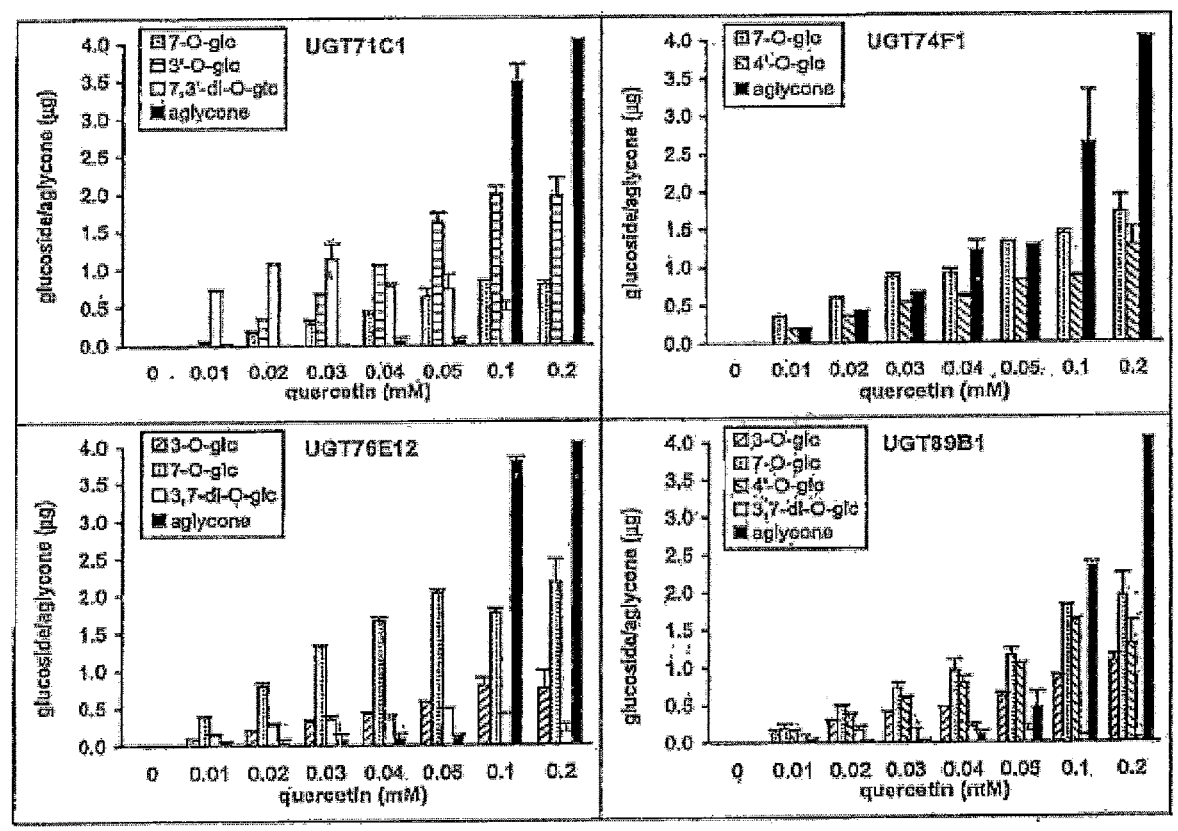

Given some of the UGTs recognised multiple sites on quercetin, it was important to determine whether only monoglucosides could be produced or whether multiple hydroxyl groups on the same molecule could be glucosylated if the reaction conditions were appropriate. Four UGTs, UGT71C1, UGT74F1, UGT76E12 and UGT89B1, were used to explore this possibility. In summary, di-O-glucoside formation was observed but only at low substrate concentration. Interestingly, out of four possible di-O-glucoside and one tri-O-glucoside, only two products were found, the 3,7-di-O-glucoside and the 7,3'-di-O-glucoside (see FIG. 13C). The 7,3'-di-O-glucoside was confirmed by $^1H$ NMR whilst the 3,7-di-O-glucoside was confirmed by $^1H$ NMR and LC-MS (see Table 2B and FIG. 14B). These data indicate that the products of the UGT catalysis will change under different reaction conditions. This offers a potential means of synthesising a wide range of different glucoside compounds.

As a further foundation for establishing a biocatalyst system, the time parameter was varied for two UGTs, UGT71C1 and UGT76E12 that each produced significant levels of di-O-glucosides. UGT71C1 rapidly converted the aglycone to monoglucosides that were then further consumed to produce the di-O-glucoside. In the UGT76E12 reaction mix, aglycone levels were depleted but the monoglucosides continued to remain at a constant level for many hours. These data indicate the reaction characteristics are dependent on the UGT used.

EXAMPLE 2

Plant UGTs as Whole-Cell Biocatalysts

Figure 14A:
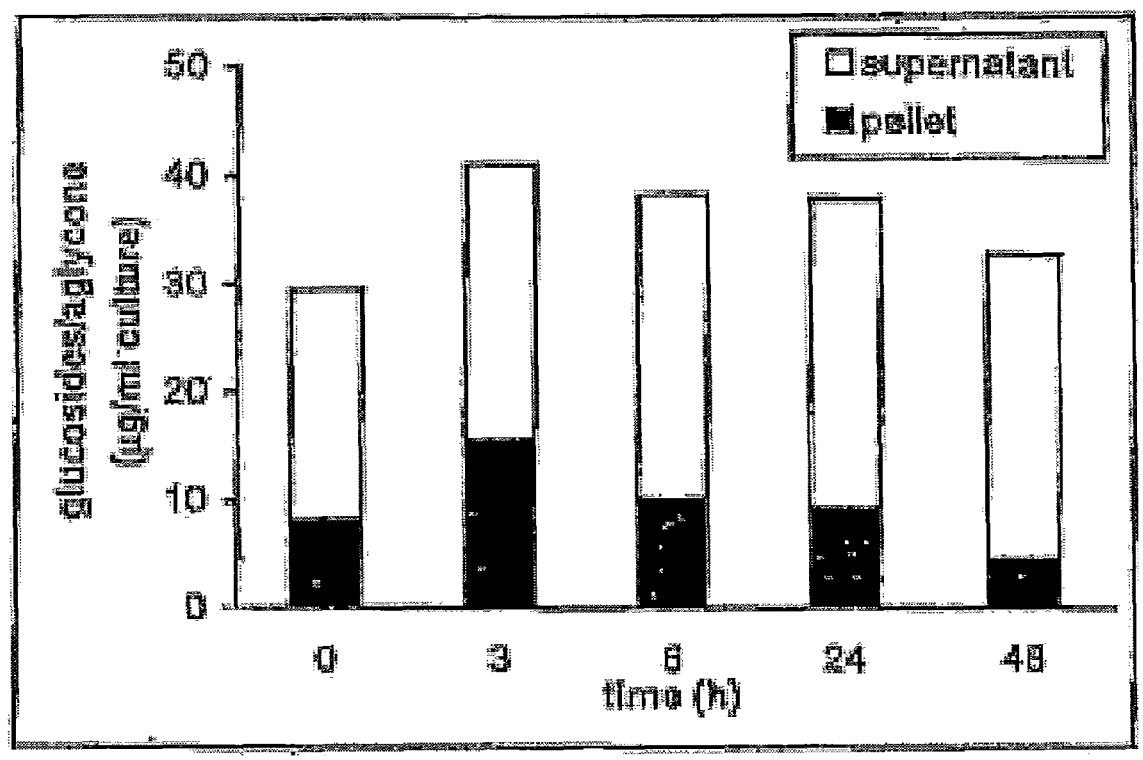
FIG. 14 Whole-cell biocatalyst assay using UGT71C1. E. coli cells expressing recombinant were used in the biocatalyst assay. After incubation with 0.1 mM quercetin and 0.1 mM IPTG, cells were collected by centrifugation, extracted with 80% methanol and both the cell extracts (pellet) and culture medium (supernatant) were analysed using HPLC. (A) Changes in the combined amounts of aglycone/glucoside over a time-course of 0-48 h. (B) Changes in the level of different glucosides and aglycone in the culture medium over the same time-course.
Figure 14B:
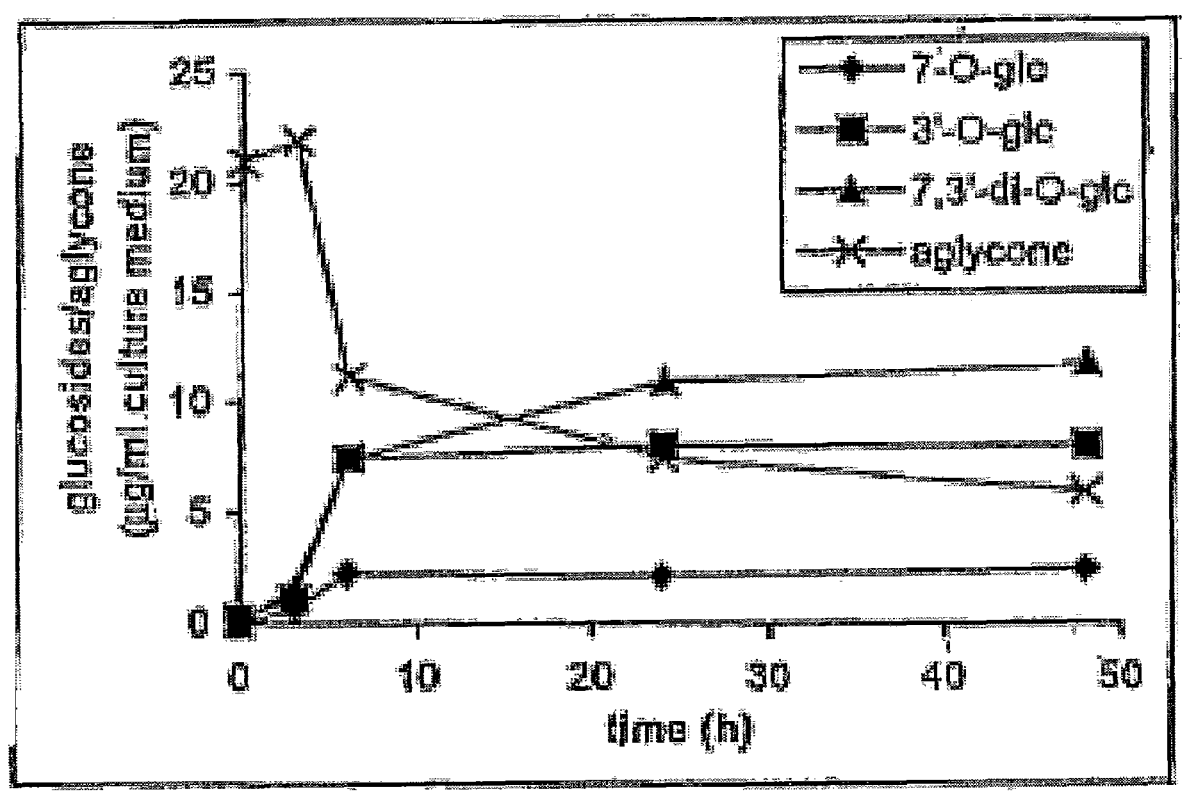

Using the foundation established in the preceding example, we went on to investigate the potential of *E. coli* expressing plant UGTs as whole-cell biocatalysts to synthesise glucosides of quercetin. In the first instance, we used *E. coli* grown in 75 ml of standard culture medium. Results of a preliminary set of experiments with the cells transformed with UGT71C1 are shown in FIG. 14. Interestingly, throughout a time-course of 48 h, the bulk of aglycone and glucosides were recovered in the culture medium (FIG. 14A) and within 6 h, ~50% of the aglycone was converted to glucosides (FIG. 14B). These studies showed that the cells in standard culture medium, in the absence of any supplementary UDP-glucose, were able to glucosylate substantial quantities of the added substrate. Table 2 describes results in which 7 different UGTs are expressed in *E. coli* and the identity and quantity of different glucosides recovered in the medium were analysed by HPLC. These data indicated that the patterns of regioselectivity of glucosylation in vivo closely mirrored those expressed by each UGT in vitro. There was considerable variation in the level of different glucosides synthesised by the cells, although even under these non-optimised conditions, each of the four monoglucosides and two di-O-glucosides could be formed.

To determine whether the cells could make the glucosides in a resting-state, the *E. coli* cells were transferred to phosphate buffer and cultured in the presence or absence of glucose. Results are shown in Table 3. In the absence of the energy source, negligible conversion of quercetin to its glucosides was observed. The aglycone was largely recovered from the cell pellet, implying uptake from the medium had occurred. In the presence of glucose, a higher level of compounds was recovered in the culture medium and of these, the bulk consisted of quercetin glucosides.

Figure 15A:
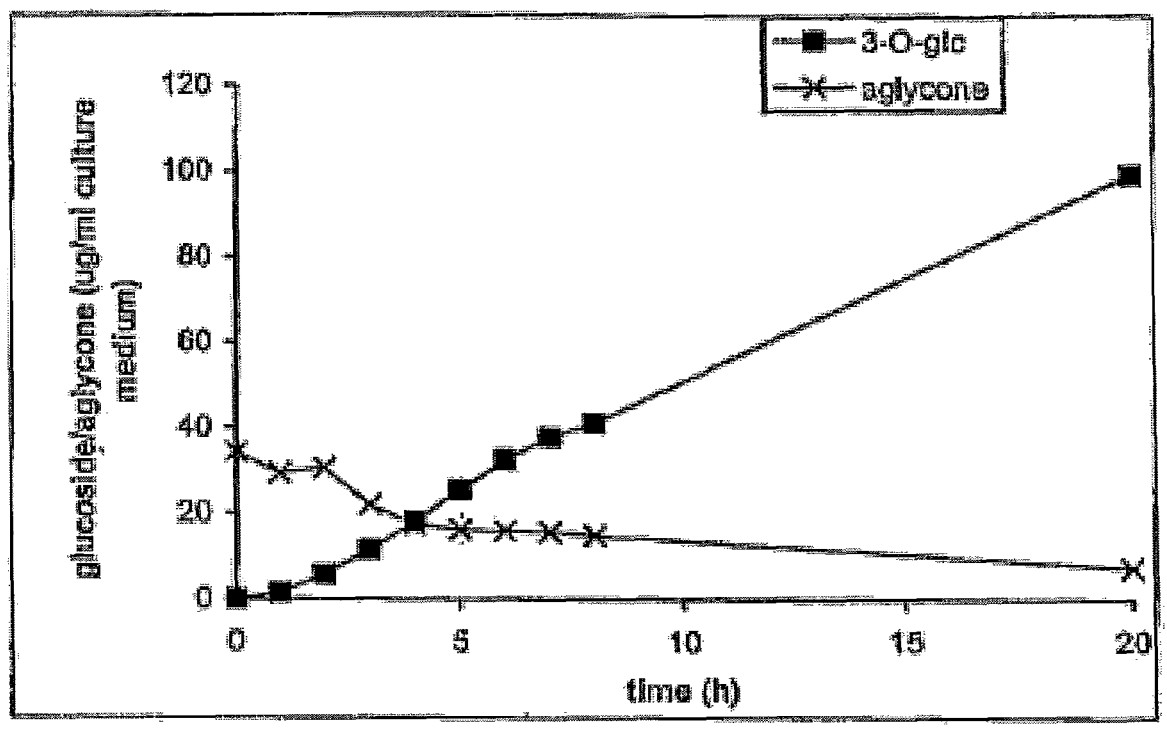
FIG. 15 fermenter-scale production of quercetin-3-O-glucoside using UGT73B3 as a whole-cell biocatalyst. (A) Changes in the level of quercetin-3-O-glucoside and aglycone in the culture medium over a time-course of 0-20 h. (B) HPLC analysis of the culture medium at 20 h: panel 1, prior to further extraction; panel 2, aqueous phase following extraction with water-saturated butanol; panel 3, organic phase following the above extraction. An absorption wavelength of 234 nm was used in the analyses.

In order to explore the potential of the whole-cell biocatalysts for large-scale production of glucosides in the absence of added UDP-glucose, transformed bacterial cells were cultured in a fermenter. This process enabled conditions to be controlled tightly throughout the production cycle and a direct comparison to be made of the efficiency of conversion of whole-cell UGT biocatalysis in a simple culture flask and an optimised fermenter system. UGT73B3 was chosen for the analysis, since preliminary experiments (Table 2) had shown formation of a single product, the 3-O-glucoside, at levels of 8.96 μg/ml following 24 h incubation. Using the fermenter system, the yield of 3-O-glucoside in the culture at 20 h was found to be 99.3 μg/ml i.e. 10-fold higher. These data are shown in FIG. 15A. The Figure also illustrates the final level of glucoside was much higher than the soluble aglycone at time 0 h. Quercetin is relatively insoluble under buffer conditions used and was therefore recovered as a precipitate in the centrifugation step prior to analysis of the supernatants. The data indicate that as the reaction proceeded increasing amounts of this quercetin became glucosylated.

Figure 15B:
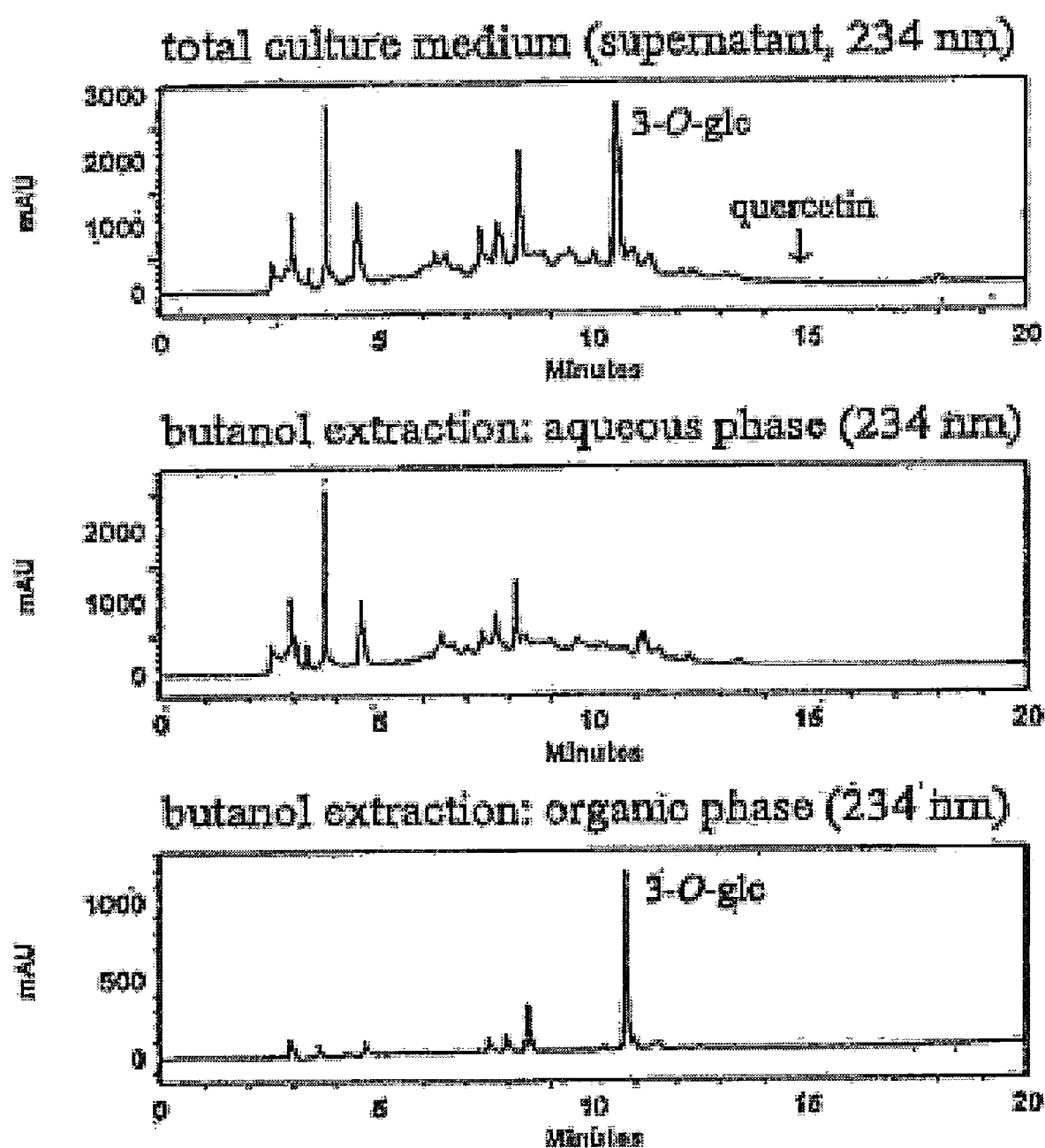

The glucoside produced by the UGT73B3 whole-cell biocatalyst can be readily purified from the culture medium by a one-step extraction with water-saturated butanol. As shown in FIG. 15B, the quercetin-3-O-glucoside was recovered in entirety into the organic phase, leaving the bulk of impurities in the aqueous phase.

This study demonstrates the utility of plant glycosyltransferases as biocatalysts in vitro and in vivo for the regioselective glucosylation of natural products. The use of the enzymes in vivo in *E. coli* has shown that there is no need to supplement the culture medium with UDP-glucose to achieve efficient conversion of substrate. Thus, the transformed cells can be used as a whole-cell and inexpensive biocatalyst system, particularly given that the products of the biotransformations are recovered from the culture medium. We have used quercetin as the model medicinal compound for this study because of the complexity of its glucosylation with 5 hydroxyl groups as potential sites for glucose attachment. Screening the 91 plant UGTs in vitro for activity against quercetin, revealed 29 that glucosylated the substrate either at one or more sites. The only site not recognised by the UGTs was the C5-OH. The dynamics of the reaction and recovery of the products indicated rapid intracellular glucosylation preceded secretion. The general utility of *E. Coli* for use with regioselective UGTs will depend on the ability of the cells to take up the substrate from the medium and, to a lesser extent, to secrete the products. The stability of both the substrate and the products will also be an important factor for success.

EXAMPLE 3

Fermentation

UGT73B3 plus 1.5 g quercetin were used for the production of quercetin-3-O-glucoside (Q-3-G). Following a 4 litre fermentation run, HPLC analysis of the crude supernatants was carried out to confirm production of Q-3-G. Purification of the Q-3-G was carried out following butanol extraction, solvent evaporation and resuspension of the extract in 50% methanol.

A number of separations, using 200 μl amounts of the dissolved extract made up to 2 ml in water, were carried out to determine optimum conditions. Several different gradients as well as a range of step elutions were investigated. The following solvent system was arrived at empirically: the dissolved extract in 50% methanol is further diluted in 10% acetonitrile @ 0.1% TFA to a final concentration of ~5% methanol. Compounds are eluted off the column in isocratic step elutions at 15%, 35% and 50% acetonitrile. Peak fractions are collected.

Half of the total amount, ie the equivalent of a 2 litre fermentation, was extracted into butanol and further purified as described above. Peak fractions were collected as well as all the flow through during loading.

Calculations based on HPLC analysis and comparison with a known commercial standard (Apin) allowed for an estimate of purity and yield: 55 mg of quercetin-3-O-glycoside at >95% purity The identity and purity of the Q-3-G were confirmed by $^1$H NMR and LC-MS.

EXAMPLE 4

UGT84B1 plus 0.5 g quercetin were used for the production of quercetin-7-O-glucoside (Q-7-G). Following a 2 litre fermentation run, HPLC analysis of the crude supernatants was carried out to confirm Q-7-G was produced. Purification of the Q-7-G was then carried out, following butanol extraction, solvent evaporation and resuspension of the extract in 50% methanol as for Q-3-G described above. Peak fractions were collected as well as all the flow through during loading.

Calculations based on HPLC analysis and comparison with a known commercial standard (Apin) allowed for an estimate of purity and yield: 8 mg of quercetin-7-O-glycoside at >90% purity

TABLE 1A

| Number of sites glucosylated | UGT | Group[a] | Specific activity (nkat/mg protein)[b] | | | | Enzymes analysed as biocatalysts[c] |
|---|---|---|---|---|---|---|---|
| | | | 3-O-glc | 7-O-glc | 3'-O-glc | 4'-O-glc | |
| 1 | 78D2 | F | 31.60 | — | — | — | * |
| 1 | 73B5 | D | 11.58 | — | — | — | |
| 1 | 71D1 | E | 4.19 | — | — | — | |
| 1 | 71B1 | E | 1.85 | — | — | — | |
| 1 | 73B3 | D | 1.57 | — | — | — | * |
| 1 | 73B2 | D | 0.92 | — | — | — | |
| 1 | 71C5 | E | 0.33 | — | — | — | |
| 1 | 71B5 | E | 0.26 | — | — | — | |
| 1 | 78D1 | F | 0.24 | — | — | — | |
| 1 | 72B3 | E | 0.20 | — | — | — | |
| 1 | 78D3 | F | 0.16 | — | — | — | |
| 1 | 71C3 | E | 0.11 | — | — | — | |
| 1 | 76D1 | H | — | 0.24 | — | — | |
| 1 | 84B1 | L | — | 0.14 | — | — | * |
| 2 | 73B4 | D | 12.14 | 0.18 | — | — | |
| 2 | 71C4 | E | 1.33 | 0.63 | — | — | |
| 2 | 76E12 | H | 1.16 | 1.35 | — | — | * |
| 2 | 73B1 | D | 0.32 | 0.14 | — | — | |
| 2 | 76E2 | H | 0.17 | 0.21 | — | — | |
| 2 | 76E11 | H | 0.08 | 0.12 | — | — | |
| 2 | 76E1 | H | 0.02 | 0.08 | — | — | |
| 2 | 71E8 | E | 0.31 | — | — | 0.25 | |
| 2 | 71C1 | E | — | 0.85 | 1.19 | — | * |
| 2 | 74F1 | L | — | 1.03 | — | 0.72 | * |
| 2 | 73C5 | D | — | 0.11 | — | 0.25 | |
| 3 | 71C2 | E | 0.16 | 0.24 | 0.03 | — | |
| 3 | 89B1 | B | 2.05 | 3.22 | — | 3.38 | * |
| 3 | 73C6 | D | 0.11 | 0.14 | — | 0.16 | |
| 4 | 88A1 | E | 0.41 | 0.19 | 0.19 | 0.76 | |

[a] The Group of each UGT as defined in the phylogenetic analysis of *Arabidopsis* UGTs[9,10]
[b] Specific activity, defined as nanomoles of quercetin glucosylated per second (nkat) by 1 mg of protein in 30 min of reaction. Activity lower than 0.02 nkat/mg protein has been considered as trace activity and is not shown in the Table.
[c] These UGTs were analysed further for their potential as whole-cell biocatalysts (see Table 2).

TABLE 1B

| Position | Quercetin | 7-O-glucoside | 3-O-glucoside | 4'-O-glucoside | 3'-O-glucoside |
|---|---|---|---|---|---|
| C6 | 6.17(1H, d, J = 2.5 Hz) | 6.46(1H, d, J = 2.0 Hz) | 6.20(1H, d, J = 2.0 Hz) | 6.16(1H, d, J = 2.0 Hz) | 6.18(1H, d, J = 2.0 Hz) |
| C8 | 6.38(1H, d, J = 2.0 Hz) | 6.76(1H, d, J = 2.0 Hz) | 6.39(1H, d, J = 2.0 Hz) | 6.36(1H, d, J = 2.0 Hz) | 6.45(1H, d, J = 2.0 Hz) |
| C2' | 7.72(1H, d, J = 2.0 Hz) | 7.76(1H, d, J = 2.0 Hz) | 7.70(1H, d, J = 2.0 Hz) | 7.76(1H, d, J = 2.0 Hz) | 8.13(1H, d, J = 2.0 Hz) |
| C5' | 6.88(1H, d, J = 8.5 Hz) | 6.88(1H, d, J = 8.5 Hz) | 6.86(1H, d, J = 8.5 Hz) | 7.30(1H, d, J = 9.0 Hz) | 6.97(1H, d, J = 8.5 Hz) |
| C6' | 7.62(1H, dd, J = 8.5, 2.0 Hz) | 7.61(1H, dd, J = 8.5, 2.0 Hz) | 7.58(1H, dd, J = 8.5, 2.0 Hz) | 7.71(1H, dd, J = 9.0, 2.0 Hz) | 7.87(1H, dd, J = 8.5, 2.0 Hz) |
| Glc-1 | — | 5.65(1H, d, J = 7.5 Hz) | 5.24(1H, d, J = 8.0 Hz) | 4.90(1H, d, J = 7.1 Hz) | 4.89(1H, d, J = 10.5 Hz) |
| Glc-2 | — | 3.33-3.49(4H, m) | 3.40-3.70(4H, m) | 3.25-3.55(4H, m) | 3.40-3.60(4H, m) |
| Glc-3 | — | | | | |
| Glc-4 | — | | | | |
| Glc-5 | — | | | | |
| Glc-6 | — | 3.92(1H, dd, J = 12.0, 2.0 Hz) | 3.70(1H, dd, J = 12.0, 2.0 Hz) | 3.92(1H, dd, J = 12.5, 2.0 Hz) | 3.92(1H, dd, J = 12.5, 2.0 Hz) |
| | | 3.68(1H, dd, J = 12.0, 5.5 Hz) | 3.56(1H, dd, J = 12.0, 5.0 Hz) | 3.73(1H, dd, J = 12.5, 5.0 Hz) | 3.73(1H, dd, J = 12.5, 5.0 Hz) |

Chemical shifts are given on ppm scale with TMS as internal standard. d = doublet; dd = doublet of doublet; m = multiplet; J = coupling constant.

TABLE 2A

| UGT | Number of products formed | Culture medium (μg/ml in supernatant) | | | | | |
|---|---|---|---|---|---|---|---|
| | | 3-O-glc | 7-O-glc | 3'-O-glc | 4'-O-glc | 3,7-di-O-glc | 7,3'-di-O-glc |
| 73B3 | 1 | 8.96 | — | — | — | — | — |
| 78D2 | 1 | 6.83 | — | — | — | — | — |
| 84B1 | 1 | — | 4.83 | — | — | — | — |
| 74F1 | 2 | — | 0.53 | — | 0.19 | — | — |
| 76E12 | 3 | 1.41 | 4.74 | — | — | 0.71 | — |

TABLE 2A-continued

| UGT | Number of products formed | Culture medium (µg/ml in supernatant) | | | | | |
|---|---|---|---|---|---|---|---|
| | | 3-O-glc | 7-O-glc | 3'-O-glc | 4'-O-glc | 3,7-di-O-glc | 7,3'-di-O-glc |
| 89B1 | 3 | 1.08 | 2.36 | — | 0.94 | — | — |
| 71C1 | 3 | — | 2.12 | 8.00 | — | — | 10.90 |

The *E. coli* culture was grown in 2x YT medium; when the $A_{600}$ reached 0.7, 0.1 mM IPTG and 0.1 mM quercetin were added; after 24 h, the culture was harvested, centrifuged and the levels of glucosides in the supernatant were analysed by HPLC.

TABLE 2B

| Position | Quercetin-7,3'-di-O-glucoside | Quercetin-3,7-di-O-glucoside |
|---|---|---|
| C6 | 6.45(1H, d, J = 2.0 Hz) | 6.50(1H, d, J = 2.0 Hz) |
| C8 | 6.87(1H, d, J = 2.0 Hz) | 6.76(1H, d, J = 2.0 Hz) |
| C2' | 8.17(1H, d, J = 2.0 Hz) | 7.72(1H, d, J = 2.0 Hz) |
| C5' | 6.91(1H, d, J = 8.0 Hz) | 6.87(1H, d, J = 8.5 Hz) |
| C6' | 7.93(1H, dd, J = 8.0, 2.0 Hz) | 7.62(1H, dd, J = 8.5, 2.0 Hz) |
| Glc-1 | | |
| Glc-2 | | |
| Glc-3 | N.D.[a] | N.D. |
| Glc-4 | | |
| Glc-5 | | |
| Glc-6 | | |

Chemical shifts are given on ppm scale with TMS as internal standard. d = doublet; dd = doublet of doublet; m = multiplet; J = coupling constant.
[a]N.D., not determined. The signals of the glucose molecule are overlapped and are not analysed in detail.

TABLE 3

| | Culture medium (µg/ml in supernatant) | | | | Pellet (µg/ml in cell extract) | | | |
|---|---|---|---|---|---|---|---|---|
| | 7,3'-di-O-glc | 7-O-glc | 3'-O-glc | aglycone | 7,3'-di-O-glc | 7-O-glc | 3'-O-glc | aglycone |
| phosphate buffer alone | 0.00 | 0.00 | 0.19 | 2.23 | 0.00 | 0.00 | 0.00 | 37.09 |
| phosphate buffer + glucose (10 g/L) | 9.10 | 2.20 | 4.44 | 1.24 | 8.85 | 1.64 | 3.58 | 6.08 |

The invention claimed is:

1. A reaction vessel comprising:
   an isolated genetically modified cell wherein said cell is modified by transfection or transformation with a nucleic acid molecule selected from the group consisting of:
   (i) a nucleic acid molecule comprising SEQ ID NO: 1; and
   (ii) a nucleic acid molecule comprising a nucleic acid sequence encoding SEQ ID NO: 2; and
   nutrient medium for supporting the growth of said cell that includes at least one exogenous substrate, wherein said substrate is quercetin and said nutrient medium does not include an exogenous supply of UDP-glucose.

2. The vessel according to claim 1 wherein said vessel is a bioreactor.

3. The vessel according to claim 1 wherein said vessel is a fermentor.

4. The vessel of claim 1 wherein said cell is transformed or transfected with a vector comprising said nucleic acid molecule.

5. The reaction vessel according to claim 1, wherein said genetically modified cell is a eukaryotic cell.

6. The reaction vessel according to claim 5 wherein said eukaryotic cell is a yeast cell; an insect cell; a mammalian cell or a plant cell.

7. The reaction vessel according to claim 6 wherein said cell is a plant cell.

8. The reaction vessel according to claim 1, wherein said genetically modified cell is a prokaryotic cell.

9. A method to glucosylate quercetin comprising:
   providing a reaction vessel according to claim 1; and
   culturing the genetically modified cell in the nutrient medium under growth conditions conducive to culturing the cell.

10. The reaction vessel of claim 9, wherein the genetically modified cell is a eukaryotic cell.

11. The reaction vessel of claim 9, wherein the genetically modified cell is a prokaryotic cell.

* * * * *